US007906326B2

(12) United States Patent
Bentwich

(10) Patent No.: US 7,906,326 B2
(45) Date of Patent: Mar. 15, 2011

(54) BIOINFORMATICALLY DETECTABLE GROUP OF NOVEL REGULATORY OLIGONUCLEOTIDES ASSOCIATED WITH ALZHEIMER'S DISEASE AND USES THEREOF

(75) Inventor: Itzhak Bentwich, Kfar Daniel (IL)

(73) Assignee: Rosetta Genomics Ltd., Rehovot (IL)

( * ) Notice: Subject to any disclaimer, the term of this patent is extended or adjusted under 35 U.S.C. 154(b) by 568 days.

(21) Appl. No.: 10/708,204

(22) Filed: Feb. 16, 2004

(65) Prior Publication Data
US 2005/0222399 A1 Oct. 6, 2005

Related U.S. Application Data

(63) Continuation-in-part of application No. 10/649,653, filed on Aug. 28, 2003, now abandoned, and a continuation-in-part of application No. 10/651,227, filed on Aug. 29, 2003, now abandoned, and a continuation-in-part of application No. 10/707,147, filed on Nov. 24, 2003, and a continuation-in-part of application No. 10/604,985, filed on Aug. 29, 2003, now abandoned, and a continuation-in-part of application No. 10/604,926, filed on Aug. 27, 2003, now abandoned, and a continuation-in-part of application No. 10/604,727, filed on Aug. 13, 2003, now abandoned, and a continuation-in-part of application No. 10/604,726, filed on Aug. 13, 2003, and a continuation-in-part of application No. 10/707,975, filed on Jan. 29, 2004, now abandoned, and a continuation-in-part of application No. 10/707,980, filed on Jan. 29, 2004.

(60) Provisional application No. 60/468,251, filed on May 7, 2003, now abandoned.

(30) Foreign Application Priority Data

Nov. 26, 2003 (WO) .................. PCT/IL03/00998

(51) Int. Cl.
*C07H 21/02* (2006.01)
*C07H 21/04* (2006.01)
*C12Q 1/68* (2006.01)
*C12N 15/00* (2006.01)
(52) U.S. Cl. ....... 435/320.1; 435/6; 536/23.1; 536/24.1; 536/24.31; 536/24.5
(58) Field of Classification Search .................. None
See application file for complete search history.

(56) References Cited

U.S. PATENT DOCUMENTS

| 5,541,308 | A  | * | 7/1996  | Hogan et al. ............... 536/23.1 |
| 6,573,099 | B2 |   | 6/2003  | Graham |
| 6,582,908 | B2 | * | 6/2003  | Fodor et al. ............... 435/6 |
| 6,812,339 | B1 | * | 11/2004 | Venter et al. ............... 536/24.31 |
| 2002/0086356 | A1 |   | 7/2002  | Tuschl et al. |
| 2003/0108923 | A1 |   | 6/2003  | Tuschl et al. |
| 2003/0228691 | A1 |   | 12/2003 | Lewis et al. |
| 2005/0059005 | A1 | * | 3/2005  | Tuschl et al. ............... 435/6 |
| 2006/0105360 | A1 | * | 5/2006  | Croce et al. ............... 435/6 |

FOREIGN PATENT DOCUMENTS

| WO | WO 01/75164     |    | 2/2003 |
| WO | WO 03/029459    |    | 4/2003 |
| WO | WO 03029459  A2 | *  | 4/2003 |
| WO | WO 2004/009779  |    | 1/2004 |

OTHER PUBLICATIONS

Krutzfeldt et al. (2006) Nature Genetics 38:514-519.*
New England Biolabs 1998/99 Catalog, cover page, p. 121 and 284.*
Bentwich (2005) FEBS Lett. 579:5904-5910.*
Bentwich et al. (2005) FEBS Lett. 579:5904-5910.*
Martin et al. (2007) J. Biosci. 32:1049-1052.*
Maziere et al. (2007) Drug Discovery Today 12:452-458.*
Smalheiser et al. (2006) Methods Mol. Biol. 342:115-127.*
Zhao et al. (1997) GenBank Acc. No. AQ420078.*
Buck et al. (Biotechniques (1999) 27(3): 526-538).*
Lagos-Quintana et al. (2002) Curr. Biol. 12:735-739.*
Kim et al. (2004) PNAS 101:360365, including Table 2.*
Cullen (2004) "Derivation and function of small interfering RNAs and microRNAs" Viral Res. 102:3-9.*
Brown (1998) "In situ hybridization with riboprobes: An overview for veterinary pathologists" Vet. Pathol. 35:159-1.*
Ashrafi, K., F. Y. Chang, J. L. Watts, A. G. Fraser, R. S. Kamath, J. Ahringer and G. Ruvkun. Genome-wide RNAi analysis of *Caenorhabditis elegans* fat regulatory genes Nature Jan. 16, 2003 268-272 421.
Kamath, R. S., A. G. Fraser, Y. Dong, G. Poulin, R. Durbin, M. Gotta, A. Kanapin, N. Le Bot, S. Moreno, M. Sohrmann, D. P. Welchman, P. Zipperlen and J. Ahringer. Systematic functional analysis of the *Caenorhabditis elegans* genome using RNAi Nature Jan. 16, 2003 231-237 421.

(Continued)

*Primary Examiner* — Sean R McGarry
(74) *Attorney, Agent, or Firm* — Teddy C. Scott, Jr.; Ron Galant; Polsinelli Shughart PC

(57) ABSTRACT

The present invention relates to a first group of novel oligonucleotides, here identified as genomic address messenger or GAM oligonucleotides, and a second group of novel operon-like polynucleotides, here identified as genomic record or GR polynucleotides. GAM oligonucleotides selectively inhibit translation of known target genes, many of which are known to be involved in various diseases. Nucleic acid molecules are provided respectively encoding 1708 GAM oligonucleotides, and 246 GR polynucleotides as are vectors and probes both comprising the nucleic acid molecules, and methods and systems for detecting GAM oligonucleotides and GR polynucleotide and specific functions and utilities thereof, for detecting expression of GAM oligonucleotides and GR polynucleotides and for selectively enhancing and selectively inhibiting translation of the respective target genes thereof.

6 Claims, 31 Drawing Sheets

OTHER PUBLICATIONS

Tuschl, T. Functional genomics: RNA sets the standard Nature Jan. 16, 2003 220-221 421.

Iyer, L. M., E. V. Koonin and L. Aravind. Evolutionary connection between the catalytic subunits of DNA-dependent RNA polymerases and eukaryotic RNA-dependent RNA polymerases and the origin of RNA polymerases BMC Struct Biol Jan. 28, 2003 1 3.

Kawasaki, H., E. Suyama, M. Iyo and K. Taira. siRNAs generated by recombinant human Dicer induce specific and significant but target site-independent gene silencing in human cells Nucleic Acids Res Feb. 1, 2003 981-987 31.

Reiner, A., D. Yekutieli and Y. Benjamini. Identifying differentially expressed genes using false discovery rate controlling procedures Bioinformatics Feb. 12, 2003 368-375 19.

Doench, J. G., C. P. Petersen and P. A. Sharp. siRNAs can function as miRNAs Genes Dev Feb. 15, 2003 438-442 17.

Carmichael, G. G. Antisense starts making more sense Nat Biotechnol Apr. 2003 371-372 21.

Colciaghi, F., E. Marcello, B. Borroni, M. Zimmermann, C. Caltagirone, F. Cattabeni, A. Padovani and M. Di Luca. Platelet APP, ADAM 10 and BACE alterations in the early stages of Alzheimer disease Neurology Feb. 10, 2004 498-501 62.

Boden, D., O. Pusch, R. Silbermann, F. Lee, L. Tucker and B. Ramratnam. Enhanced gene silencing of HIV-1 specific siRNA using microRNA designed hairpins Nucleic Acids Res Feb. 13, 2004 1154-1158 32.

Bohnsack, M. T., K. Czaplinski and D. Gorlich. Exportin 5 is a RanGTP-dependent dsRNA-binding protein that mediates nuclear export of pre-miRNAs Rna Feb. 2004 185-191 10.

Demidov, V. V. and M. D. Frank-Kamenetskii. Two sides of the coin: affinity and specificity of nucleic acid interactions Trends Biochem Sci Feb. 2004 62-71 29.

Maquat, L. E. Nonsense-mediated mRNA decay: splicing, translation and mRNP dynamics Nat Rev Mol Cell Biol Feb. 2004 89-99 5.

Nijholt, I., N. Farchi, M. Kye, E. H. Sklan, S. Shoham, B. Verbeure, D. Owen, B. Hochner, J. Spiess, H. Soreq and T. Blank. Stress-induced alternative splicing of acetylcholinesterase results in enhanced fear memory and long-term potentiation Mol Psychiatry Feb. 2004 174-183 9.

Sengupta, P. Taking sides in the nervous system with miRNA Nat Neurosci Feb. 2004 100-102 7.

Zerhouni, B., J. A. Nelson and K. Saha. Isolation of CD4-independent primary human immunodeficiency virus type 1 isolates that are syncytium inducing and acutely cytopathic for CD8+ lymphocytes J Virol Feb. 2004 1243-1255 78.

Jin, P., D. C. Zarnescu, S. Ceman, M. Nakamoto, J. Mowrey, T. A. Jongens, D. L. Nelson, K. Moses and S. T. Warren. Biochemical and genetic interaction between the fragile X mental retardation protein and the microRNA pathway Nat Neurosci Feb. 2004 113-117 7.

Lai, E. C., C. Wiel and G. M. Rubin. Complementary miRNA pairs suggest a regulatory role for miRNA:miRNA duplexes Rna Feb. 2004 171-175 10.

Metzler, M., M. Wilda, K. Busch, S. Viehmann and A. Borkhardt. High expression of precursor microRNA-155/BIC RNA in children with Burkitt lymphoma Genes Chromosomes Cancer Feb. 2004 167-169 39.

Ohno K, et al. Choline acetyltransferase mutations cause myasthenia syndrome associated with episodic apnea in humans. PNAS, 2001;98(4):2017-22.

Doench JG and Sharp PA. Genes Dev, 2004;18(5):504-11.

Lai EC, Predicting and validating microRNA targets, Genome Biology 2004;5:115.

Vella MC, Architecture of a validated microRNA::target interaction, Chemistry & Biology 2004;11:1619-23.

Brennecke J, Principles of MicroRNA-target recognition, PLoS Biology 2005;3(3):e85.

Lim LP, Microarray analysis shows that some micro RNAs downregulate large numbers of target mRNAs, Nature 2005;433(7027):769-73.

Ikari Y, a1-Proteinase Inhibitor, a1-Antichymotrypsin, and a2-Macroglobulin Are theAntiapoptotic Factors of Vascular Smooth Muscle Cells, J Biol Chem 2001;276(15):11798-803.

Inui, T et al. Cathepsin K Antisense Oligodeoxynucleotide Inhibits Osteoclastic Bone Resorption. J Biol Chem, 1997;272(13):8109-12.

Morin, R.D. et al., "Application of massively parallel sequencing to microRNA profiling and discovery of human embryonic stem cells," Genome Res., 2008;18:610-21.

Zamore, P.D., et al., "RNAi: Double-Stranded RNA Directs the ATP-Dependent Cleavage of mRNA at 21 to 23 Nucleotide Intervals," Cell, 2000;101:25-33.

Elbashir, S.M. et al., "RNA interference is mediated by 21- and 22-nucleotide RNAs", Genes and Development, 2001;15:188-200.

Lim, L.P. et al., "The microRNAs of *Caenorhabditis elegans*," Genes & Dev., 2003;17:991-1008.

Bartel, D.P., "MicroRNAs: Genomics, Biogenesis, Mechanism, and Function," Cell, 2004;116:281-97.

* cited by examiner

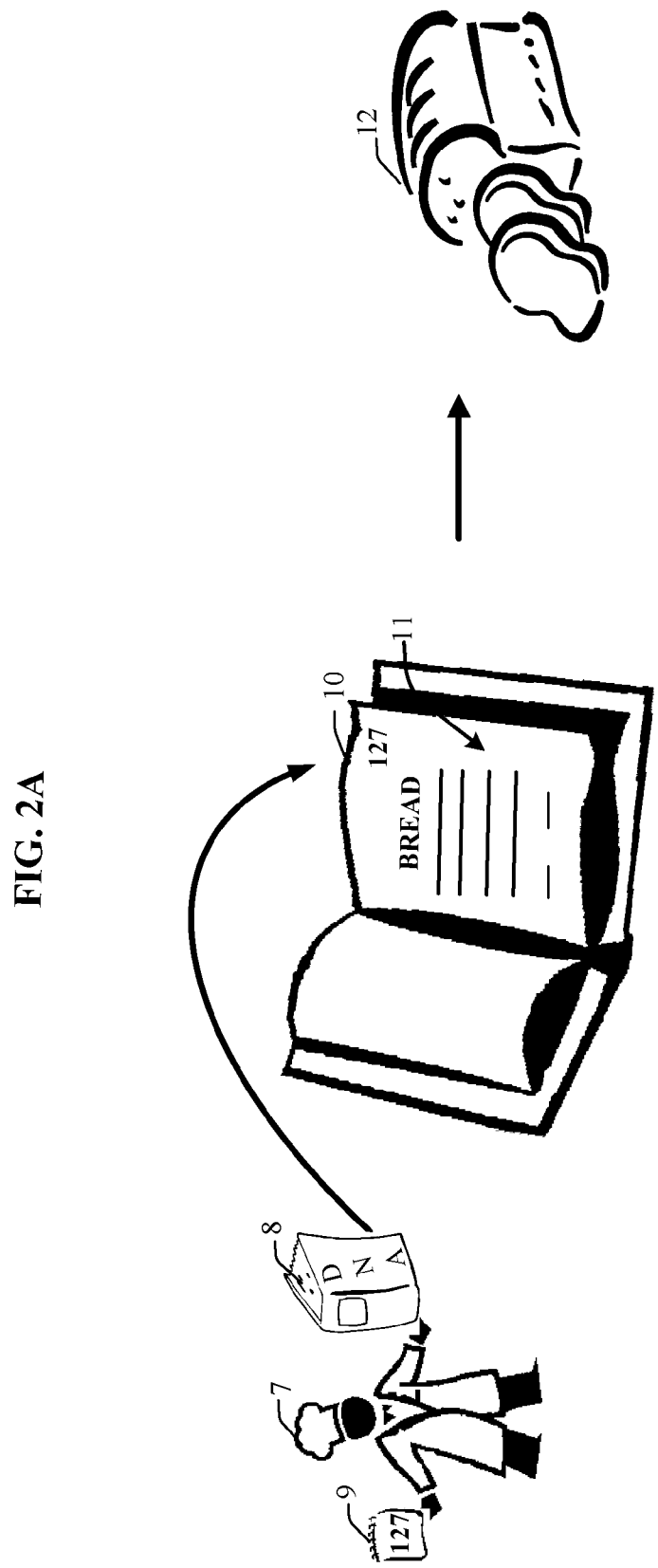

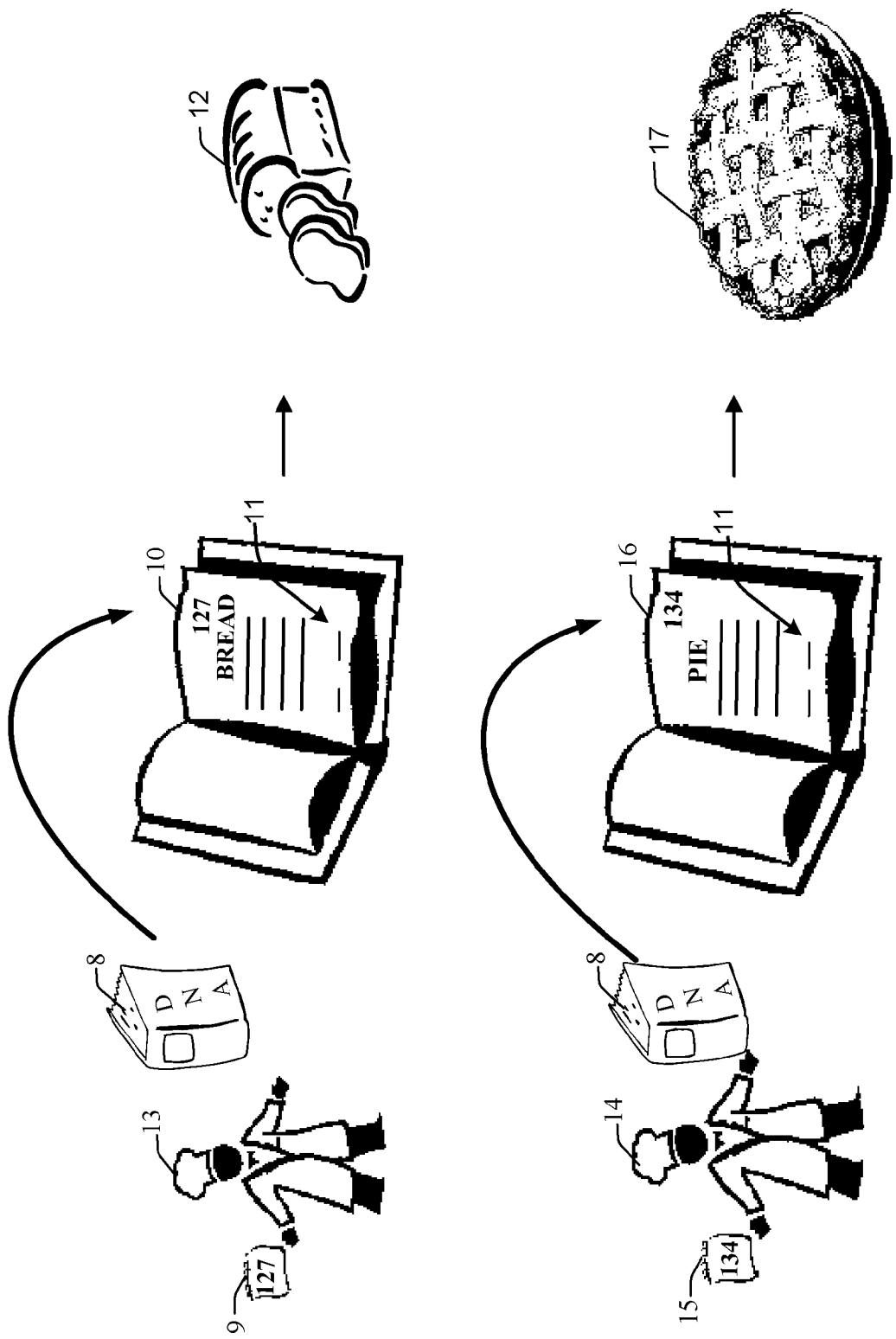

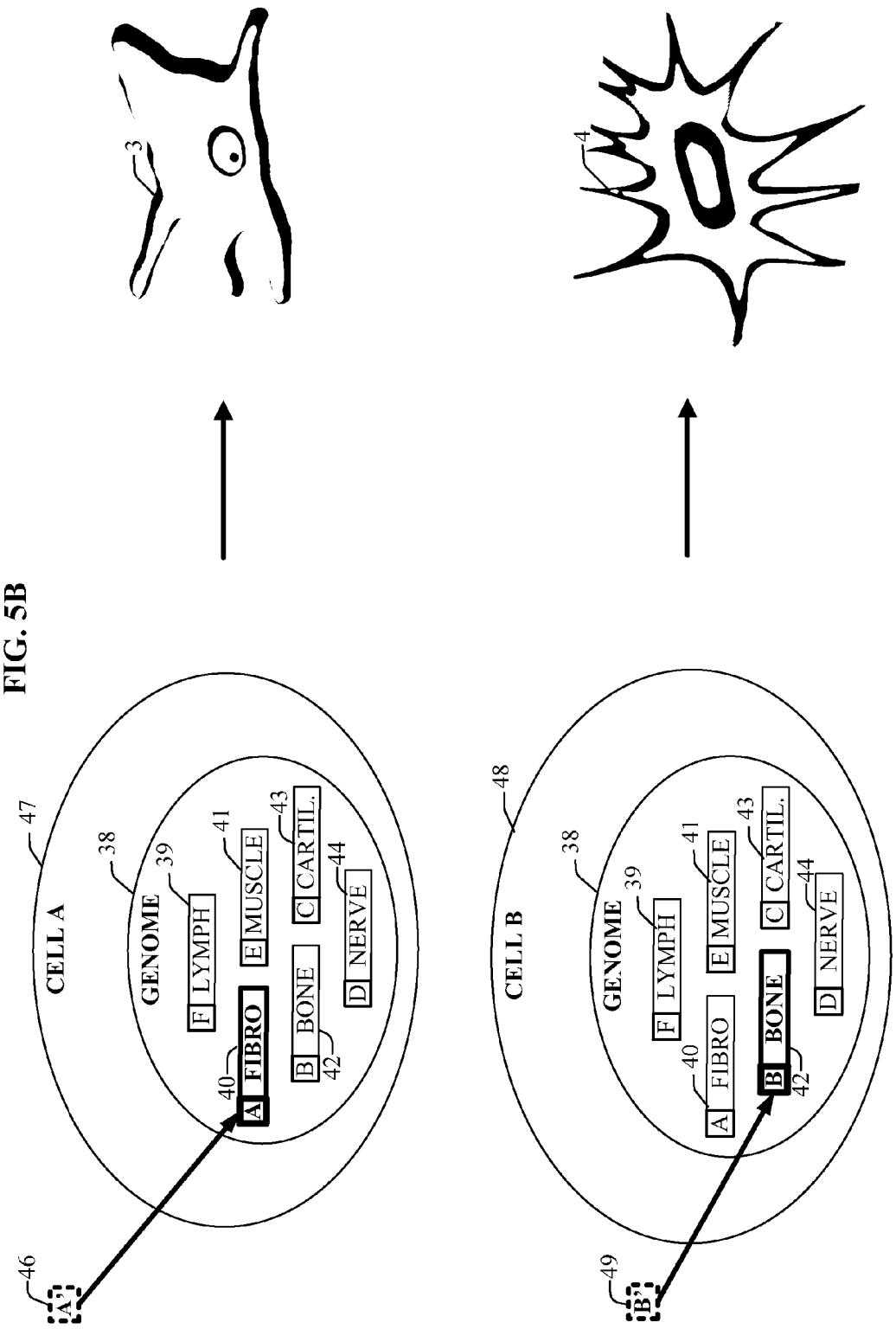

FIG. 21B

| GAM Detection Accuracy Group | Number of published hairpins | Precision on hairpin mixture | Lab validation of Human GAMs | | | Hairpins in RNA databases | Hairpins of the present invention |
| --- | --- | --- | --- | --- | --- | --- | --- |
| | | | Sent | Positive | % success | | |
| A | 228 | 76% | 101 | 37 | 37% | 2821 | 1419 |
| B | 135 | 41% | 56 | 13 | 23% | 19950 | 333 |
| C | 27 | 18% | 7 | 1 | 14% | 11765 | 18 |
| D | 20 | 10% | 4 | 1 | 25% | 7876 | 2 |
| Overall | 410 | 44% | 168 | 52 | 31% | 42416 | 1708 |

FIG. 22B

| NUMBER | NAME | SEQUENCE (5 TO 3) | SEQUENCED | SEQ ID NO |
|---|---|---|---|---|
| 1 | hsa-miR-21 | TAGCTTATCAGACTGATGTTGA | + | 7352 |
| 2 | hsa-miR-27b | TTCACAGTGGCTAAGTTCTGCA | + | 7353 |
| 3 | hsa-miR-186 | AAAGAATTCTCCTTTTGGGCTT | + | 7354 |
| 4 | hsa-miR-93 | AAGTGCTGTTCGTGCAGGTAGT | + | 7355 |
| 5 | hsa-miR-26a | TCAAGTAATCCAGGATAGGCTG | + | 7356 |
| 6 | hsa-miR-191 | AACGGAATCCCAAAAGCAGCTG | + | 7357 |
| 7 | hsa-miR-31 | GGCAAGATGCTGGCATAGCTGT | + | 7358 |
| 8 | hsa-miR-92 | TATTGCACTTGTCCCGGCCTGT | + | 7359 |
| 9 | GAM3418-A | ATCACATTGCCAGGGATTACCA | + | 7360 |
| 10 | GAM4426-A | GAAGTTTGAAGCCTGTTGTTCA | + | 7361 |
| 11 | GAM281-A | CACTGCACTCCAGCCTGGGCAA |  | 7362 |
| 12 | GAM7553-A | TAGGTAGTTTCCTGTTGTTGGG | + | 7363 |
| 13 | GAM5385-A | TCACAGTGAACCGGTCTCTTTC | + | 7364 |
| 14 | GAM2608-A | TAAGGTGCATCTAGTGCAGTTA |  | 7365 |
| 15 | GAM1032-A | CTAGACTGAAGCTCCTTGAGGA | + | 7366 |
| 16 | GAM3431-A | TAATACTGCCGGGTAATGATGG |  | 7367 |
| 17 | GAM7933-A | TAGCAGCACATAATGGTTTGAA |  | 7368 |
| 18 | GAM3298-A | AAAGTGCTCATAGTGCAGGTAG | + | 7369 |
| 19 | GAM7080-A | TTTCCACAGCGGCCAATTCTTC | + | 7370 |
| 20 | GAM895-A | AGCTGCCAGTTGAAGAACATTT |  | 7371 |
| 21 | GAM3770-A | AAGTTAAGAGCTCCCAGGCCTG |  | 7372 |
| 22 | GAM337162-A | ACTGCACTCCAGCCTGGGCAAC | + | 7373 |
| 23 | GAM8678-A | GTGTTCCAGGAAGTCGTCTTGA |  | 7374 |
| 24 | GAM2033-A | TCAAGCTCATTCCTCTAACCTC |  | 7375 |
| 25 | GAM7776-A | CATTGCACTCCAGCCTGGGCAA | + | 7376 |
| 26 | GAM8145-A | ACATGATCTCCTCACTCTAGGA |  | 7377 |
| 27 | GAM25-A | AATTGCTTGAACCCAGGAAGTG | + | 7378 |
| 28 | GAM7352-A | TGTTTAAGTAGCTTATTTATCT |  | 7379 |
| 29 | GAM337624-A | TCTAAGAGAAAGGAAGTTCAGA | + | 7380 |
| 30 | GAM1479-A | GAAGGCAGTAGGTTGTATAGTT | + | 7381 |
| 31 | GAM2270-A | ATCACATTGCCAGTGATTACCC | + | 7382 |
| 32 | GAM7591-A | TTGGAGTAATTCAGTATAGGTT | + | 7383 |
| 33 | GAM8285-A | AGTAGACAGTGGCAACATAGTC |  | 7384 |
| 34 | GAM6773-A | CTAGCCTGTTTGTCCTCACCCC | + | 7385 |
| 35 | GAM336818-A | TGAGGTGGGATCCCGAGGCC | + | 7386 |
| 36 | GAM336487 -A | TGGCTAGGTAAGGGAAG | + | 7387 |
| 37 | GAM337620-A | AATCATCATTATTTTGAAGTTTA | + | 7388 |
| 38 | GAM336809-A | T AAGGCATTTTT A TGGT | + | 7389 |
| 39 | GAM5346-A | GCTGTTGTTAAGGGCACTTGGG |  | 7390 |
| 40 | GAM8554-A | TTCATGGGAGCAGGTGGTACAG |  | 7391 |
| 41 | GAM2701-A | ACTGCACTCCAGTCTGGGTGAC |  | 7392 |
| 42 | GAM7957-A | TCACTGCAACCTCTGCCTCCCG |  | 7393 |
| 43 | GAM391-A | CAGATCACATCCATCCGTCACC |  | 7394 |
| 44 | GAM6633-A | GCACTCAAGCCTGGGTTACAGA |  | 7395 |
| 45 | GAM19 | AGAGAGTGGCAGGTCTGTTCCT |  | 7396 |
| 46 | GAM8358-A | GATGAGGCAGCACTTGGG |  | 7397 |
| 47 | GAM3229-A | TGAGGTGGGAGAATTGCTTGAA |  | 7398 |
| 48 | GAM7052-A | CATGTAATCCCAGCTACTCAGG |  | 7399 |
| 49 | GAM3027-A (mmu-MIR-29c) | TAGCACCATTTGAAATCGGTTA | + | 7400 |
| 50 | GAM21 (m mu - MIR-130b) | CAGTGCAATGATGAAAGGGCAT | + | 7401 |
| 51 | GAM oligonucleotide (mmu-MIR 30e) | TGTAAACATCCTTGACTGGAAG | + | 7402 |

FIG. 24A

EST72223 (705 nt.)

Chr.X

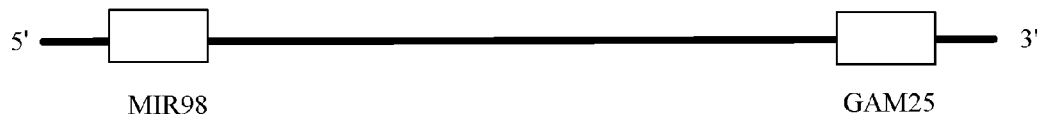

MIR98            GAM25

EST72223 sequence:

CCCTTATTAGAGGATTCTGCTCATGCCAGG**GTGAGGTAGTAAGTTGTATTG
TTG**TGGGGTAGGGATATTAGGCCCCAATTAGAAGATAACTATACAACT    MIR98
TACTACTTTCCCTGGTGTGTGGCATATTCACACTTAGTCTTAGCAGTGTTGCC
TCCATCAGACAAAGTTGTAGATGTTCCTTGGATAATTTGGACTGGAAGAAAGA
GACATGGAAGGGGACAGATGGTGTTTAGGGTGAGGCAGATGTCATTATAAAGT
GACTTGTCTTTCATTAATTGGAGCATATAATTATTTTACCTTTGGGCATGAACTC
ATTTTGCTATTCTTCAACTGTGTAATGATTGCATTTTATTAGTAATAGAACAGGA
ATGTGTGCAAGGGAATGGAAAGCATACTTTAAGAATTTTGGGCCAGGCGCGGT
GGTTCATGCCTGTAATCCCAGCATTTTTGGGAGGCCGAGGCGGGTGGATCAC
CTGAGGTCAGGAGTTCGAGACCAACCTGGCCAACACGGCGAAACCCCGCCTC
TACTCAAATACAAAAATTAGCCAGGCTTGGTGACACTCGCCTGTGGTCCCAGC
TACTCAGGAGGCTGAGGCAGGAGAATTGCTTGAACCCAGGAAGTGGAG    GAM25
GCTTCAGTGAGCTGAGAACACGCCACTGCACTCCAGTCCTGGGCAAC
AGAGCAAGACTCTGTCTCAGGAAAAAAAAAG

FIG. 24B

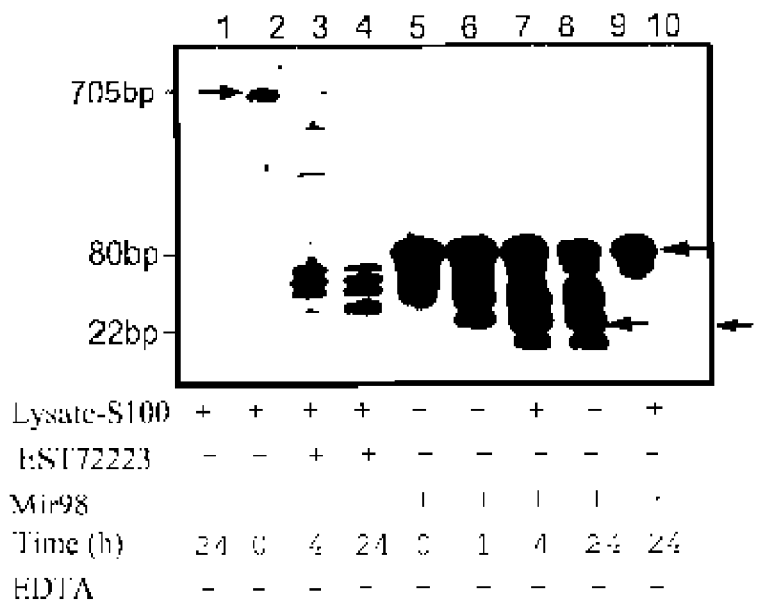

BIOINFORMATICALLY DETECTABLE GROUP OF NOVEL REGULATORY OLIGONUCLEOTIDES ASSOCIATED WITH ALZHEIMER'S DISEASE AND USES THEREOF

CROSS REFERENCE TO RELATED APPLICATIONS

This application is a continuation in part of and claims priority from the following patent applications, the disclosures of which applications are all hereby incorporated herein by reference: U.S. patent application Ser. No. 10/707,975 filed 29 Jan. 2004, U.S. patent application Ser. No. 10/707,147 filed 24 Nov. 2003, U.S. patent application Ser. No. 10/707,147 filed 24 Nov. 2003, U.S. patent application Ser. No. 10/604,985 filed 29 Aug. 2003, U.S. patent application Ser. No. 10/651,227 filed 29 Aug. 2003, U.S. patent application Ser. No. 10/649,653 filed 28 Aug. 2003, U.S. patent application Ser. No. 10/604,926 filed 27 Aug. 2003, U.S. patent application Ser. No. 10/604,726 filed 13 Aug. 2003, U.S. patent application Ser. No. 10/604,727 filed 13 Aug. 2003, and U.S. Provisional Patent Application Ser. No. 60/468,251 filed 2007 May 2003. This application also claims priority from International application Number: PCT/IL 03/00970, filed 16 Nov. 2003, the disclosure of which application is hereby incorporated herein by reference. All of the aforesaid patent applications are entitled "Bioinformatically Detectable Group of Novel Regulatory Genes and Uses Thereof"; This application also claims priority from U.S. patent application Ser. No. 10/707,980 filed 29 Jan. 2004, entitled "Bioinformatically Detectable Group of Novel Regulatory Oligonucleotides and Uses Thereof"; U.S. patent application Ser. No. 10/707,980, filed 29 Jan. 2004, entitled "Bioinformatically Detectable Group of Novel Regulatory Oligonucleotides and Uses Thereof" is a continuation in part of and claims priority from the following patent applications, the disclosures of which applications are all hereby incorporated herein by reference: U.S. patent application Ser. No. 10/707,147 filed 24 Nov. 2003, U.S. patent application Ser. No. 10/707,147 filed 24 Nov. 2003, U.S. patent application Ser. No. 10/604,985 filed 29 Aug. 2003, U.S. patent application Ser. No. 10/651,227 filed 29 Aug. 2003, U.S. patent application Ser. No. 10/649,653 filed 28 Aug. 2003, U.S. patent application Ser. No. 10/604,926 filed 27 Aug. 2003, U.S. patent application Ser. No. 10/604,726 filed 13 Aug. 2003, U.S. patent application Ser. No. 10/604,727 filed 13 Aug. 2003, and U.S. Provisional patent application Ser. No. 60/468,251 filed 7 May 2003. This application also claims priority from International application Number: PCT/IL 03/00970, filed 16 Nov. 2003, the disclosure of which application is hereby incorporated herein by reference. All of the aforesaid patent applications are entitled "Bioinformatically Detectable Group of Novel Regulatory Genes and Uses Thereof"; U.S. patent application Ser. No. 10/707,975, filed 29 Jan. 2004, entitled "Bioinformatically Detectable Group of Novel Regulatory Genes and Uses Thereof" is a continuation in part of and claims priority from the following patent applications, the disclosures of which applications are all hereby incorporated herein by reference: U.S. patent application Ser. No. 10/707,147 filed 24 Nov. 2003, U.S. patent application Ser. No. 10/707,147 filed 24 Nov. 2003, U.S. patent application Ser. No. 10/604,985 filed 29 Aug. 2003, U.S. patent application Ser. No. 10/651,227 filed 29 Aug. 2003, U.S. patent application Ser. No. 10/649,653 filed 28 Aug. 2003, U.S. patent application Ser. No. 10/604,926 filed 27 Aug. 2003, U.S. patent application Ser. No. 10/604,726 filed 13 Aug. 2003, U.S. patent application Ser. No. 10/604,727 filed 13 Aug. 2003, and U.S. Provisional patent application Ser. No. 60/468,251 filed 7 May 2003. This application also claims priority from International application Number: PCT/IL 03/00970, filed 16 Nov. 2003, the disclosure of which application is hereby incorporated herein by reference. All of the aforesaid patent applications are entitled "Bioinformatically Detectable Group of Novel Regulatory Genes and Uses Thereof"; U.S. patent application Ser. No. 10/707,147, filed 24 Nov. 2003, entitled "Bioinformatically Detectable Group of Novel Regulatory Genes and Uses Thereof" is a continuation in part of and claims priority from the following patent applications, the disclosures of which applications are all hereby incorporated herein by reference: U.S. patent application Ser. No. 10/604,985 filed 29 Aug. 2003, U.S. patent application Ser. No. 10/651,227 filed 29 Aug. 2003, U.S. patent application Ser. No. 10/649,653 filed 28 Aug. 2003, U.S. patent application Ser. No. 10/604,926 filed 27 Aug. 2003, U.S. patent application Ser. No. 10/604,726 filed 13 Aug. 2003, U.S. patent application Ser. No. 10/604,727 filed 13 Aug. 2003, and U.S. Provisional patent application Ser. No. 60/468,251 filed 7 May 2003. This application also claims priority from International application Number: PCT/IL 03/00970, filed 16 Nov. 2003, the disclosure of which application is hereby incorporated herein by reference. All of the aforesaid patent applications are entitled "Bioinformatically Detectable Group of Novel Regulatory Genes and Uses Thereof"; International application Number: PCT/IL 03/00970, filed 16 Nov. 2003, entitled "Bioinformatically Detectable Group of Novel Regulatory Genes and Uses Thereof" is a continuation in part of and claims priority from the following patent applications, the disclosures of which applications are all hereby incorporated herein by reference: U.S. patent application Ser. No. 10/604,985 filed 29 Aug. 2003, U.S. patent application Ser. No. 10/651,227 filed 29 Aug. 2003, U.S. patent application Ser. No. 10/649,653 filed 28 Aug. 2003, U.S. patent application Ser. No. 10/604,926 filed 27 Aug. 2003, U.S. patent application Ser. No. 10/604,726 filed 13 Aug. 2003, U.S. patent application Ser. No. 10/604,727 filed 13 Aug. 2003, U.S. Provisional patent application Ser. No. 60/468,251 filed 7 May 2003, and U.S. patent application Ser. No. 10/345,201 filed 16 Jan. 2003. All of the aforesaid patent applications are entitled "Bioinformatically Detectable Group of Novel Regulatory Genes and Uses Thereof"; U.S. patent application Ser. No. 10/604,985, filed 29 Aug. 2003, entitled "Bioinformatically is a continuation of U.S. Provisional patent application Ser. No. 60/468,251, filed 7 May 2003, entitled "Bioinformatically Detectable Group of Novel Regulatory Genes and Uses Thereof" the disclosure of which is hereby incorporated herein and claims priority therefrom; and is a continuation in part of and claims priority from the following patent applications, the disclosures of which applications are all hereby incorporated herein by reference: U.S. patent application Ser. No. 10/651,227 filed 29 Aug. 2003, U.S. patent application Ser. No. 10/649,653 filed 28 Aug. 2003, U.S. patent application Ser. No. 10/604,926 filed 27 Aug. 2003, U.S. patent application Ser. No. 10/604,726 filed 13 Aug. 2003, U.S. patent application Ser. No. 10/604,727 filed 13 Aug. 2003, U.S. patent application Ser. No. 10/345,201 filed 16 Jan. 2003, U.S. patent application Ser. No. 10/321,503 filed 18 Dec. 2002, U.S. patent application Ser. No. 10/310,914 filed 2006 Dec. 2002, and U.S. patent application Ser. No. 10/293,338 filed 14 Nov. 2002. All of the aforesaid patent applications are entitled "Bioinformatically Detectable Group of Novel Regulatory Genes and Uses Thereof"; U.S. patent application Ser. No. 10/604,926, filed 27 Aug. 2003, entitled "Bioinformatically Detectable Group of Novel Regulatory Genes and Uses Thereof" is a continuation of U.S. patent application Ser. No. 10/345,201, filed 16 Jan. 2003, entitled "Bioinformatically Detectable Group of Novel Regulatory Genes and Uses Thereof" the disclosure of which is hereby incorporated herein and claims priority therefrom; and is a continuation in part of and claims priority from the following patent applications, the disclosures of which applications are all hereby incorporated herein by reference: U.S. patent application Ser. No. 10/604,726 filed 13 Aug. 2003, U.S. patent application Ser. No. 10/604,727 filed 13 Aug. 2003, U.S. Provisional patent application Ser. No. 60/468,251 filed 7 May 2003, U.S. patent application Ser. No. 10/321,503 filed 18 Dec. 2002, U.S. patent application Ser. No. 10/310,914 filed 6 Dec. 2002, and U.S. patent application Ser. No. 10/293,338 filed 14 Nov. 2002. All of the aforesaid patent applications are entitled "Bioinformatically Detectable Group of Novel Regulatory Genes and Uses Thereof"; U.S. patent application Ser. No. 10/649,653, filed 28 Aug. 2003, entitled "Bioinformatically Detectable Group of Novel Regulatory Genes and Uses Thereof" is a continuation of U.S. patent application Ser. No. 10/321,503, filed 18 Dec. 2002, entitled "Bioinformatically Detectable Group of Novel Regulatory Genes and Uses Thereof"; the disclosure of which is hereby incorporated herein and claims priority therefrom; and is a continuation in part of and claims priority from the following patent applications, the disclosures of which applications are all hereby incorporated herein by reference: U.S. patent application Ser. No. 10/604,926 filed 27 Aug. 2003, U.S. patent application Ser. No. 10/604,726 filed 13 Aug. 2003, U.S. patent application Ser. No. 10/604,727 filed 13 Aug. 2003, U.S. Provisional patent application Ser. No. 60/468,251 filed 7 May 2003, U.S. patent application Ser. No. 10/321,503 filed 18 Dec. 2002, U.S. patent application Ser. No. 10/310,914 filed 6 Dec. 2002, and U.S. patent application Ser. No. 10/293,338 filed 14 Nov. 2002. All of the aforesaid patent applications are entitled "Bioinformatically Detectable Group of Novel Regulatory Genes and Uses Thereof"; U.S. patent application Ser. No. 10/651,227, filed 29 Aug. 2003, entitled "Bioinformatically Detectable Group of Novel Regulatory Genes and Uses Thereof" is a continuation of U.S. patent application Ser. No. 10/310,914, filed 6 Dec. 2002, entitled "Bioinformatically Detectable Group of Novel Regulatory Genes and Uses Thereof"; the disclosure of which is hereby incorporated herein and claims priority therefrom; and is a continuation in part of and claims priority from the following patent applications, the disclosures of which applications are all hereby incorporated herein by reference: U.S. patent application Ser. No. 10/604,985 filed 29 Aug. 2003, U.S. patent application Ser. No. 10/649,653 filed 28 Aug. 2003, U.S. patent application Ser. No. 10/604,926 filed 27 Aug. 2003, U.S. patent application Ser. No. 10/604,726 filed 13 Aug. 2003, U.S. patent application Ser. No. 10/604,727 filed 13 Aug. 2003, U.S. Provisional Patent Application Ser. No. 60/468,251 filed 7 May 2003, U.S. patent application Ser. No. 10/345,201 filed 16 Jan. 2003, U.S. patent application Ser. No. 10/321,503 filed 18 Dec. 2002, U.S. patent application Ser. No. 10/310,914 filed 6 Dec. 2002, and U.S. patent application Ser. No. 10/293,338 filed 14 Nov. 2002. All of the aforesaid patent applications are entitled "Bioinformatically Detectable Group of Novel Regulatory Genes and Uses Thereof"; U.S. patent application Ser. Nos. 10/604,727 and 10/604,726, filed 13 Aug. 2003, entitled "Bioinformatically Detectable Group of Novel Regulatory Genes and Uses Thereof" are a continuation of U.S. patent application Ser. No. 10/293,338, filed 14 Nov. 2002, entitled "Bioinformatically Detectable Group of Novel Regulatory Genes and Uses Thereof", the disclosure of which is hereby incorporated herein and claims priority therefrom; and are a continuation in part of and claims priority from the following patent applications, the disclosures of which applications are all hereby incorporated herein by reference: U.S. Provisional Patent Application Ser. No. 60/468,251 filed 7 May 2003, U.S. patent application Ser. No. 10/345,201 filed 16 Jan. 3, U.S. patent application Ser. No. 10/321,503 filed 18 Dec. 2002, U.S. patent application Ser. No. 10/310,914 filed 6 Dec. 2002, and U.S. patent application Ser. No. 10/293,338 filed 14 Nov. 2002. All of the aforesaid patent applications are entitled "Bioinformatically Detectable Group of Novel Regulatory Genes and Uses Thereof"; U.S. Provisional Patent Application Ser. No. 60/468,251, filed 7 May 2003, entitled "Bioinformatically Detectable Group of Novel Regulatory Genes and Uses Thereof" is a continuation in part of and claims priority from the following patent applications, the disclosures of which applications are all hereby incorporated herein by reference: U.S. patent application Ser. No. 10/345,201 filed 16 Jan. 2003, U.S. patent application Ser. No. 10/321,503 filed 18 Dec. 2002, U.S. patent application Ser. No. 10/310,914 filed 6 Dec. 2002, and U.S. patent application Ser. No. 10/293,338 filed 14 Nov. 2002. All of the aforesaid patent applications are entitled "Bioinformatically Detectable Group of Novel Regulatory Genes and Uses Thereof"; U.S. patent application Ser. No. 10/345,201, filed 16 Jan. 2003, entitled "Bioinformatically Detectable Group of Novel Regulatory Genes and Uses Thereof" is a continuation in part of and claims priority from the following patent applications, the disclosures of which applications are all hereby incorporated herein by reference: U.S. patent application Ser. No. 10/321,503 filed 18 Dec. 2002, U.S. patent application Ser. No. 10/310,914 filed 6 Dec. 2002, and U.S. patent application Ser. No. 10/293,338 filed 14 Nov. 2002. All of the aforesaid patent applications are entitled "Bioinformatically Detectable Group of Novel Regulatory Genes and Uses Thereof"; U.S. patent application Ser. No. 10/321,503, filed 18 Dec. 2002, entitled "Bioinformatically Detectable Group of Novel Regulatory Genes and Uses Thereof" is a continuation in part of and claims priority from the following patent applications, the disclosures of which applications are all hereby incorporated herein by reference: U.S. patent application Ser. No. 10/310,914 filed 6 Dec. 2002, and U.S. patent application Ser. No. 10/293,338 filed 14 Nov. 2002. All of the aforesaid patent applications are entitled "Bioinformatically Detectable Group of Novel Regulatory Genes and Uses Thereof"; U.S. patent application Ser. No. 10/310,914, filed 6 Dec. 2002, entitled "Bioinformatically Detectable Group of Novel Regulatory Genes and Uses Thereof" is a continuation in part of U.S. patent application Ser. No. 10/293,338, filed 14 Nov. 2002, entitled "Bioinformatically Detectable Group of Novel Regulatory Genes and Uses Thereof", the disclosure of which is hereby incorporated by reference and claims priority therefrom.

REFERENCES CITED

Altschul, S. F., Gish, W., Miller, W., Myers, E. W., and Lipman, D. J. (1990). Basic local alignment search tool. J. Mol. Biol. 215, 403-410.

Ambros, V., Lee, R. C., Lavanway, A., Williams, P. T., and Jewell, D. (2003). MicroRNAs and Other Tiny Endogenous RNAs in C. elegans 1. Curr. Biol. 13, 807-818.

Calin, G. A., Dumitru, C. D., Shimizu, M., Bichi, R., Zupo, S., Noch, E., Aldler, H., Rattan, S., Keating, M., Rai, K., Rassenti, L., Kipps, T., Negrini, M., Bullrich, F., and Croce, C. M. (2002). Frequent deletions and downregulation of micro-RNA genes miR15 and miR16 at 13q14 in chronic lymphocytic leukemia. Proc. Natl. Acad. Sci. U.S.A.

Dan Gusfield, Algorithms on strings, trees, and sequences: computer science and computational biology, Cambridge University Press, 1997.

Elbashir, S. M., Lendeckel, W., and Tuschl, T. (2001). RNA interference is mediated by 21- and 22-nucleotide RNAs. Genes Dev. 15, 188-200.

Gibbs, W. W. (2003). The unseen genome: gems among the junk. Sci. Am. 289, 46-53.

Gussow, D. and Clackson, T. (1989). Direct clone characterization from plaques and colonies by the polymerase chain reaction. Nucleic Acids Res. 17, 4000.

Hamosh A, Scott A F, Amberger J, Bocchini C, Valle D and McKusick V A. (2002). Online Mendelian Inheritance in Man (OMIM), a knowledgebase of human genes and genetic disorders. Nucleic Acids Res. 30: 52-55.

Jenuth J. P. (2000). The NCBI. Publicly available tools and resources on the Web. Methods Mol. Biol. 132, 301-312.

Kirkness, E. F. and Kerlavage, A. R. (1997). The TIGR human cDNA database. Methods Mol. Biol. 69, 261-268.

Lagos-Quintana, M., Rauhut, R., Lendeckel, W., and Tuschl, T. (2001). Identification of novel genes coding for small expressed RNAs. Science 294, 853-858.

Lau, N. C., Lim, L. P., Weinstein, E. G., and Bartel, D. P. (2001). An abundant class of tiny RNAs with probable regulatory roles in *Caenorhabditis elegans*. Science 294, 858-862.

Lau, N. C. and Bartel, D. P. (2003). Censors of the genome. Sci. Am. 289, 34-41.

Lim, L. P., Glasner, M. E., Yekta, S., Burge, C. B., and Bartel, D. P. (2003). Vertebrate microRNA genes. Science 299, 1540.

Mathews, D. H., Sabina, J., Zuker, M., and Turner, D. H. (1999). Expanded sequence dependence of thermodynamic parameters improves prediction of RNA secondary structure. J. Mol. Biol. 288, 911-940.

Metzler, M., Wilda, M., Busch, K., Viehmann, S., and Borkhardt, A. (2004). High expression of precursor micro RNA-155/BIC RNA in children with Burkitt lymphoma. Genes Chromosomes. Cancer 39, 167-169.

Michael, M. Z., O'Connor, S. M., Holst Pellekaan, N. G., Young, G. P., and James, R. J. (2003). Reduced accumulation of specific microRNAs in colorectal neoplasia. Mol. Cancer Res. 1, 882-891.

Reinhart, B. J., Slack, F. J., Basson, M., Pasquinelli, A. E., Bettinger J. C., Rougvie, A. E., Horvitz, H. R., and Ruvkun, G. (2000). The 21-nucleotide let-7 RNA regulates developmental timing in *Caenorhabditis elegans*. Nature 403, 901-906.

Southern, E. M. (1992). Detection of specific sequences among DNA fragments separated by gel electrophoresis. 1975. Biotechnology 24, 122-139.

Tom M. Mitchell, Machine Learning, McGraw Hill, 1997.

Wightman, B., Ha, I., and Ruvkun, G. (1993). Posttranscriptional regulation of the heterochronic gene lin-14 by lin-4 mediates temporal pattern formation in *C. elegans*. Cell 75, 855-862.

Zhang, H., Kolb, F. A., Brondani, V., Billy, E., and Filipowicz, W. (2002). Human Dicer preferentially cleaves dsRNAs at their termini without a requirement for ATP. EMBO J. 21, 5875-5885.

Zuker, M. (2003). Mfold web server for nucleic acid folding and hybridization prediction. Nucleic Acids Res. 31, 3406-3415.

BACKGROUND OF INVENTION

1. Field of the Invention

The present invention relates to a group of bioinformatically detectable novel oligonucleotides, here identified as Genomic Address Messenger or GAM oligonucleotides, which are believed to be related to the micro RNA (miRNA) group of oligonucleotides.

2. Description of Prior Art

Micro RNAs (miRNA), are short ~22 nt non-coding regulatory RNA oligonucleotides, found in a wide range of species, believed to function as specific gene translation repressors, sometimes involved in cell-differentiation.

The ability to detect novel miRNAs is limited by the methodologies used to detect such oligonucleotides. All miRNAs identified so far either present a visibly discernable whole body phenotype, as do Lin-4 and Let-7 (Wightman, B., Ha, I., and Ruvkun, G., Cell 75:855-862 (1993); Reinhart et al. Nature 403: 901-906 (2000)), or produce sufficient quantities of RNA so as to be detected by the standard molecular biological techniques.

Studies reporting miRNAs (Lau et al., Science 294:858-862 (2001), Lagos-Quintana et al., Science 294: 853-858 (2001)) discovered 93 miRNAs in several species, by sequencing a limited number of clones (300 by Lau and 100 by Lagos-Quintana) of small segments (i.e. size fractionated) RNA. MiRNAs detected in these studies therefore, represent the more prevalent among the miRNA oligonucleotide family, and can not be much rarer than 1% of all small ~20 nt-long RNA oligonucleotides.

The aforesaid studies provide no basis for detection of miRNA oligonucleotides which either do not present a visually discernable whole body phenotype, or are rare (e.g. rarer than 0.1% of all size fractionated ~20 nt-long RNA segments expressed in the tissues examined), and therefore do not produce significant enough quantities of RNA so as to be detected by standard biological techniques.

Previous studies on miRNAs and their relation to diseases have suggested potential involvement of several miRNAs in various type of cancers; It has been suggested that mir-15 and mir-16 are associated with B-cell chronic lymphocytic leukemia (Calin, G. A at al., Proc. Natl. Acad. Sci. U.S.A., 2002). More recently, researchers have shown strong evidence for involvement of mir-143 and mir-145 in colorectal neoplasia (Michael, M. Z. et al., Mol. Cancer Res. 1: 882-891 (2003)). Mietzler and colleagues have demonstrated that mir-155, which is located on BIC locus, is highly and differentially expressed in pediatric Burkit lymphoma patients (Metzler, M. at al. Cancer 39: 167-169 (2004)). Involvement of miRNAs in Alzheimers disease is unknown.

The following U.S. patents relate to bioinformatic detection of genes: U.S. Pat. No. 6,369,195, entitled "Prostate-specific gene for diagnosis, prognosis and management of prostate cancer", and U.S. Pat. No. 6,291,666 entitled "Spike tissue-specific promoter", each of which is hereby incorporated by reference herein.

BRIEF DESCRIPTION OF SEQUENCE LISTING, LARGE TABLES AND COMPUTER PROGRAM LISTING

LENGTHY TABLES

The patent contains a lengthy table section. A copy of the table is available in electronic form from the USPTO web site (http://seqdata.uspto.gov/?pageRequest=docDetail&DocID=US07906326B2). An electronic copy of the table will also be available from the USPTO upon request and payment of the fee set forth in 37 CFR 1.19(b)(3).

A sequence listing in accordance with 37 C.F.R. §§1.821-1.825 is attached to the present invention and contained in a file named "SeqList.txt" (1222 KB, created Sep. 24, 2008), and is hereby incorporated by reference.

Large tables relating to genomic sequences are attached to the present application, appear in 11 table files (size, creation date), incorporated herein: TABLE1.TXT (215 KB, 16 Feb. 2004); TABLE2.TXT (16,358 KB, 16 Feb. 2004); TABLE3.TXT (134 KB, 16 Feb. 2004); TABLE4.TXT (945 KB, 16 Feb. 2004), TABLE5.TXT (113 KB, 16 Feb. 2004), TABLE6.TXT (189 KB, 16 Feb. 2004) and TABLE7.TXT (3,335 KB, 16 Feb. 2004), TABLE8.TXT (12,240 KB, 16 Feb. 2004), TABLE9.TXT (34,018 KB, 16 Feb. 2004), TABLE10.TXT (1,300 KB, 16 Feb. 2004) and TABLE11.TXT (2 KB, 16 Feb. 2004), all of which are incorporated by reference herein.

A computer program listing of a computer program constructed and operative in accordance with a preferred embodiment of the present invention is enclosed on an electronic medium in computer readable form, and is hereby incorporated by reference herein The computer program listing is contained in 6 files, the name, sizes and creation date of which are as follows: AUXILARY_FILES.TXT (117K, 14 Nov. 2003); BINDING_SITE_SCORING.TXT (17K, 14 Nov. 2003); EDIT_DISTANCE.TXT (144K, 24 Nov. 2003); FIRST-K.TXT (96K, 24 Nov. 2003); HAIRPIN_PREDICTION.TXT (47K, 14 Nov. 2003); TWO_PHASED_SIDE_SELECTOR.TXT (4K, 14 Nov. 2003); and TWO_PHASED_ PREDICTOR.TXT (74K, 14 Nov. 2003).

SUMMARY OF INVENTION

The present invention relates to an isolated nucleic acid selected from the group consisting of (a) SEQ ID NO: 6527, (b) a DNA encoding the nucleic acid of (a), wherein the DNA is identical in length to (a); and (c) the complement of (a) or (b), wherein the complement is identical in length to the nucleic acid of (a) or (b). Additionally, the present invention relates to vectors or probes comprising a human insert, wherein the human insert consists of the nucleic acid selected from the group consisting of (a) SEQ ID NO: 6527, (b) a DNA encoding the nucleic acid of (a), wherein the DNA is identical in length to (a); and (c) the complement of (a) or (b), wherein the complement is identical in length to the nucleic acid of (a) or (b), and wherein the vector or probe comprises no other insert but the nucleic acid as described above.

The present invention also relates to an isolated nucleic acid selected from the group consisting of (a) SEQ ID NO: 15, (b) a DNA encoding the nucleic acid of (a), wherein the DNA is identical in length to (a); and (c) the complement of (a) or (b), wherein the complement is identical in length to the nucleic acid of (a) or (b). Additionally, the present invention relates to vectors or probes comprising a human insert, wherein the human insert consists of the nucleic acid selected from the group consisting of (a) SEQ ID NO: 15, (b) a DNA encoding the nucleic acid of (a), wherein the DNA is identical in length to (a); and (c) the complement of (a) or (b), wherein the complement is identical in length to the nucleic acid of (a) or (b), and wherein the vector or probe comprises no other insert but the nucleic acid as described above.

BRIEF DESCRIPTION OF DRAWINGS

FIGS. 2, 3 and 4 are schematic diagrams which, when taken together, provide an analogy that illustrates a conceptual model of the present invention, addressing the genomic differentiation enigma;

FIGS. 5A and 5B are schematic diagrams, which when taken together, illustrate a 'genomic records' concept of the conceptual model of the present invention, addressing the genomic differentiation enigma;

FIG. 21B is a table summarizing laboratory validation results which validate efficacy of a bioinformatic oligonucleotide detection system constructed and operative in accordance with a preferred embodiment of the present invention;

FIG. 22A and FIG. 22B are a picture and a summary table of laboratory results validating the expression of 43 novel oligonucleotides detected by a bioinformatic oligonucleotide detection engine constructed and operative in accordance with a preferred embodiment of the present invention, thereby validating the efficacy of the oligonucleotide detection engine of the present invention;

FIG. 24A, is an annotated sequence of EST72223 (SEQ ID NO: 7414) comprising known miRNA oligonucleotide MIR98 and novel oligonucleotide GAM25 PRECURSOR detected by the oligonucleotide detection system of the present invention. Additionally annotated in EST72223 are the miRNA-98 hairpin in bold (SEQ ID NO: 7415), the sequence of the mature miRNA-98 in bold and underline (SEQ ID NO: 7416), the sequence of the GAM25 hairpin in bold (SEQ ID NO: 7417), and the sequence of the mature miRNA of GAM25 in bold and underline (SEQ ID NO: 7418).

FIGS. 24B, 24C and 24D are pictures of laboratory results, which when taken together demonstrate laboratory confirmation of expression of known oligonucleotide MIR98 and of novel bioinformatically detected GAM25 RNA respectively, both of FIG. 24A, thus validating the bioinformatic oligonucleotide detection system of the present invention.

BRIEF DESCRIPTION OF SEQUENCES

A Sequence Listing of genomic sequences of the present invention designated SEQ ID NO: 1 through SEQ ID NO: 7,351 is attached to this application, and is hereby incorporated herein. The genomic listing comprises the following nucleotide sequences: nucleotide sequences of 1708 GAMs precursors of respective novel oligonucleotides of the present invention; nucleotide sequences of 2686 GAM RNA oligonucleotides of respective novel DNA oligonucleotides of the present invention; and nucleotide sequences of 2957 target gene binding sites of respective novel oligonucleotides of the present invention.

DETAILED DESCRIPTION

Figure 1:
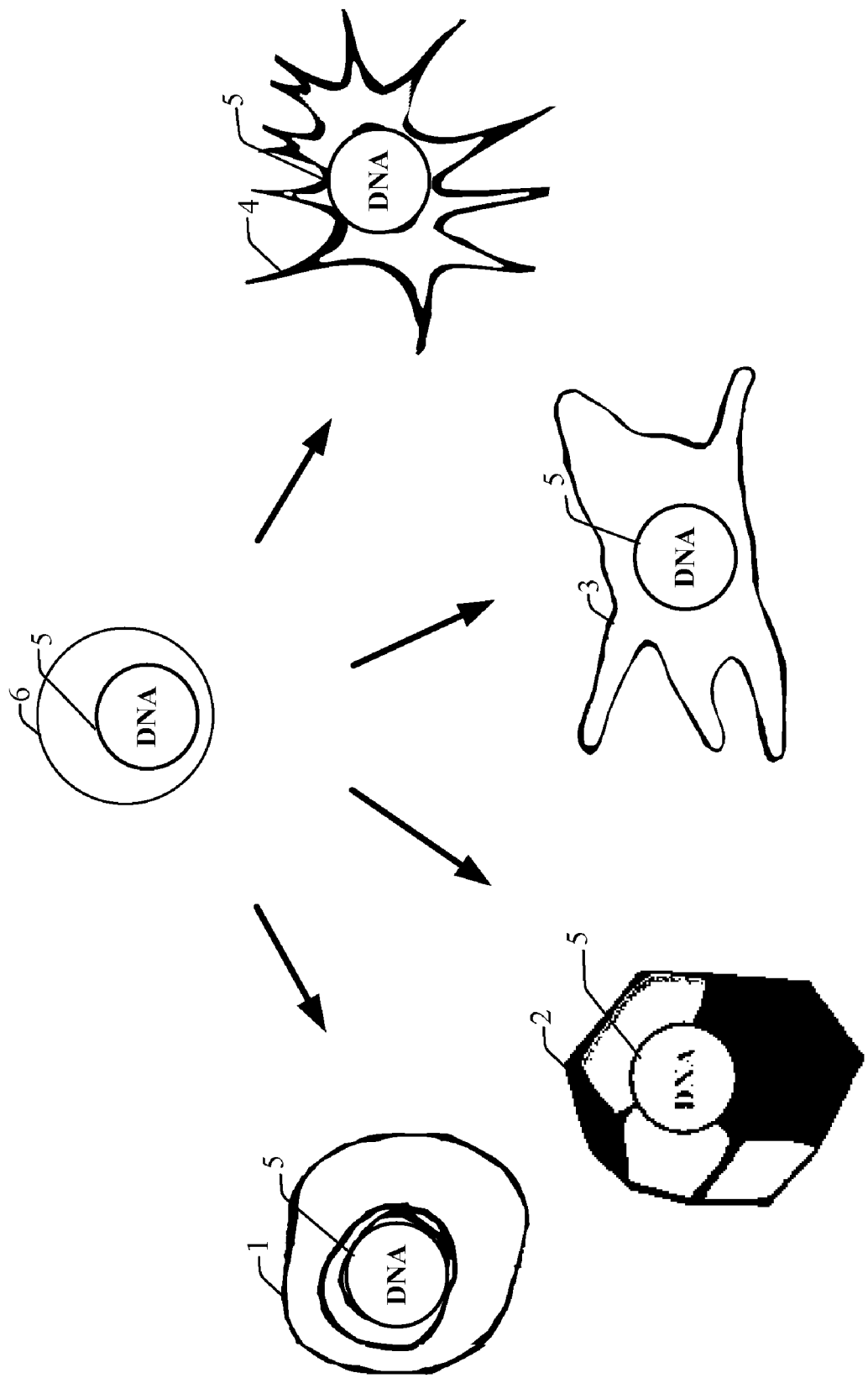
FIG. 1 is a simplified diagram illustrating a genomic differentiation enigma that the present invention addresses.

Reference is now made to FIG. 1 which is a simplified diagram providing a conceptual explanation of a genomic differentiation enigma, which the present invention addresses, inter alia.

FIG. 1 depicts various types of cells in an organism, such as a cartilage cell designated by reference numeral 1, a liver cell designated by reference numeral 2, a fibroblast cell designated by reference numeral 3, and a bone cell designated by reference numeral 4, all containing identical DNA designated by reference numeral 5. Notwithstanding that the various types of cells are all derived from an initial fertilized egg cell designated by reference numeral 6, each of these cells expresses different proteins and accordingly acquires a different shape and function.

The present invention proposes inter alia that the inevitable conclusion from the foregoing is, however, strikingly simple: The genome must contain a modular differentiation coding system. The genome of each cell must include multiple modules or records, possibly a different one for each cell type, as well as a mechanism causing each cell at its inception to be instructed which one of the multiple records governs its behavior.

This modular code concept may be somewhat difficult to grasp, since most persons are accustomed to view things from an external viewpoint. An architect, for example, looks at a plan of a building, which details exactly where each element (block, window, door, electrical switch, etc.) is to be placed relative to all other elements, and, using the plan, instructs builders to place these elements in their designated places. This is an example of an external viewpoint: The architect is external to the plan, which itself is external with respect to the physical building, and with respect to its various elements. The architect may therefore act as an "external organizing agent": seeing the full picture and the relationships between all elements, and being able to instruct from the outside where to place each of them.

According to a preferred embodiment of the present invention, genomic differentiation coding works differently, without any such external organizing agent. It comprises a smart block (the first cell), which is the architect and the plan, and which continuously duplicates itself, somehow knowing when to manifest itself as a block and when as a window, door, or electrical switch.

Reference is now made to FIGS. 2A-4 which are schematic diagrams which, when taken together, provide an analogy that illustrates a conceptual model of the present invention, addressing the genomic differentiation enigma.

Reference is now made to FIG. 2A. An imaginary talented chef, designated by reference numeral 7, is capable of preparing any meal provided that he is given specific written cooking instructions. This chef 7 is equipped with two items: (a) a thick recipe book, designated by reference numeral 8, and (b) a small note, designated by reference numeral 9, having a number scribbled on it. The recipe book 8 comprises multiple pages, each page detailing how to prepare a specific meal. The small note 9 indicates the page to be opened, and therefore the meal to be prepared. The chef looks at the page number written on the note, opens the recipe book to the appropriate page, and prepares the meal according to the written instructions on this page. In the example shown in FIG. 2A, the chef 7 is holding a small note 9 bearing the number 127. He therefore opens the book to page 127, as designated by reference numeral 10. Since this page contains the recipe for preparing bread, the chef 7 prepares a loaf of bread, designated by reference numeral 12. Pages of the book, such as page 10 in the example shown in FIG. 2A, contains additional information, designated by reference numeral 11 which additional data is further elaborated hereinbelow with reference to FIGS. 3 and 4.

Reference is now made to FIG. 2B, which depicts two identical chefs, a first chef, designated by reference numeral 13, and a second chef, designated by reference numeral 14, both holding an identical recipe book, designated by reference numeral 8. Although the first chef 13 and the second chef 14 are identical, and hold identical recipe books 8, they differ in that they hold different small notes: the first chef 13 holds a small note designated by reference numeral 9, having the number 127 written on it, whereas the second chef 14 holds a small note designated by reference numeral 15, having the number 134 written on it. Accordingly, the first chef 13 opens the book 8 to page 127, as designated by reference numeral 10 and, based on the instructions written on page 127 prepares a loaf of bread, designated by reference numeral 12. The second chef 14 opens the book 8 to page 134, as designated by reference numeral 16 and, based on the instructions written on page 134, prepares a pie, designated by reference numeral 17. Pages in the book, such as pages 10 and 16 in the examples shown in FIG. 2B, contain additional information, designated by reference numeral 11 which additional information is further elaborated hereinbelow with reference to FIGS. 3 and 4.

Figure 3:
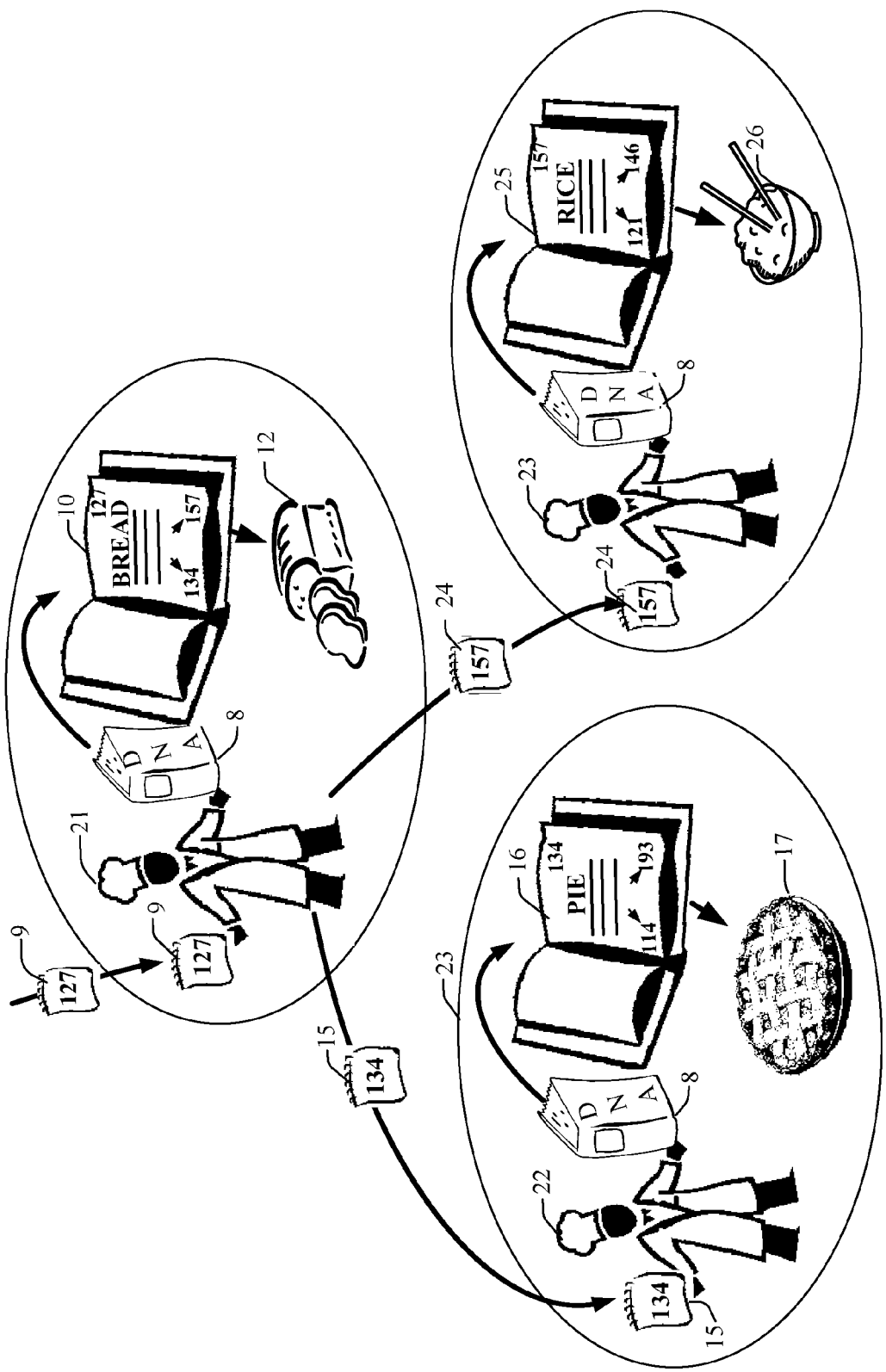

Reference is now made to FIG. 3 which illustrates a mode by which an imaginary chef can duplicate himself yielding two identical chefs, instructing each of the identical duplicate chefs to prepare a different meal. As an example, FIG. 3 shows chef 21 duplicating himself, yielding two duplicate chefs: a first duplicate chef designated by reference numeral 22 and a second duplicate chef designated by reference numeral 23. The duplicate chefs are identical to each other and to chef 21.

Like chefs 7 and 13 (FIGS. 2A and 2B), FIG. 3 shows chef 21 holding a recipe book 8 and receiving a note 9 bearing the number 127. The chef 21 therefore opens the book 8 to page 127, as designated by reference numeral 10, and prepares a loaf of bread 12. However, FIG. 3 also elaborates some of the additional information 11 (FIGS. 2A and 2B) found in page 10: the bottom of page 10, bears two numbers, 134 and 157.

Chef 21 is trained to perform the following three actions when he is finished preparing a meal: (a) Duplicate himself yielding two duplicate chefs, the first duplicate chef 22 and the second duplicate chef 23; (b) Duplicate his recipe book 8, handing an identical copy to each of the duplicate chefs 22 and 23; and (c) Write down the numbers found at the bottom of the page he was instructed to open the book to. In the example of chef 21, since he was instructed to open the book to page 10, he writes the numbers 134 and 157 on two respective notes designated by reference numerals 15 and 24, and hands note 15 bearing the number 134 to the first duplicate chef 22 and note 24 bearing the number 157 to the second duplicate chef 23.

Accordingly, the first duplicate chef 22 receives note 15 bearing the number 134 and therefore opens the recipe book 8 to page 134, as designated by reference numeral 16, and prepares a pie, designated by reference numeral 17. The second duplicate chef 23 receives note 24 bearing the number 157 and therefore opens the recipe book 8 to page 157, as designated by reference numeral 25, and prepares rice, designated by reference numeral 26.

It is appreciated that while chef 21 and duplicate chefs 22 and 23 are identical and hold identical recipe books 8, they each prepare a different meal. It is also appreciated that the meals prepared by the first duplicate chef 22 and the second duplicate chef 23 are determined by chef 21, and are mediated by the differently numbered notes 15 and 24 passed on from chef 21 to duplicate chefs 22 and 23 respectively.

It is further appreciated that the mechanism illustrated by FIG. 3 enables an unlimited lineage of chefs to divide into duplicate, identical chefs and to determine the meals those duplicate chefs would prepare. As an example, since the first duplicate chef 22 is directed to page 134, as designated by reference numeral 16, when he duplicates himself (not shown), he will instruct his two duplicate chefs to prepare meals specified on pages the numbers of which are written at the bottom of page 134, i.e. pages 114 and 193 respectively. Similarly, the second duplicate chef 23 will instruct its duplicate chefs to prepare meals specified on pages 121 and 146 respectively, etc.

Figure 4:
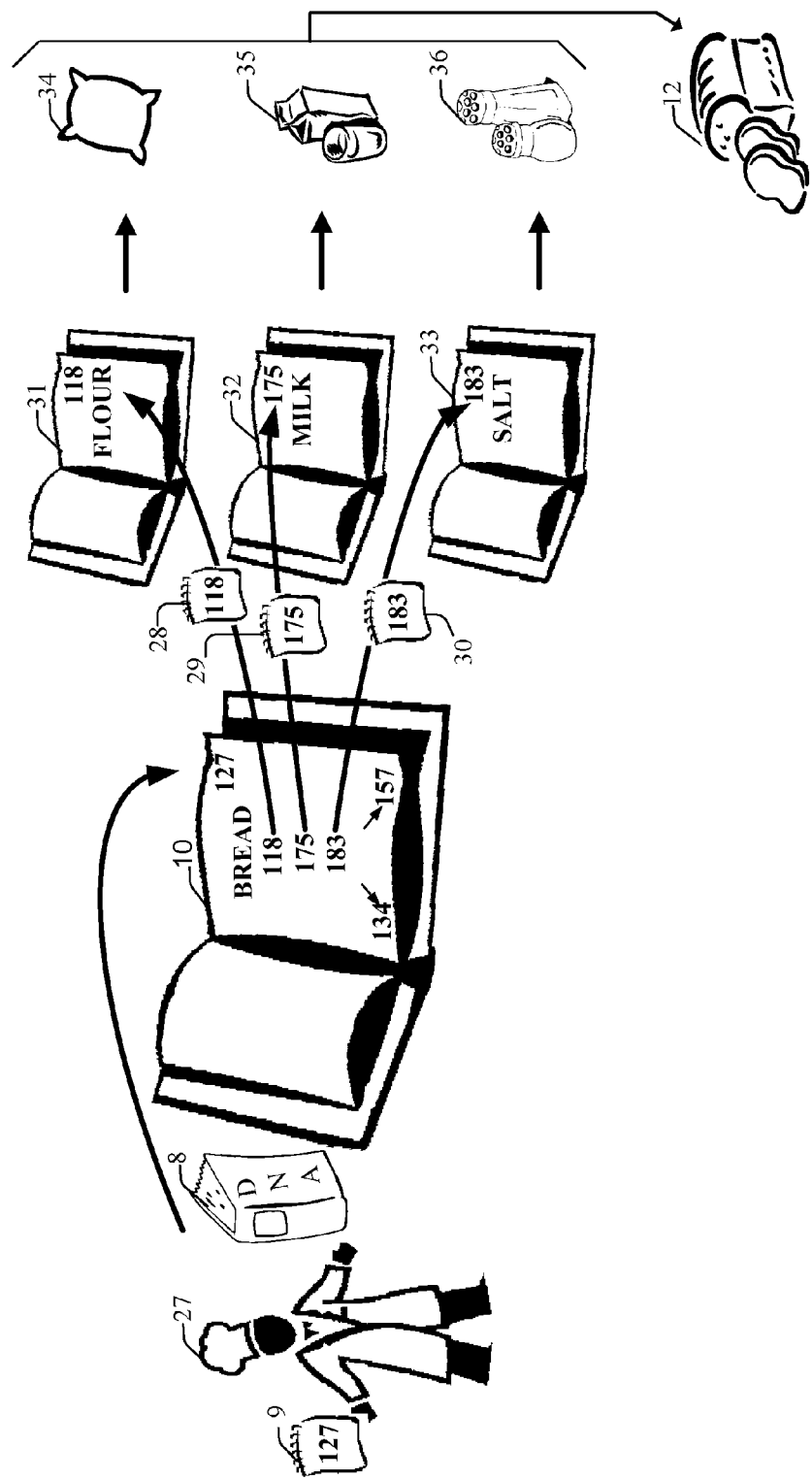

Reference is now made to FIG. 4, which illustrates a mode by which a chef can prepare a meal based on instructions written in a shorthand format: The main meal-page to which a chef is directed by a small note he is given, merely contains a list of numbers which further direct him to other pages, each specifying how to prepare an ingredient of that meal.

To illustrate this shorthand format FIG. 4 shows a chef, designated by reference numeral 27, holding the recipe book 8 and the note 9 which bears the number 127. The chef 27 accordingly opens the recipe book 8 to page 127, as designated by reference numeral 10, and based on instructions on this page prepares bread 12. This is similar to chefs 7, 13 and 21 of FIGS. 2A, 2B and 3 respectively.

However, FIG. 4 also further elaborates some of the additional information 11 (FIGS. 2A and 2B) found in page 10. FIG. 4 shows the cooking "instructions" found on page 10 for making bread 12 written in a shorthand format, comprising only three numbers, 118, 175 and 183. The chef 27 writes these numbers on three respective notes designated by reference numerals 28-30. The notes 28-30 are then used to turn to corresponding pages 31-33 of the book 8, which pages provide instructions for preparation of ingredients required for making bread 12: flour 34, milk 35 and salt 36.

The analogy provided by FIGS. 2A-4 illustrates the conceptual model of the present invention addressing the genomic differentiation enigma, and may be explained as follows: The chefs and duplicate chefs 7, 13, 14, 21-23 and 27

(FIGS. 2A-4) in the given analogy represents cells. The thick recipe book 8 represents the DNA 5 (FIG. 1). Preparing meals such as bread 12, pie 17 or rice 16 (all of FIG. 3) represent the cell manifesting itself as a specific cell-type, such as cartilage cell 1, liver cell 2, fibroblast cell 3, and bone cell 4 (all of FIG. 1). Ingredients of a meal, such as flour 34, milk 35 and salt 36 (all of FIG. 4), represent proteins typically expressed by a cell of a certain cell-type, such as 1-4. Like the different chefs of the analogy, having the same thick recipe book 8 yet preparing different meals, so do different cells in an organism contain the same DNA 5 yet manifest themselves as different cell types, such as 1-4, expressing proteins typical of these respective cell types. Application of analogy of FIGS. 2A-4 to cell-biology is further described hereinbelow with reference to FIGS. 5A-7.

Figure 5A:
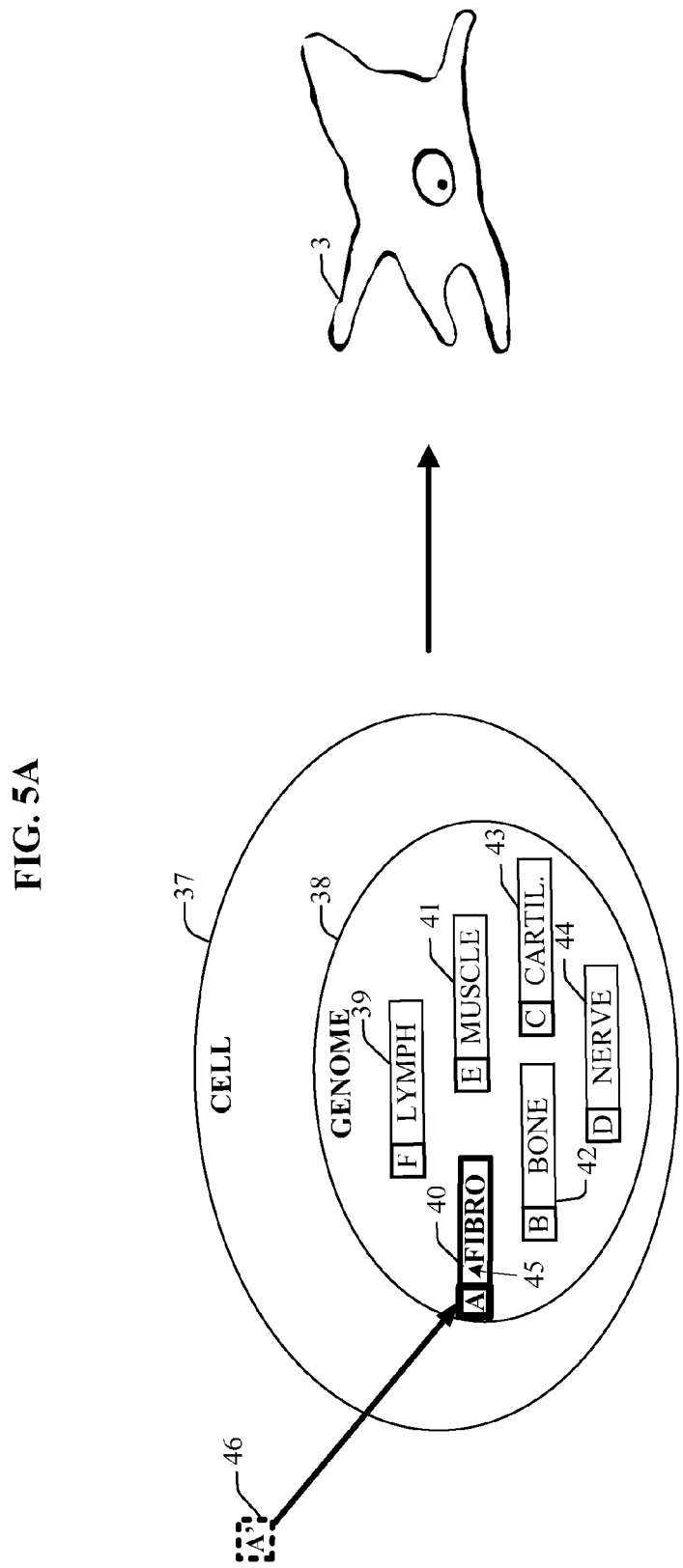

Reference is now made to FIGS. 5A and 5B which are schematic diagrams, which when taken together illustrate a Genomic Records concept of the present invention, addressing the genomic differentiation enigma. FIGS. 5A and 5B correspond to FIGS. 2A and 2B of the chef analogy described hereinabove.

An important aspect of the present invention is the Genomic Records concept. According to a preferred embodiment of the present invention the DNA (the thick recipe book 8 in the illustration) comprises a very large number of Genomic Records (analogous to pages, such as 10, 16 and 25, in the recipe book) containing the instructions for differentiation of a different cell-type, or developmental process. Each Genomic Record comprises by a very short genomic sequence which functions as a "Genomic Address" of that Genomic Record (analogous to a page number, such as the numbers 127, 134 and 157 appearing in FIG. 3, in the recipe book). At its inception, in addition to the DNA, each cell also receives a short RNA segment (the scribbled short note, such as 9, 15, 24 of FIG. 3 in the illustration). This short RNA segment binds complementarily to a "Genomic Address" sequence of one of the Genomic Records, thereby modulating expression of that Genomic Record, and accordingly determining the cell's-fate (analogous to opening the recipe book 8 to a page corresponding to a number on the scribbled note, thereby determining the meal to be prepared). A Genomic Record may also comprise multiple short RNA segments each of which binds complementarily to a target protein coding gene, thus modulating expression of this target gene (analogous to the shorthand format whereby a page, such as 10, points to other pages, such as 31-33, encoding various ingredient, such as 34, 35 and 36, all of FIG. 4).

Reference is now made to FIG. 5A. FIG. 5A illustrates a cell 37, having a genome 38. The genome 38 comprises a plurality of Genomic Records, some of which Genomic Records correlate to specific cell-types. As an example, 6 such genomic records are shown, corresponding to 6 cell-types: LYMPH genomic record 39, FIBROBLAST genomic record 40, MUSCLE genomic record 41, BONE genomic record 42, CARTILAGE genomic record 43 and NERVE genomic record 44. Each genomic record comprises genomic instructions on differentiation into a specific cell-type, as further elaborated hereinbelow with reference to FIG. 7. At cell inception, the cell 37 receives a maternal short RNA segment 46, which activates one of the genomic records, causing the cell to differentiate according to the instructions this genomic record comprises. As an example FIG. 5A illustrates reception of a maternal short RNA segment designated 46 having a nucleotide sequence herein symbolically represented by A'.

The FIBROBLAST genomic record 40 contains a binding site having a nucleotide sequence symbolically represented by A, which is complementary to the nucleotide sequence of A', and therefore the short RNA segment 46 binds to the FIBROBLAST genomic record 40. This binding activates the FIBROBLAST genomic record, causing the cell 37 to differentiate into a fibroblast cell-type 3 (FIG. 1). Other genomic records, designated by reference numerals 39 and 41-44, comprise binding sites having nucleotide sequences that are symbolically represented by F, E, B, C and D, which are not complementary of the nucleotide sequence of the short RNA segment 46, and are therefore not activated thereby. Genomic Records, such as the FIBROBLAST genomic record 40 contain additional information, designated by reference numeral 45, which is further elaborated hereinbelow with reference to FIGS. 6 and 7.

Reference is now made to FIG. 5B, which is a simplified schematic diagram, illustrating cellular differentiation mediated by the "Genomic Records" concept. FIG. 5B depicts 2 cells in an organism, CELL A designated by reference numeral 47 and CELL B designated by reference numeral 48, each having a genome 38. It is appreciated that since CELL A 47 and CELL B 48 are cells in the same organism, the genome 38 of cells 47 and 48 is identical. Despite having an identical genome 38, CELL A 47 differentiates differently from CELL B 48, due to activation of different genomic records in these two cells. In CELL A 47 the FIBRO GENOMIC RECORD 40 is activated, causing CELL A 47 to differentiate into a FIBROBLAST CELL 3, whereas in CELL B 48 the BONE GENOMIC RECORD 42 is activated, causing the CELL B 48 to differentiate into a BONE CELL 4 (FIG. 1). The cause for activation of different genomic records in these two cells is the different maternal short RNA which they both received: CELL A 47 received a maternal short RNA segment designated 46 bearing a nucleotide sequence represented by A' activating genomic record FIBRO 40, whereas CELL B 48 received a maternal short RNA segment designated 49 bearing a nucleotide sequence represented by B' activating genomic record BONE 42.

Figure 6:
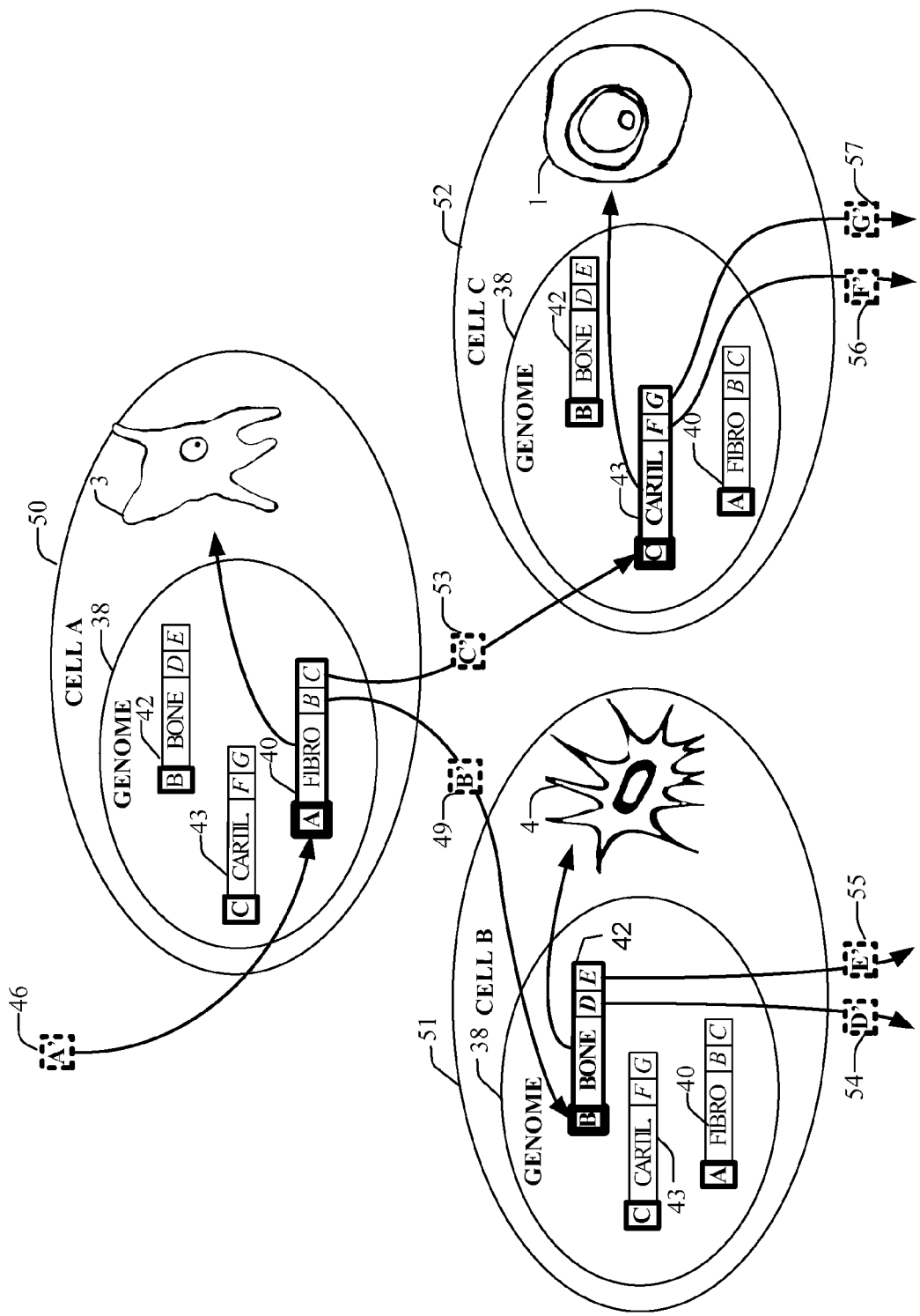
FIG. 6 is a schematic diagram illustrating a 'genomically programmed cell differentiation' concept of the conceptual model of the present invention, addressing the genomic differentiation enigma.

Reference is now made to FIG. 6 which is a schematic diagram illustrating a "genomically programmed cell differentiation" concept of the conceptual model of the present invention, addressing the genomic differentiation enigma.

A cell designated CELL A 50 divides into 2 cells designated CELL B 51 and CELL C 52. CELL A 50, CELL B 51 and CELL C 52 each comprise a GENOME 38, which GENOME 38 comprises a plurality of GENOMIC RECORDS, herein exemplified by reference numerals 40, 42 and 43. It is appreciated that since CELL A 50, CELL B 51 and CELL C 52 are cells in the same organism, the GENOME 38 of these cells, and the GENOMIC RECORDS, exemplified by 40, 42 and 43, the genome of these cells comprises, are identical in these cells.

As described above with reference to FIG. 5B, at its inception, CELL A 50 receives a maternal short RNA segment, designated by reference numeral 46, having a nucleotide sequence represented by A' and outlined by a broken line, which activates the FIBRO genomic record 40, thereby causing CELL A 50 to differentiate into a FIBROBLAST CELL 3. However, FIG. 6 elaborates some of the additional information 45 (FIG. 5A) of the genomic records: Genomic record may also comprise two short genomic sequences, referred to here as Daughter Cell Genomic Addresses. Blocks designated B and C are Daughter Cell Genomic Addresses of the FIBRO Genomic Record. At cell division, each parent cell transcribes two short RNA segments, corresponding to the two Daughter Cell Genomic Addresses of the Genomic Record of that parent cell, and transfers one to each of its two daughter cells. CELL A 50 transcribes and transfers to its two daughter cells 51 and 52, two short RNA segments, designated by reference numerals 49 and 53, outlined by a broken line and designated B' and C', corresponding to daughter cell genomic addresses designated B and C comprised in the FIBRO genomic record 40.

CELL B 51 therefore receives the above mentioned maternal short RNA segment designated 49 having a nucleotide sequence represented by B', which binds complementarily to genomic address designated B of the BONE genomic record 42, thereby activating this genomic record, which in turn causes CELL B 51 to differentiate into a BONE CELL 4. Similarly, CELL C 52 receives the above mentioned maternal short RNA segment designated 53 having a nucleotide sequence represented by C', which binds complementarily to genomic address designated C of a CARTILAGE genomic record 43, thereby activating this genomic record, which in turn causes CELL C 52 to differentiate into a CARTILAGE CELL 1 (FIG. 1).

It is appreciated that the mechanism illustrated by FIG. 6 enables an unlimited lineage of cells to divide into daughter cells containing the same DNA 5 (FIG. 1), and to determine the cell-fate of these daughter cells. For example, when CELL B 51 and CELL C 52 divide into their respective daughter cells (not shown), they will transfer short RNA segments designated by reference numerals 54-57, to their respective daughter cells. The cell fate of each of these daughter cells is effected by the identity of the maternal short RNA segments 54-57 they each receive, which in turn determine the genomic record activated.

Figure 7:
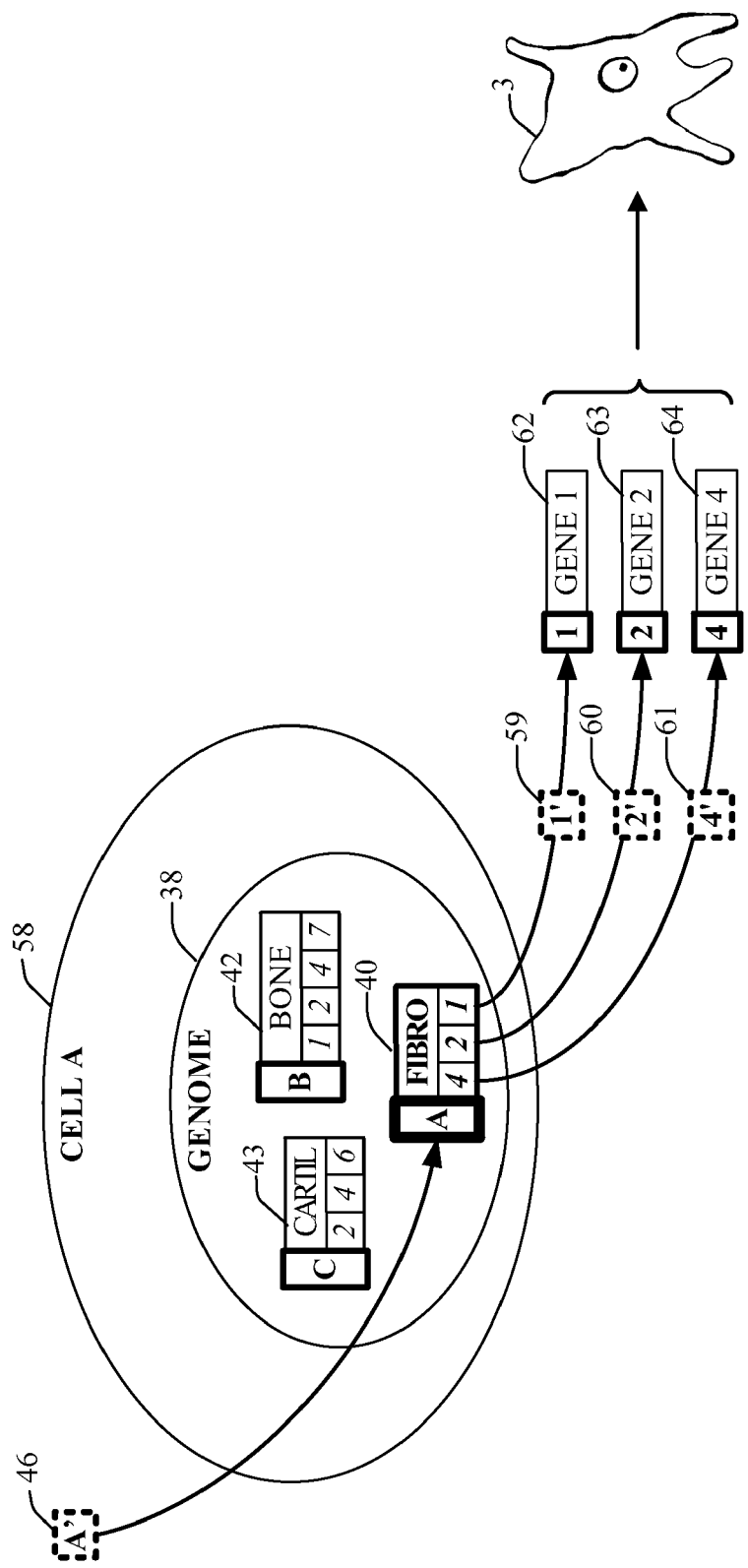
FIG. 7 is a schematic diagram illustrating a 'genomically programmed cell-specific protein expression modulation' concept of the conceptual model of the present invention, addressing the genomic differentiation enigma.

Reference is now made to FIG. 7 which is a schematic diagram illustrating a "genomically programmed cell-specific protein expression modulation" concept of the conceptual model of the present invention, addressing the genomic differentiation enigma.

Cell A 58 receives a maternal short RNA segment designated 46 having a nucleotide sequence represented by A' which activates the FIBROBLAST genomic record 40, by complementarily binding to a binding site this genomic record comprises, the nucleotide sequence of which binding site is designated A. This is similar to the process shown in FIG. 5A. However, FIG. 7 further elaborates some of the additional information 45 (FIG. 1). The FIBROBLAST genomic record 40 comprises 3 short nucleotide segments, having nucleotide sequences symbolically represented by 1, 2 and 4 respectively, which encode 3 respective short RNA oligonucleotides, designated by reference numerals 59-61. Each of these short RNA oligonucleotides modulates expression of a respective one of the target genes GENE 1, GENE 2 and GENE 4, designated by reference numerals 62-64 respectively, by complementarily binding to a binding site sequence associated with that target gene. In a preferred embodiment of the present invention, the modulation of expression of target genes such as 62-64 comprises translation inhibition of target genes by complementarily binding to binding sites located in untranslated regions of the target genes. Modulation of expression of these genes results in CELL A 58 differentiating into a FIBROBLAST cell-type 3 (FIG. 1).

It is appreciated that the concept of genomic records each comprising a cluster of short RNA segments, which segments modulate expression of target genes thereby modulating differentiation, is compatible with the clusters of miRNA oligonucleotides of the present invention, and their translational inhibition of respective target genes by means of complementarily binding to binding sites located in the untranslated regions of mRNA of these target genes.

Figure 8:
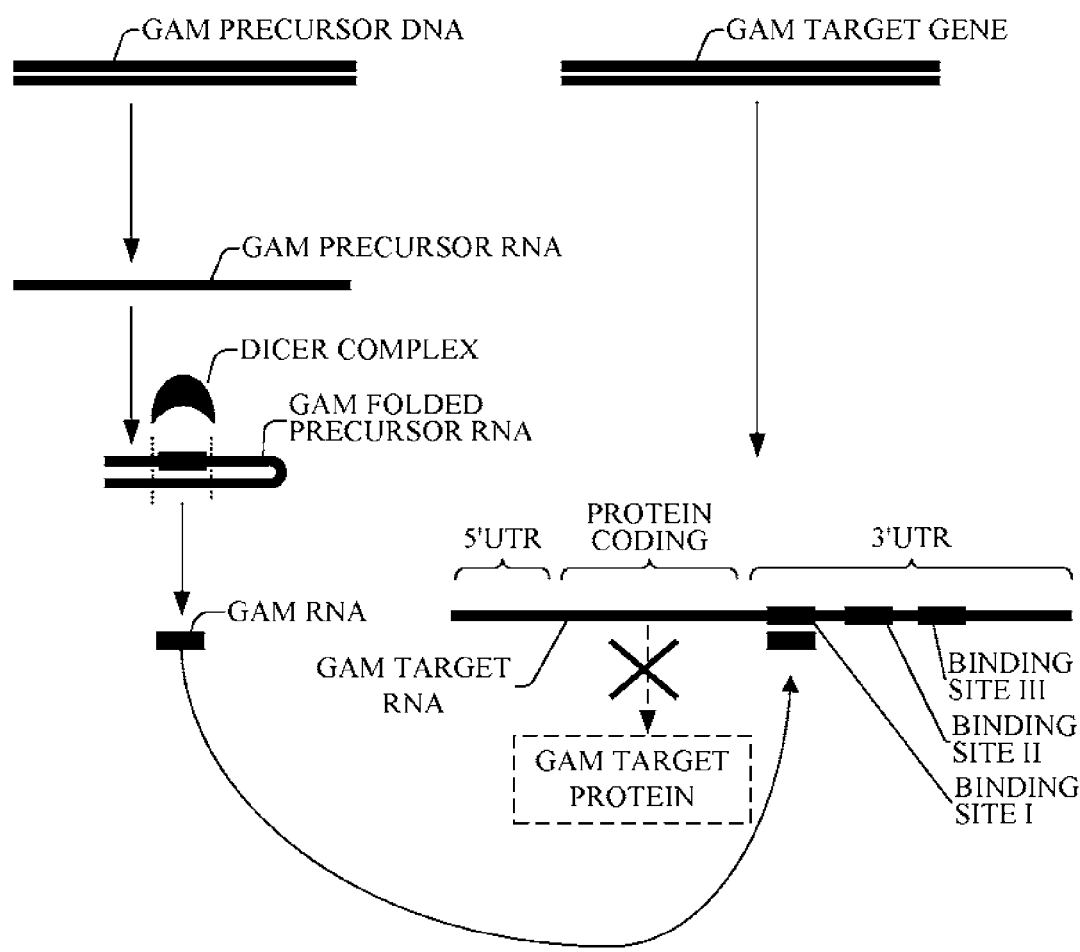
FIG. 8 is a simplified diagram illustrating a mode by which an oligonucleotide of a novel group of oligonucleotides of the present invention, modulates expression of known target genes.

Reference is now made to FIG. 8, which is a simplified diagram describing how a plurality of novel bioinformatically detectable oligonucleotides of the present invention, referred to here as Genomic Address Messenger (GAM) oligonucleotides, modulate expression of respective target genes.

GAM oligonucleotides are novel, bioinformatically detectable, regulatory, non protein coding, micro RNA (miRNA)-like oligonucleotides. The method by which GAMs are detected is described hereinbelow with additional reference to FIGS. 9-15.

GAM PRECURSOR DNA is encoded by the human genome. GAM TARGET GENE is a human gene encoded by the human genome.

GAM PRECURSOR DNA encodes a GAM PRECURSOR RNA. Similar to miRNA oligonucleotides, GAM PRECURSOR RNA does not encode a protein. GAM PRECURSOR RNA folds onto itself, forming GAM FOLDED PRECURSOR RNA, which has a two-dimensional 'hairpin structure'. As is well known in the art, this 'hairpin structure', is typical of by miRNA precursor oligonucleotides, and is due to the fact that the nucleotide sequence of the first half of the miRNA precursor oligonucleotide is a fully or partially complementary sequence of the nucleotide sequence of the second half thereof. By complementary is meant a sequence which is reversed and wherein each nucleotide is replaced by a complementary nucleotide, as is well known in the art (e.g. ATGGC is the complementary sequence of GCCAT).

An enzyme complex comprising an enzyme called Dicer together with other necessary proteins, herein designated as the DICER COMPLEX, 'dices' the GAM FOLDED PRECURSOR RNA yielding a GAM RNA, in the form of a single stranded ~22 nt long RNA segment. The DICER COMPLEX is known in the art to dice a hairpin structured miRNA precursor, thereby yielding diced miRNA in the form of a short ~22 nt RNA segment.

GAM TARGET GENE encodes a corresponding messenger RNA, designated GAM TARGET RNA. GAM TARGET RNA comprises three regions, as is typical of mRNA of a protein coding gene: a 5' untranslated region, a protein coding region and a 3' untranslated region, designated 5'UTR, PROTEIN CODING and 3'UTR respectively.

GAM RNA binds complementarily (i.e. hybridizes) to one or more target binding sites located in untranslated regions of GAM TARGET RNA. This complementary binding is due to the fact that the nucleotide sequence of GAM RNA is a partial or fully complementary sequence of the nucleotide sequence of each of the target binding sites. As an illustration, FIG. 8 shows three such target binding sites, designated BINDING SITE I, BINDING SITE II and BINDING SITE III respectively. It is appreciated that the number of target binding sites shown in FIG. 8 is only illustrative and that any suitable number of target binding sites may be present. It is further appreciated that although FIG. 8 shows target binding sites only in the 3'UTR region, these target binding sites may be located instead in the 5'UTR region or in both 3'UTR and 5'UTR regions.

The complementary binding of GAM RNA to target binding sites on GAM TARGET RNA, such as BINDING SITE I, BINDING SITE II and BINDING SITE III, inhibits translation of GAM TARGET RNA into GAM TARGET PROTEIN, which is shown surrounded by a broken line.

It is appreciated that GAM TARGET GENE in fact represents a plurality of GAM target genes. The mRNA of each one of this plurality of GAM target genes comprises one or more target binding sites, each having a nucleotide sequence which is at least partly complementary to GAM RNA, and which when bound by GAM RNA causes inhibition of translation of the GAM target mRNA into a corresponding GAM target protein.

The mechanism of the translational inhibition exerted by GAM RNA on one or more GAM TARGET GENE, may be similar or identical to the known mechanism of translational inhibition exerted by known miRNA oligonucleotides.

The nucleotide sequence of the predicted human GAM RNA (miRNA) GAM1032, which is described by FIG. 8, and its respective genomic source and genomic location are set forth in Tables 1-3. Table 1 describes the predicted human GAM RNA (miRNA) as set forth in SEQ ID NO: 15.

TABLE 1

| GAM SEQ-ID | GAM NAME | GAM RNA SEQUENCE | GAM POS |
|---|---|---|---|
| 15 | GAM1032 | CTAGACTGAAGCTCCTTGAGGA | A |

Table 2 describes the GAM PRECURSOR RNA (hairpin) as set forth in SEQ ID NO: 6527 and how it relates to FIG. 8.

TABLE 2

| GAM NAME | PRECUR SEQ-ID | PRECURSOR SEQUENCE | GAM DESCRIPTION |
|---|---|---|---|
| GAM1032 | 6527 | GCTAGTCACT GGGGCAAAGA TGACTAAAAC ACTTTTCCTG CCCTCGAGGA GCTCACAGTC TAGTATGTCT CATCCCCTAC TAGACTGAAG CTCCTTGAGG ACAGGGATGG TCATACTCAC CTCGGTGTTG C | FIG. 8 further provides a conceptual description of another novel bioinformatically detected oligonucleotides of the present invention, referred to here as Genomic Address Messenger 1032 (GAM1032) oligonucleotides modulates expression of respective target genes whose function and utility is known in the art GAM1032 is a novel bioinformatically detectable regulatory, non protein coding, micro RNA (miRNA)-like oligonucleotide. The method by which GAM1032 was detected is described with additional reference to FIGS. 9-15 GAM PRECURSOR DNA is encoded by the human genome. GAM TARGET GENE is a humen gene encoded by the human genome GAM1032 precursor DNA, herein designated GAM PRECURSOR DNA, encodes a GAM1032 precursor RNA, herein designated GAM PRECURSOR RNA. Similar to other miRNA genes GAM1032 precursor RNA does not encode a protein. A nucleotide sequence identical or highly similar to the nucleotide sequence of GAM1032 precursor RNA is designated SEQ ID: 6527, and is provided hereinbelow with reference to the sequence listing part. Nucleotide sequence SEQ ID: 6527 is located from position 141427052 to position 141427182 relative to chromosome 8 on the '-' strand. GAM1032 precursor RNA folds onto itself, forming GAM1032 folded precursor RNA, herein designated GAM FOLDED PRECURSOR RNA, which has a two-dimensional hairpin structure. As is well known in the art, this hairpin structure, is typical of RNA encoded by miRNA genes, and is due to the fact that the nucleotide sequence of the first half of the RNA encoded by a |

TABLE 2-continued

| GAM NAME | PRECUR SEQ-ID | PRECURSOR SEQUENCE | GAM DESCRIPTION |
|---|---|---|---|
| | | | miRNA gene is a fully or partially complementary sequence of the nucleotide sequence of the second half thereof. Nucleotide sequence of GAM1032 precursor RNA, designated SEQ ID NO: 6527, and a schematic representation of a predicted secondary folding of GAM1032 folded precursor RNA, herein designated GAM FOLDED PRECURSOR RNA, are set forth in Tables 3 and 4 incorporated herein An enzyme complex designated DICER COMPLEX, 'dices' the GAM1032 folded precursor RNA yielding a GAM1032 RNA, herein designated GAM RNA, in the form of a single stranded ~22nt long RNA segment. As is known in the art, 'dicing' of a hairpin structured RNA precursor product to yield a short ~22nt RNA segment is catalyzed by an enzyme complex comprising an enzyme called Dicer RNase III together with other necessary proteins. Table 5 provides a nucleotide sequence that is highly likely to be identical or highly similar to the nucleotide sequence of GAM1032 RNA, hereby incorporated herein. Expression of GAM1032 RNA was experimentally validated in HeLa cells using the methods described with reference to FIGS.22 to 24 GAM1032 target gene, herein designated GAM TARGET GENE, encodes a corresponding messenger RNA, GAM1032 target RNA, herein designated GAM TARGET RNA.GAM1032 target RNA comprises three regions, as is typical of mRNA of a protein coding gene: a 5' untranslated region, a protein coding region and a 3'untranslated region, designated 5'UTR, PROTEIN CODING and 3'UTR respectively GAM1032 RNA, herein designated GAM RNA, binds complementarily to one or more target binding sites located in untranslated regions of GAM1032 target RNA, herein designated GAM TARGET RNA. This complementary binding is due to the fact that the nucleotide sequence of GAM1032 RNA is a partial or fully complementary sequence of the nucleotide sequence of each of the target binding sites. As an illustration, FIG. 8 shows three such target binding sites, designated BINDING SITE I, BINDING SITE II and BINDING SITE III respectively. It is appreciated that the number of target binding sites shown in FIG. 8 is only illustrative and that any suitable number of target binding sites may be present. It is further appreciated that although FIG. 8 shows target binding sites only in the 3'UTR region,these target binding sites may be located instead in the 5'UTR region or in both 3'UTR and 5'UTR region The complementary binding of GAM1032 RNA, herein designated GAM RNA, to target binding sites on GAM1032 target RNA, herein designated GAM TARGET RNA, such as BINDING SITE I, |

TABLE 2-continued

| PRECUR GAM NAME SEQ-ID | PRECURSOR SEQUENCE | GAM DESCRIPTION |
|---|---|---|
| | | BINDING SITE II and BINDING SITE III, inhibits translation of GAM1032 target RNA into GAM1032 target protein, herein designated GAM TARGET PROTEIN, which is shown surrounded by a broken line It is appreciated that GAM1032 target gene, herein designated GAM TARGET GENE, in fact represents a plurality of GAM1032 target genes. The mRNA of each one of this plurality of GAM1032 target genes comprises one or more target binding sites, each having a nucleotide sequence which is at least partly complementary to GAM1032 RNA, herein designated GAM RNA, and which when bound by GAM1032 RNA causes inhibition of translation of the GAM1032 target mRNA into a corresponding GAM1032 target protein. The mechanism of the translational inhibition exerted by GAM1032 RNA, herein designated GAM RNA, on one or more GAM1032 target genes, herein collectively designated GAM TARGET GENE, may be similar or identical to the known mechanism of translational inhibition exerted byknown miRNA genes Nucleotide sequence of GAM1032 precursor RNA, herein designated GAM PRECURSOR RNA, respective genomic sources and chromosomal locations and a schematic representation of a predicted secondary folding of GAM1032 folded precursor RNA, herein designated GAM FOLDED PRECURSOR RNA, are set forth in Tables 3 and 4, incorporated herein. Nucleotide sequences of a 'diced' GAM1032 RNA, herein designated GAM RNA, of GAM1032 folded precursor RNA, herein designated GAM FOLDED PRECURSOR RNA, are set forth in Table 5, incorporated herein Nucleotide sequences of target binding sites, such as BINDING SITE-I, BINDING SITE-II and BINDING SITE-III of FIG. 8, found on GAM1032 target RNA, herein designated GAM TARGET RNA, and a schematic representation of the complementarity of each of these target binding sites to GAM1032 RNA, herein designated GAM RNA, are set forth in Tables 6 and 7, incorporated herein.It is appreciated that specific functions, and accordingly utilities, of GAM1032 RNA correlate with, and may be deduced from, the identity of the GAM1032 target gene inhibited thereby, whose functions are set forth in Table 8, incorporated herein. |

Table 3 shows data relating to the source and location of the GAM oligonucleotide, specifically the GAM PRECURSOR (hairpin) and its position in the human genome.

TABLE 3

| GAM NAME GAM | PRE-CUR SEQ-ID | ORGAN-ISM | CHR | STR AND | CHR-START OFFSET | CHR-END OFFSET | SOURCE REF-ID |
|---|---|---|---|---|---|---|---|
| 1032 | 6527 | hsa | 8 | − | 141427052 | 141427182 | |

Table 4 shows a schematic representation of the GAM folded precursor as set forth in SEQ ID NO: 6527, beginning at the 5' end (beginning of upper row) to the 3' end (beginning of lower row), where the hairpin loop is positioned at the right part of the schematic.

TABLE 4

| GAM NAME | PRE-CUR SEQ-ID | PRECURSOR-SEQUENCE | GAM FOLDED PRECURSOR RNA |
|---|---|---|---|
| GAM 1032 | 6527 | GCTAGTCACT GGGGCAAAGA TGACTAAAAC ACTTTTCCTG CCCTCGAGGA GCTCACAGTC TAGTATGTCT CATCCCCTAC TAGACTGAAG CTCCTTGAGG ACAGGGATGG TCATACTCAC CTCGGTGTTG C | TACT    CAAAG    AAACACTT  C    CA<br>TGT GC  CACTGGGG  ATGACTA    TTCCTG CCTCGAGGAGCT<br>CAGTCTAGTA CG  GTGGCTCC  TACTGGT    AGGGAC GGAGTTCCTCGA<br>GTCAGATCAT  TT--    ACTCA    --------    A<br>A-    -- CTCATCCCC  --------- |

Table 5 shows the mature GAM RNA as set forth in SEQ ID NO: 15 as sliced by DICER from the GAM PRECURSOR sequence (hairpin) as set forth in SEQ ID NO: 6527.

TABLE 5

| GAM NAME | GAM RNA SEQUENCE | PRECUR SEQ-ID | SOURCE REF-ID | GAM POS |
|---|---|---|---|---|
| GAM1032 | CTAGACTGAAGCTCCTTGAGGA | 6527 | | A |

Table 6 shows data relating to the SEQ ID NO of the GAM target binding site sequence of the target gene name as bound by the GAM RNA as set forth in SEQ ID NO: 15.

TABLE 6

| TARGET BINDING SITE SEQ-ID | TARGET | TARGET BINDING SITE SEQUENCE |
|---|---|---|
| 3504 | CHAT | TGCTCCTGCCACTAGGTTTCA |
| 3505 | CHAT | TGGGGAAGTGCGGTGACTGGGAAATGC |
| 3506 | CHAT | CCAGCGCACAGCCTGGGCAG |
| 3507 | CHAT | CATCCCTGCACCAGGACTCACCAAGA |
| 3508 | CHAT | CAAGACGCCCATCCTGGAAAAGGTCCC |
| 3509 | CHAT | AGGCAGCAGAGCCGAGGAGAGCAGGT |
| 3510 | CHAT | CGCGTCAGGCCCAGCGCACAGCCTG |
| 3511 | CHAT | GCACAGCCTGGGCAGCTCAGCCTG |
| 3512 | CHAT | GAGCTAGGGGCAGGAGGCATG |
| 3513 | CHAT | GAGAAAGGAGTAGGAGCCTAGCA |
| 3514 | CHAT | GCCTCAAGGGGTGCGGCCCTCTCAG |
| 3515 | CHAT | GCGTCAGGCCCAGCGCACAGCCTG |
| 3516 | CHAT | GCTCAGCCTGTCAGCTGAGCACGGGCG |
| 3517 | CHAT | GCTTTGAGAAAGGAGTAG |
| 3518 | CHAT | GGTGACTGGGAAATGCTGAG |
| 3519 | CHAT | GTCCGACCTCTGGAAATGT |
| 3520 | CHAT | GGCTCACACCCCCGCCCACAC |
| 3651 | CTSK | GCACCCTAGAGGACTAGGGTA |
| 3652 | CTSK | CTTCCACGATGGTGCAGTG |
| 3653 | CTSK | CTTCCTACTTTGCTTCTCTCCA |
| 3654 | CTSK | CTTCCCTTCTTTGCAC |
| 3655 | CTSK | CTGACTTCTCACTTCCTAAG |
| 3656 | CTSK | CCTACTTTGCTTCTCTCCA |
| 3657 | CTSK | CCTTCCTACTTTGCTTCTCTC |
| 3658 | CTSK | GTCTATGTTTTCTACTCCAA |
| 3659 | CTSK | GTACAGGTACAGGCTGGAGATT |
| 3660 | CTSK | CAGTGTAACGATGCACTTTGG |
| 3661 | CTSK | AATAAATCTAGCACCCCTGAT |

TABLE 6-continued

| TARGET BINDING SITE SEQ-ID | TARGET | TARGET BINDING SITE SEQUENCE |
|---|---|---|
| 3662 | CTSK | TCTATTCATAAGTCTTTGGTACAAG |
| 3663 | CTSK | TCCTGCTCTTCCATTTCTTCC |
| 3664 | CTSK | TCCTACTTTGCTTCTCTCCA |
| 3665 | CTSK | TCCTCAAGGTAGAAATGTCTAT |
| 3666 | CTSK | TCCATCCTGCTCTTCCATTTCTTCCA |
| 3667 | CTSK | TGACTTCTCACTTCCTAAG |
| 3668 | CTSK | TCTTCCACGATGGTGCAGTG |
| 3669 | CTSK | TTGAAGCAGATGTGGTGA |
| 3670 | CTSK | TTGTCCCAGGGCTGATGCTGT |
| 3671 | CTSK | TTTCCAGCCGATCACTGGAGCT |
| 4796 | MPO | TTTATCCATAGACAGGGCCC |
| 4797 | MPO | TATTGAGCACCTACTACATGCA |
| 4798 | MPO | TCCTTGCCCTAGATGAGCCCAGC |
| 4799 | MPO | TCCTCACCCTGATTTCTTGCTT |
| 4800 | MPO | TCAGGTGAGCTGTGGAGGTGGGGTC |
| 4801 | MPO | GGAGAAGAGAGATGGGGGTTCC |
| 4802 | MPO | GGAGCACAGCTCAGGAACTAGA |
| 4803 | MPO | GGAGGTGGGGTCCTTGGAAGC |
| 4804 | MPO | GCTCCCCTTTTTCTTCCTCA |
| 4805 | MPO | GCTCAGGAACTAGACTGCCTG |
| 4806 | MPO | GCTGGGCTGTGTGGTTGACTT |
| 4807 | MPO | GCCCAGCCCTGTTCTGGGTGCAG |
| 4808 | MPO | GGGCCTGTTGCCCTTTCTGTACCA |
| 4809 | MPO | GGGAAGCCTCCTAAGGCCAGG |
| 4810 | MPO | GGCCAGGTAAGGGGGTGCAGCAGTGAG |
| 4811 | MPO | GGCTCCCCTTTTTCTTCCTCACCCT |
| 4812 | MPO | GGTGAGCTGTGGAGGTGGGG |
| 4813 | MPO | GAGCAAATTACCCTCCTTAAACAAGAG |
| 4814 | MPO | CTTGTAAATTACATCTGTCATGGTTT |
| 4815 | MPO | CCTCAAGGAGGTCTGG |
| 4816 | MPO | CCTCTGGTTCTTCATTTATTGAG |
| 4817 | MPO | CTGAGTATGTGGAAGGCAGCA |
| 4818 | MPO | CTGAGTATGTGGAAGGCAGCAGAGCGGA |
| 4819 | MPO | AGGGCCCACTTGTATCCTCTG |
| 4820 | MPO | ATCTGTGTCCTGGTTAGCAGAGC |
| 4821 | MPO | CAGCTCAGGAACTAGACTGCCT |
| 4822 | MPO | CCCTCAAGGAGGTCTGG |
| 4823 | MPO | ACAGCTCAGGAACTAGACTGCCT |
| 4824 | MPO | AGGCAGCAGAGCGGACTGGTGA |
| 4825 | MPO | AAGGCAGCAGAGCGGACTGGTGA |
| 5322 | SERPIN | TGAAGCTCTCACACGCACAG |
| 5323 | SERPIN | CAGTCTGGAGGGTCCTGGCC |
| 5324 | SERPIN | CATGTGTGGCCCTGTCTGCTTA |
| 5325 | SERPIN | CCCATGGACTCTTCAGTCTGG |
| 5326 | SERPIN | ATGTGTGGCCCTGTCTGCTTA |
| 5327 | SERPIN | AGTAGGAACTTGGAATGCAAG |
| 5328 | SERPIN | GAAGCTCTCACACGCACAG |
| 5329 | SERPIN | CCTGTGCACCGTAGTGGCCATGG |
| 5330 | SERPIN | CTCTTCAGTCTGGAGGGTCCTGG |
| 5331 | SERPIN | GCCCATGGACTCTTCAGTCTGG |
| 5541 | TNFRSF | GTGAAAAACAACAAATTCAGTTCTGA |
| 5542 | TNFRSF | GTGACACACAGGTGTTCAAAGACG |
| 5543 | TNFRSF | GGCAAGACTGCCCTTAGAAATTCTAG |
| 5544 | TNFRSF | GCGTATGACACATTGA |
| 5545 | TNFRSF | GCCAGCCCTGGCTGCCCAGGCGGAG |
| 5546 | TNFRSF | GACGCTTCTGGGGAGTGAGGGAA |
| 5547 | TNFRSF | GACAATGTCCAAGCACAGCAGA |
| 5548 | TNFRSF | CTTTGCCACCTCTCCATTTTTGCC |
| 5549 | TNFRSF | CTGCCCTTAGAAATTCTAGCC |
| 5550 | TNFRSF | CTGGCTCAAAACTACCTA |
| 5551 | TNFRSF | CGCAAGAGTGACACACAGGTGTTCA |
| 5552 | TNFRSF | ATGTCCAAGACACAGCAGAACAGA |
| 5553 | TNFRSF | ATGCAGAAAGCACAGAAAGGA |
| 5554 | TNFRSF | ATGTAAACTGTGAAGATAGTT |
| 5555 | TNFRSF | ATGGAAAGAAAGAAGCGTATGACACA |
| 5556 | TNFRSF | ATGGAAAGAAAGAAGCGTATGACACAT |
| 5557 | TNFRSF | ATTTAAATAAGGCTCTACCTC |
| 5558 | TNFRSF | ACAATGTCCAAGACACAGCAGA |
| 5559 | TNFRSF | TCCTCAAGGACATTACTAG |
| 5560 | TNFRSF | TCTCAGGCATCAAAAGCATTTTG |
| 5561 | TNFRSF | TCCAAGGATGTTTAAAATCTAGTTGG |
| 5562 | TNFRSF | TGGGTGAAGAGAAAGGAAGTACAGA |
| 5563 | TNFRSF | TCTTTCTCAGGCATCAAAAGCATT |
| 5564 | TNFRSF | TTGGGTGAAGAGAAAGGAAGTACAGA |

Table 7, lines 1468-1501 shows data relating to target genes and binding site of GAM oligonucleotides.

TABLE 7

| GAM NAME | GAM RNA SEQUENCE | TARGET | TARGET REF-ID | TARGET UTRBS-SEQ | BINDING-SITE DRAW (UPPER:GAM; LOWER:TARGET) | GAM POS |
|---|---|---|---|---|---|---|
| GAM1032 | CTAGACTG AAG CTCCTTGA GGA | CHAT | NM_02 0984.1 | 5 | GCCTCA      -    ---     AA             A<br>AGGGGT CT AGA    CTG  GCTCCTTGAGG<br>G      GA TCT    GGC  TGGGGAACTCC<br>CGGCCC  C    CCC  G-             G<br>TCTCAG | A |
| GAM1032 | CTAGACTG AAG CTCCTTGA GGA | CTSK | NM_00 0396.2 | 3 | TCCTCA C      TGAAG  -   TAGAC<br>AGGTAG     CT CCTTGAGGA ATCTG<br>A          GA GGAACTCCT T<br>AATGTC      TAAA- T<br>TAT | A |
| GAM1032 | CTAGACTG AAG CTCCTTGA GGA | MPO | NM_00 0250.1 | 5 | CCCTCA       TGAAG         A<br>AGGAGG CTAGAC      CTCCTTGAGG<br>T CTGG GGTCTG      GAGGAACTCC<br>                -----         C | A |
| GAM1032 | CTAGACTG AAG CTCCTTGA GGA | MPO | NM_00 0250.1 | 5 | CCTCAA       TGAAG CTAGAC<br>GGAGGT       CTCCTTGAGG GGTCTG<br>C TGG        GAGGAACTCC     ----- | A |
| GAM1032 | CTAGACTG AAG CTCCTTGA GGA | SERPI NA 3 | NM_00 1085.2 | 3 | CCCATG           C-  T   A<br>GACTCT CTAGACTGAAG  TCC TG GG<br>T       GGTCTGACTTC  AGG AC CC<br>CAGTCT             TC   T   -<br>GG | A |
| GAM1032 | CTAGACTG AAG CTCCTTGA GGA | SERPI NA 3 | NM_00 1085.2 | 3 | GCCCAT           C-   T  A  A<br>GGACTC CTAGACTGAAG  TCC TG GG<br>T       GGTCTGACTTC  AGG AC CC<br>TCAGTC             TC   T  -  G<br>TGG | A |
| GAM1032 | CTAGACTG AAG CTCCTTGA GGA | TNFRS F6 | NM_15 2874.1 | 3 | TCCTCA     AC    AGC CTAG  TGA<br>AGGACA   TCCTTGAGGA GATC  ATT<br>T        AGGAACTCCT        --  AC-<br>TACTAG | A |

It is appreciated that the specific functions and accordingly the utilities a GAM oligonucleotide that is described by FIG. 8 is correlated with and may be deduced from the identity of the GAM TARGET GENES inhibited thereby, and whose functions are set forth in Table 8. Table 8 shows data relating to the function and utilities of GAM RNA as set forth in SEQ ID NO: 15.

TABLE 8

| GAM NAME | GAM TARGET | GAM RNA SEQUENCE | GAM FUNCTION | GAM POS | TAR DIS |
|---|---|---|---|---|---|
| GAM1 032 | TNFRSF 6 | CTAGACTG AAGCTCC TTGAGGA | TNFRSF6 (Accession NM_152874.1) is another GAM1032 target gene. TNFRSF6 BINDING SITE is a target binding site found in the 3' untranslated region of multiple transcripts of mRNA encoded by TNFRSF6, corresponding to a target binding site such as BINDING SITE I, BINDING SITE II or BINDING SITE III of FIG. 8. Nucleotide sequences of TNFRSF6 BINDING SITE, and secondary structure complementarity to the nucleotide sequence of GAM1032 RNA are set forth in | A | A |

TABLE 8-continued

| GAM NAME | GAM TARGET | GAM RNA SEQUENCE | GAM FUNCTION | GAM POS | TAR DIS |
|---|---|---|---|---|---|
| | | | Tables 6 and 7, hereby incorporated herein. Another function of GAM1032 is therefore inhibition of TNFRSF6. Accordingly, utilities of GAM1032 include diagnosis, prevention and treatment of Alzheimer, and of other diseases and clinical conditions associated with TNFRSF6. | | |
| GAM 1032 | CHAT | CTAGACTG AAGCTCC TTGAGGA | Choline Acetyltransferase (CHAT, Accession NM_020984.1) is a GAM1032 target gene. CHAT BINDING SITE is a target binding site found in the 5' untranslated region of multiple transcripts of mRNA encoded by CHAT, corresponding to a target binding site such as BINDING SITE I, BINDING SITE II or BINDING SITE III of FIG. 8. Nucleotide sequences of CHAT BINDING SITE, and secondary structure complementarity to the nucleotide sequence of GAM1032 RNA are set forth in Tables 6 and 7, hereby incorporated herein. A function of GAM1032 is therefore inhibition of CHAT, a GAM1032 target gene which synthesizes the neurotransmitter acetylcholine. and therefore is associated with Alzheimer. Accordingly, utilities of GAM1032 include diagnosis, prevention and treatment of Alzheimer, and of other diseases and clinical conditions associated with CHAT. The function of CHAT and its association with various diseases and clinical conditions, has been established by previous studies, as described hereinabove with reference to GAM335. | A | A |
| GAM1 032 | CTSK | CTAGACTG AAGCTCC TTGAGGA | CTSK (Accession NM_000396.2) is another GAM1032 target gene. CTSK BINDING SITE is a target binding site found in the 3' untranslated region of mRNA encoded by CTSK, corresponding to a target binding site such as BINDING SITE I, BINDING SITE II or BINDING SITE III of FIG. 8. Nucleotide sequences of CTSK BINDING SITE, and secondary structure complementarity to the nucleotide sequence of GAM1032 RNA are set forth in Tables 6 and 7, hereby incorporated herein. Another function of GAM1032 is therefore inhibition of CTSK. | A | A |

TABLE 8-continued

| GAM NAME | GAM TARGET | GAM RNA SEQUENCE | GAM FUNCTION | GAM POS | TAR DIS |
|---|---|---|---|---|---|
| | | | Accordingly, utilities of GAM1032 include diagnosis, prevention and treatment of Alzheimer, and of other diseases and clinical conditions associated with CTSK. | | |
| GAM1 032 | MPO | CTAGACTG AAGCTCC TTGAGGA | Myeloperoxidase (MPO, Accession NM_000250.1) is another GAM1032 target gene. MPO BINDING SITE1 and MPO BINDING SITE2 are target binding sites found in untranslated regions of mRNA encoded by MPO, corresponding to target binding sites such as BINDING SITE I, BINDING SITE II or BINDING SITE III of FIG. 8. Nucleotide sequences of MPO BINDING SITE1 and MPO BINDING SITE2, and secondary structure complementarity to the nucleotide sequence of GAM1032 RNA are set forth in Tables 6 and 7, hereby incorporated herein. Another function of GAM1032 is therefore inhibition of MPO, a GAM1032 target gene which is present in primary granules of neutrophilic granulocytes. and therefore is associated with Alzheimer. Accordingly, utilities of GAM1032 include diagnosis, prevention and treatment of Alzheimer, and of other diseases and clinical conditions associated with MPO. The function of MPO has been established by previous studies. Weil et al. (1988) found that the MPO gene was translocated to chromosome 15 in all cases of acute promyelocytic leukemia (subtype M3), which is consistently associated with the chromosomal translocation t(15;17)(q22;q11.2). In 2 of 4 cases examined by genomic blot analysis, rearrangement of the MPO gene was detected in leukemia cells. Weil et al. (1988) also suggested that MPO may be pivotal in the pathogenesis of APL. According to HGM10, the MPO gene is located at a distance from the breakpoint in APL, and the gene itself is probably usually not rearranged in APL. Myeloperoxidase has been detected in activated microglial macrophages and within amyloid plaques in the central nervous system. Using statistical analysis, Reynolds et al. (2000) examined the relationship between APOE (OMIM Ref. No. 107741) and MPO polymorphisms in the risk of | A | A |

TABLE 8-continued

| GAM NAME | GAM TARGET | GAM RNA SEQUENCE | GAM FUNCTION | GAM POS | TAR DIS |
|---|---|---|---|---|---|
| | | | Alzheimer disease (AD; 104300) in a genetically homogeneous Finnish population. They found that the presence of the MPO A allele in conjunction with APOE E4 significantly increased the risk of AD in men, but not in women (odds ratio for men with both alleles = 11.4 vs APOE E4 alone = 3.0). Reynolds et al. (2000) also found that estrogen receptor- alpha (OMIM Ref. No. 133430) binds to the MPO A promoter, which may explain the gender differences. Full details of the abovementioned studies are described in the following publications, the disclosure of which are hereby incorporated by reference: Reynolds, W. F.; Hiltunen, M.; Pirskanen, M.; Mannermaa, A.; Helisalmi, S.; Lehtovirta, M.; Alafuzoff, I.; Soininen, H.: MPO and APOE epsilon- 4 polymorphisms interact to increase risk for AD in Finnish males. Neurology 55: 1284-1290, 2000.; an Weil, S. C.; Rosner, G. L.; Reid, M. S.; Chisholm, R. L.; Lemons, R. S.; Swanson, M. S.; Carrino, J. J.; Diaz, M. O.; Le Beau, M. M.: Translocation and rearrangement of myeloperoxida Further studies establishing the function and utilities of MPO are found in John Hopkins OMIM database record ID 606989, and in cited publications listed in Table 9, hereby incorporated herein. | | |
| GAM1 032 | SERPIN A 3 | CTAGACTG AAGCTCC TTGAGGA | Serine (or cysteine) Proteinase Inhibitor, Clade A (alpha-1 antiprotei (SERPINA3, Accession NM_001085.2) is another GAM1032 target gene. SERPINA3 BINDING SITE1 and SERPINA3 BINDING SITE2 are target binding sites found in untranslated regions of mRNA encoded by SERPINA3, corresponding to target binding sites such as BINDING SITE I, BINDING SITE II or BINDING SITE III of FIG. 8. Nucleotide sequences of SERPINA3 BINDING SITE1 and SERPINA3 BINDING SITE2, and secondary structure complementarity to the nucleotide sequence of GAM1032 RNA are set forth in Tables 6 and 7, hereby incorporated herein. Another function of GAM1032 is therefore inhibition of SERPINA3, a GAM1032 target gene which is | A | A |

TABLE 8-continued

| GAM NAME | GAM RNA TARGET SEQUENCE | GAM FUNCTION | GAM POS | TAR DIS |
|---|---|---|---|---|
| | | a member of the serpin family of serine protease inhibitors. and therefore is associated with Alzheimer. Accordingly, utilities of GAM1032 include diagnosis, prevention and treatment of Alzheimer, and of other diseases and clinical conditions associated with SERPINA3. The function of SERPINA3 has been established by previous studies. Alpha-1-antichymotrypsin is a plasma protease inhibitor synthesized in the liver. It is a single glycopeptide chain of about 68,000 daltons and belongs to the class of serine protease inhibitors. In man, the normal serum level is about one-tenth that of alpha-1-antitrypsin (PI; 107400), with which it shares nucleic acid and protein sequence homology (Chandra et al. 1983). Both are major acute phase reactants; their concentrations in plasma Increase in response to trauma, surgery, and infection. Antithrombin III, which also is structurally similar to alpha-1-antitrypsin, shows less sequence homology to antichymotrypsin and is not an acute phase reactant. Kelsey et al. (1988) cloned and analyzed the AACT gene, partly because of the possibility that genetic variation in other protease inhibitors may influence the prognosis in AAT deficiency. They isolated the AACT gene on a series of cosmid clones, with restriction mapping of about 70 kb around the gene. Full details of the abovementioned studies are described in the following publications, the disclosure of which are hereby incorporated by reference: Chandra, T.; Stackhouse, R.; Kidd, V. J.; Robson, K. J. H.; Woo, S. L. C.: Sequence homology between human alpha-1-antichymotrypsin, alpha-1-antitrypsin, and antithrombin III. Biochemistry 22: 5055-5061, 1983.; an Kelsey, G. D.; Abeliovich, D.; McMahon, C. J.; Whitehouse, D.; Corney, G.; Povey, S.; Hopkinson, D. A.; Wolfe, J.; Mieli-Vergani, G.; Mowat, A. P.: Cloning of the human alpha-1 antichym Further studies establishing the function | | |

TABLE 8-continued

| GAM NAME | GAM RNA TARGET SEQUENCE | GAM FUNCTION | GAM POS | TAR DIS |
|---|---|---|---|---|
| | | and utilities of SERPINA3 are found in John Hopkins OMIM database record ID 107280, and in cited publications listed in Table 9, hereby incorporated herein. | | |

Studies documenting the well known correlations between GAM TARGET GENEs that are described by FIG. 8 and the known gene functions and related diseases are listed in Table 9. Specifically, Table 9 describes references of GAM target genes, as set forth in SEQ ID NO:15 in Table 8.

TABLE 9

| GAM NAME | GAM RNA SEQUENCE | TARGET | REFERENCES | GAM POS |
|---|---|---|---|---|
| GAM103 2 | CTAGAC TGAAGC TC CTTGAG GA | CHAT | Barrard, B. A.; Lottspeich, F.; Braun, A.; Barde, Y. A.; Mallet, J.: cDNA cloning and complete sequence of porcine choline acetyltransferase: in vitro translation of the corresponding RNA yields an active protein. Proc. Nat. Acad. Sci. 84:9280-9284, 1987. | A |
| GAM103 2 | CTAGAC TGAAGC TC CTTGAG GA | CHAT | Chireux, M. A.; Le Van Thai, A.; Weber, M. J.: Human choline acetyltransferasegene: localization of alternative first exons. J. Neurosci. Res. 40:427-438, 1995. | A |
| GAM103 2 | CTAGAC TGAAGC TC CTTGAG GA | CHAT | Cohen-Haguenauer, O.; Brice, A.; Berrard, S.; Van Cong, N.; Mallet, J.; Frezal, J.: Localization of the choline acetyltransferase (CHAT)gene to human chromosome 10. Genomics 6:374-378, 1990. | A |
| GAM103 2 | CTAGAC TGAAGC TC CTTGAG GA | CHAT | Erickson, J. D.; Varoqui, H.; Schafer, M. K.-H.; Modi, W.; Diebler, M.-F.; Weihe, E.; Rand, J.; Eiden, L. E.; Bonner, T. I.; Usdin, T. B.: Functional identification of a vesicular acetylcholine transporter and its expression from a 'cholinergic' gene locus. J. Biol. Chem. 269:21929-21932, 1994. | A |
| GAM103 2 | CTAGAC TGAAGC TC CTTGAG GA | CHAT | Misawa, H.; Ishii, K.; Deguchi, T.: Gene expression of mouse cholineacetyltransferase: alternative splicing and identification of a highlyactive promoter region. J. Biol. Chem. 267: 20392-20399, 1992. | A |
| GAM103 2 | CTAGAC TGAAGC TC CTTGAG GA | CHAT | Ohno, K.; Tsujino, A.; Brengman, J. M.; Harper, C. M.; Bajzer, Z.; Udd, B.; Beyring, R.; Robb, S.; Kirkham, F. J.; Engel, A. G.: Choline acetyltransferase mutations cause myasthenic syndrome associated with episodic apnea in humans. Proc. Nat. Acad. Sci. 98:2017-2022, 2001. | A |
| GAM103 2 | CTAGAC TGAAGC TC CTTGAG GA | CHAT | Strauss, W. L.; Kemper, R. R.; Jayakar, P.; Kong, C. F.; Hersh, L. B.; Hilt, D. C.; Rabin, M.: Human choline acetyltransferase genemaps to region 10q11-q22.2 by in situ hybridization. Genomics 9:396-398, 1991. | A |

TABLE 9-continued

| GAM NAME | GAM RNA SEQUENCE | TARGET | REFERENCES | GAM POS |
|---|---|---|---|---|
| GAM1032 | CTAGAC TGAAGC TC CTTGAG GA | CHAT | Toussaint, J. L.; Geoffroy, V.; Schmitt, M.; Werner, A.; Garnier, J. M.; Simoni, P.; Kempf, J.: Human choline acetyltransferase (CHAT): partial gene sequence and potential control regions. Genomics 12:412-416, 1992. | A |
| GAM1032 | CTAGAC TGAAGC TC CTTGAG GA | CHAT | Viegas-Pequignot, E.; Berrard, S.; Brice, A.; Apiou, F.; Mallet, J.: Localization of a 900-bp-long fragment of the human choline acetyltransferasegene to 10q11.2 by nonradioactive in situ hybridization. Genomics 9:210-212, 1991. | A |
| GAM1032 | CTAGAC TGAAGC TC CTTGAG GA | MPO | Borregaard, N.; Cowland, J. B.: Granules of the human neutrophilicpolymorphonuclear leukocyte. Blood 89:3503-3521, 1997. | A |
| GAM1032 | CTAGAC TGAAGC TC CTTGAG GA | MPO | Chang, K. S.; Schroeder, W.; Siciliano, M. J.; Thompson, L. H.; McCredie, K.; Beran, M.; Freireich, E. J.; Liang, J. C.; Trujillo, J. M.; Stass, S. A.: The localization of the human myeloperoxidasegene is in close proximity to the translocation breakpoint in acutepromyelocytic leukemia. Leukemia 1:458-462, 1987. | A |
| GAM1032 | CTAGAC TGAAGC TC CTTGAG GA | MPO | DeLeo, F. R.; Goedken, M.; McCormick, S. J.; Nauseef, W. M.: Anovel form of hereditary myeloperoxidase deficiency linked to endoplasmicreticulum/proteasome degradation. J. Clin. Invest. 101: 2900-2909, 1998. | A |
| GAM1032 | CTAGAC TGAAGC TC CTTGAG GA | MPO | Eiserich, J. P.; Baldus, S.; Brennan, M.-L.; Ma, W.; Zhang, C.; Tousson, A.; Castro, L.; Lusis, A. J.; Nauseef, W. M.; White, C. R.; Freeman, B. A.: Myeloperoxidase, a leukocyte-derived vascular NOoxidase. Science 296:2391-2394, 2002. | A |
| GAM1032 | CTAGAC TGAAGC TC CTTGAG GA | MPO | Inazawa, J.; Inoue, K.; Nishigaki, H.; Tsuda, S.; Taniwaki, M.; Misawa, S.; Abe, T.: Assignment of the human myeloperoxidase gene(MPO) to bands q21.3-q23 of chromosome 17. Cytogenet. Cell Genet. 50:135-136, 1989. | A |
| GAM1032 | CTAGAC TGAAGC TC CTTGAG GA | MPO | Johnson, K.; Gemperlein, I.; Hudson, S.; Shane, S.; Rovera, G.: Complete nucleotide sequence of the human myeloperoxidase gene. NucleicAcids Res. 17:7985-7986, 1989. | A |
| GAM1032 | CTAGAC TGAAGC TC CTTGAG GA | MPO | Kizaki, M.; Miller, C. W.; Selsted, M. E.; Koeffler, H. P.: Myeloperoxidase(MPO) gene mutation in hereditary MPO deficiency. Blood 83:1935-1940, 1994. | A |
| GAM1032 | CTAGAC TGAAGC TC CTTGAG GA | MPO | Klebanoff, S. J.: Myeloperoxidase. Proc. Assoc. Am. Physicians 111:383-389, 1999. | A |

TABLE 9-continued

| GAM NAME | GAM RNA SEQUENCE | TARGET | REFERENCES | GAM POS |
|---|---|---|---|---|
| GAM103 2 | CTAGAC TGAAGC TC CTTGAG GA | MPO | Kudoh, J.; Minoshima, S.; Hashinaka, K.; Nishio, C.; Yamada, M.; Shimizu, Y.; Shimizu, N.: Assignment of the myeloperoxidase (MPO) gene to human chromosome 17. (Abstract) Cytogenet. Cell Genet. 46:641-642, 1987. | A |
| GAM103 2 | CTAGAC TGAAGC TC CTTGAG GA | MPO | Kudoh, J.; Minoshima, S.; Hashinaka, K.; Nishio, C.; Yamada, M.; Shimizu, Y.; Shimizu, N.: Assignment of the myeloperoxidase geneMPO to human chromosome 17 using somatic cell hybrids and flow-sortedchromosomes. Jpn. J. Hum. Genet. 33:315-324, 1988. | A |
| GAM103 2 | CTAGAC TGAAGC TC CTTGAG GA | MPO | Law, D. J.; Prasad, M. A.; King, S. E.; Spranger, K. D.; Lee, Y. H.; Fox, R. E.; Collins, E. E.; Gebuhr, T. C.; Miller, D. E.; Petty, E. M.: Localization of the human estrogen-responsive finger protein(EFP) gene (ZNF147) within a YAC contig containing the myeloperoxidase(MPO) gene. Genomics 28:361-363, 1995. | A |
| GAM103 2 | CTAGAC TGAAGC TC CTTGAG GA | MPO | Le Beau, M. M.; Lemons, R. S.; Rosner, G. L.; Carrino, J. C.; Reid, M. S.; Chisholm, R. L.; Diaz, M. O.; Weil, S. C.: Chromosomallocalization of the gene encoding myeloperoxidase. (Abstract) Cytogenet.Cell Genet. 46:645, 1987. | A |
| GAM103 2 | CTAGAC TGAAGC TC CTTGAG GA | MPO | Liang, J. C.; Chang, K. S.; Schroeder, W. T.; Freireich, E. J.; Stass, S. A.; Trujillo, J. M.: The myeloperoxidase gene is translocatedfrom chromosome 17 to 15 in a patient with acute promyelocytic leukemia. CancerGenet. Cytogenet. 30:103-107, 1988. | A |
| GAM103 2 | CTAGAC TGAAGC TC CTTGAG GA | MPO | Liang, J. C.; Chang, K. S.; Schroeder, W.; Siciliano, M.; Trujillo, J.; Stass, S.: The human myeloperoxidase gene locates on chromosome 17q22-24 and is translocated in acute promyelocytic leukemia. (Abstract) Am. J. Hum. Genet. 41:A226, 1987. | A |
| GAM103 2 | CTAGAC TGAAGC TC CTTGAG GA | MPO | Miki, T.; Weil, S. C.; Rosner, G. L.; Reid, M. S.; Kidd, K. K.: An MPO cDNA clone identifies an RFLP with PstI. Nucleic Acids Res. 16:1649, 1988. | A |
| GAM103 2 | CTAGAC TGAAGC TC CTTGAG GA | MPO | Morishita, K.; Kubota, N.; Asano, S.; Kaziro, Y.; Nagata, S.: Molecular cloning and characterization of cDNA for human myeloperoxidase. J. Biol. Chem. 262:3844-3851, 1987. | A |
| GAM103 2 | CTAGAC TGAAGC TC CTTGAG GA | MPO | Murao, S.-I.; Stevens, F. J.; Ito, A.; Huberman, E.: Myeloperoxidase: a myeloid cell nuclear antigen with DNA-binding properties. Proc. Nat. Acad. Sci. 85:1232-1236, 1988. | A |
| GAM103 2 | CTAGAC TGAAGC TC CTTGAG GA | MPO | Nauseef, W. M.; Brigham, S.; Cogley, M.: Hereditary myeloperoxidasedeficiency due to a missense mutation of arginine 569 to tryptophan. J. Biol. Chem. 269:1212-1216, 1994. | A |

TABLE 9-continued

| GAM NAME | GAM RNA SEQUENCE | TARGET | REFERENCES | GAM POS |
|---|---|---|---|---|
| GAM103 2 | CTAGAC TGAAGC TC CTTGAG GA | MPO | Nauseef, W. M.; Olsson, I.; Arnljots, K.: Biosynthesis and processing of myeloperoxidase - - a marker for myeloid cell differentiation. Europ. J. Haemat. 40:97-110, 1988. | A |
| GAM103 2 | CTAGAC TGAAGC TC CTTGAG GA | MPO | Nauseef, W.; Cogley, M.; McCormick, S.: Effect of the R569W missensemutation on the biosynthesis of myeloperoxidase. J. Biol. Chem. 271:9546-9549, 1996. | A |
| GAM103 2 | CTAGAC TGAAGC TC CTTGAG GA | MPO | Reynolds, W. F.; Hiltunen, M.; Pirskanen, M.; Mannermaa, A.; Helisalmi, S.; Lehtovirta, M.; Alafuzoff, I.; Soininen, H.: MPO and APOE epsilon-4polymorphisms interact to increase risk for AD in Finnish males. Neurology 55:1284-1290, 2000. | A |
| GAM103 2 | CTAGAC TGAAGC TC CTTGAG GA | MPO | Robinson, T. J.; Morris, D. J.; Ledbetter, D. H.: Chromosomalassignment and regional localization of myeloperoxidase in the mouse. Cytogenet. Cell Genet. 53: 83-86, 1990. | A |
| GAM103 2 | CTAGAC TGAAGC TC CTTGAG GA | MPO | Romano, M.; Dri, P.; Dadalt, L.; Patriarca, P.; Baralle, F. E.: Biochemical and molecular characterization of hereditary myeloproliferativedeficiency. Blood 90:4126-4134, 1997. | A |
| GAM103 2 | CTAGAC TGAAGC TC CTTGAG GA | MPO | van Tuinen, P.; Johnson, K. R.; Ledbetter, S. A.; Nussbaum, R. L.; Rovera, G.; Ledbetter, D. H.: Localization of myeloperoxidaseto the long arm of human chromosome 17: relationship to the 15;17translocation of acute promyelocytic leukemia. Oncogene 1: 319-322, 1987. | A |
| GAM103 2 | CTAGAC TGAAGC TC CTTGAG GA | MPO | Weil, S. C.; Rosner, G. L.; Reid, M. S.; Chisholm, R. L.; Farber, N. M.; Spitznagel, J. K.; Swanson, M. S.: cDNA cloning of human myeloperoxidase: decrease in myeloperoxidase mRNA upon induction of HL-60 cells. Proc. Nat. Acad. Sci. 84:2057-2061, 1987. | A |
| GAM103 2 | CTAGAC TGAAGC TC CTTGAG GA | MPO | Weil, S. C.; Rosner, G. L.; Reid, M. S.; Chisholm, R. L.; Lemons, R. S.; Swanson, M. S.; Carrino, J. J.; Diaz, M. O.; Le Beau, M. M.: Translocation and rearrangement of myeloperoxidase gene in acutepromyelocytic leukemia. Science 240:790-792, 1988. | A |
| GAM103 2 | CTAGAC TGAAGC TC CTTGAG GA | MPO | Yamada, M.; Hur, S.-J.; Hashinaka, K.; Tsuneoka, K.; Saeki, T.; Nishio, C.; Sakiyama, F.; Tsunasawa, S.: Isolation and characterization of a cDNA coding for human myeloperoxidase. Arch. Biochem. Biophys. 255:147-155, 1987. | A |
| GAM103 2 | CTAGAC TGAAGC TC CTTGAG | MPO | Zaki, S. R.; Austin, G. E.; Chan, W. C.; Conaty, A. L.; Trusler, S.; Trappier, S.; Lindsey, R. B.; Swan, D. C.: Chromosomal localization of | A |

TABLE 9-continued

| GAM NAME | GAM RNA SEQUENCE | TARGET | REFERENCES | GAM POS |
|---|---|---|---|---|
| | GA | | the human myeloperoxidase gene by in situ hybridization using oligonucleotideprobes. Genes Chromosomes Cancer 2:266-270, 1990. | |
| GAM103 2 | CTAGAC TGAAGC TC CTTGAG GA | SERPIN A3 | Chandra, T.; Stackhouse, R.; Kidd, V. J.; Robson, K. J. H.; Woo, S. L. C.: Sequence homology between human alpha-1-antichymotrypsin, alpha-1-antitrypsin, and antithrombin III. Biochemistry 22:5055-5061, 1983. | A |
| GAM103 2 | CTAGAC TGAAGC TC CTTGAG GA | SERPIN A3 | Eriksson, S.; Lindmark, B.; Lilia, H.: Familial alpha-1-antichymotrypsindeficiency. Acta Med. Scand. 220:447-453, 1986. | A |
| GAM103 2 | CTAGAC TGAAGC TC CTTGAG GA | SERPIN A3 | Gilfix, B. M.; Briones, L.: Absence of the A1252G mutation inalpha 1-antichymotrypsin in a North American population suffering from dementia. J. Cereb. Blood Flow Metab. 17:233-235, 1997. | A |
| GAM103 2 | CTAGAC TGAAGC TC CTTGAG GA | SERPIN A3 | Haines, J. L.; Pritchard, M. L.; Saunders, A. M.; Schildkraut, J. M.; Growdon, J. H.; Gaskell, P. C.; Farrer, L. A.; Auerbach, S. A.; Gusella, J. F.; Locke, P. A.; Rosi, B. L.; Yamaoka, L.; Small, G. W.; Conneally, P. M.; Roses, A. D.; Pericak-Vance, M. A.: No geneticeffect of alpha-1-antichymotrypsin in Alzheimer disease. Genomics 33:53-56, 1996. | A |
| GAM103 2 | CTAGAC TGAAGC TC CTTGAG GA | SERPIN A3 | Haines, J. L.; Scott, W. K.; Pericak-Vance, M. A.: Reply to 'Geneticeffect of alpha-1-antichymotrypsin on the risk of Alzheimer disease.' (Letter) Genomics 40:384-385, 1997. | A |
| GAM103 2 | CTAGAC TGAAGC TC CTTGAG GA | SERPIN A3 | Kamboh, M. I.; Aston, C. E.; Ferrell, R. E.; Dekosky, S. T.: Geneticeffect of alpha-1-antichymotrypsin on the risk of Alzheimer disease. (Letter) Genomics 41:382-385, 1997. | A |
| GAM103 2 | CTAGAC TGAAGC TC CTTGAG GA | SERPIN A3 | Kamboh, M. I.; Sanghera, D. K.; Ferrell, R. E.; DeKosky, S. T.: APOE*4 - associated Alzheimer's disease risk is modified by alpha-1-antichymotrypsinpolymorphism. Nature Genet. 10:486-488, 1995. | A |
| GAM103 2 | CTAGAC TGAAGC TC CTTGAG GA | SERPIN A3 | Kelsey, G. D.; Abeliovich, D.; McMahon, C. J.; Whitehouse, D.; Corney, G.; Povey, S.; Hopkinson, D. A.; Wolfe, J.; Mieli-Vergani, G.; Mowat, A. P.: Cloning of the human alpha-1 antichymotrypsin geneand genetic analysis of the gene in relation to alpha-1 antitrypsindeficiency. J. Med. Genet. 25:361-368, 1988. | A |
| GAM103 2 | CTAGAC TGAAGC TC CTTGAG GA | SERPIN A3 | Morgan, K.; Licastro, F.; Tilley, L.; Ritchie, A.; Morgan, L.; Pedrini, S.; Kalsheker, N.: Polymorphism in the alpha-1-antichymotrypsin(ACT) gene promoter: effect on expression in transfected glial and liver cell lines and plasma ACT concentrations. Hum. Genet. 109:303-310, 2001. | A |

TABLE 9-continued

| GAM NAME | GAM RNA SEQUENCE | TARGET | REFERENCES | GAM POS |
|---|---|---|---|---|
| GAM103 2 | CTAGAC TGAAGC TC CTTGAG GA | SERPIN A3 | Morgan, K.; Morgan, L.; Carpenter, K.; Lowe, J.; Lam, L.; Cave, S.; Xuereb, J.; Wischik, C.; Harrington, C.; Kalsheker, N. A.: Microsatellitepolymorphism of the alpha-1-antichymotrypsin gene locus associated with sporadic Alzheimer's disease. Hum. Genet. 99: 27-31, 1997. | A |
| GAM103 2 | CTAGAC TGAAGC TC CTTGAG GA | SERPIN A3 | Munoz, E.; Obach, V.; Oliva, R.; Marti, M. J.; Ezquerra, M.; Pastor, P.; Ballesta, F.; Tolosa, E.: Alpha-1-antichymotrypsin gene polymorphism and susceptibility to Parkinson's disease. Neurology 52: 297-301, 1999. | A |
| GAM103 2 | CTAGAC TGAAGC TC CTTGAG GA | SERPIN A3 | Poller, W.; Faber, J.-P.; Scholz, S.; Weidinger, S.; Bartholome, K.; Olek, K.; Eriksson, S.: Mis-sense mutation of alpha-1-antichymotrypsingene associated with chronic lung disease. (Letter) Lancet 339:1538, 1992. | A |
| GAM103 2 | CTAGAC TGAAGC TC CTTGAG GA | SERPIN A3 | Poller, W.; Faber, J.-P.; Weidinger, S.; Tief, K.; Scholz, S.; Fischer, M.; Olek, K.; Kirchgesser, M.; Heidtmann, H.-H.: A leucine-to-prolinesubstitution causes a defective alpha-1-antichymotrypsin allele associated with familial obstructive lung disease. Genomics 17:740-743, 1993. | A |
| GAM103 2 | CTAGAC TGAAGC TC CTTGAG GA | SERPIN A3 | Rabin, M.; Watson, M.; Breg, W. R.; Kidd, V.; Woo, S. L. C.; Ruddle, F. H.: Human alpha-1-antichymotrypsin and alpha-1-antitrypsin (PI)genes map to the same region on chromosome 14. (Abstract) Cytogenet. Cell Genet. 40: 728, 1985. | A |
| GAM103 2 | CTAGAC TGAAGC TC CTTGAG GA | SERPIN A3 | Rabin, M.; Watson, M.; Kidd, V.; Woo, S. L. C.; Breg, W. R.; Ruddle, F. H.: Regional location of alpha-1-antichymotrypsin and alpha-1-antitrypsingenes on human chromosome 14. Somat. Cell Molec. Genet. 12: 209-214, 1986. | A |
| GAM103 2 | CTAGAC TGAAGC TC CTTGAG GA | SERPIN A3 | Samilchuk, E. I.; Chuchalin, A. G.: Mis-sense mutation of alpha-1-antichymotrypsingene and chronic lung disease. (Letter) Lancet 342: 624, 1993. | A |
| GAM103 2 | CTAGAC TGAAGC TC CTTGAG GA | SERPIN A3 | Sefton, L.; Kearney, P.; Kelsey, G.; Povey, S.; Wolfe, J.: Physical linkage of the genes PI and AACT. (Abstract) Cytogenet. Cell Genet. 51:1076, 1989. | A |
| GAM103 2 | CTAGAC TGAAGC TC CTTGAG GA | SERPIN A3 | Sefton, L.; Kelsey, G.; Kearney, P.; Povey, S.; Wolfe, J.: Aphysical map of the human PI and AACT genes. Genomics 7:382-388, 1990. | A |
| GAM103 2 | CTAGAC TGAAGC TC CTTGAG | SERPIN A3 | Tachikawa, H.; Tsuda, M.; Onoe, K.; Ueno, M.; Takagi, S.; Shinohara, Y.: Alpha-1-antichymotrypsin gene A1252G variant (ACT Isehara-1) is | A |

TABLE 9-continued

| GAM NAME | GAM RNA SEQUENCE | TARGET | REFERENCES | GAM POS |
|---|---|---|---|---|
| | GA | | associated with a lacunar type of ischemic cerebrovascular disease. J. Hum. Genet. 46:45-47, 2001. | |
| GAM103 2 | CTAGAC TGAAGC TC CTTGAG GA | SERPIN A3 | Tsuda, M.; Sei, Y.; Matsumoto, M.; Kamiguchi, H.; Yamamoto, M.; Shinohara, Y.; Igarashi, T.; Yamamura, M.: Alpha-1-antichymotrypsinvariant detected by PCR - single strand conformation polymorphism (PCR-SSCP)and direct sequencing. Hum. Genet. 90:467-468, 1992. | A |
| GAM103 2 | CTAGAC TGAAGC TC CTTGAG GA | SERPIN A3 | Tsuda, M.; Sei, Y.; Yamamura, M.; Yamamoto, M.; Shinohara, Y.: Detection of a new mutant alpha-1-antichymotrypsin in patients with occlusive-cerebrovascular disease. FEBS Lett. 304:66-68, 1992. | A |
| GAM103 2 | CTAGAC TGAAGC TC CTTGAG GA | SERPIN A3 | Wang, X.; DeKosky, S. T.; Luedecking-Zimmer, E.; Ganguli, M.; Kamboh, M. I.: Genetic variation in alpha-1-antichymotrypsin and its association with Alzheimer's disease. Hum. Genet. 110:356-365, 2002. | A |
| GAM103 2 | CTAGAC TGAAGC TC CTTGAG GA | SERPIN A3 | Yamamoto, M.; Kondo, I.; Ogawa, N.; Asanuma, M.; Yamashita, Y.; Mizuno, Y.: Genetic association between susceptibility to Parkinson's disease and alpha-1-antichymotrypsin polymorphism. Brain Res. 759:153-155, 1997. | A |

Table 11 shows data relating to Alzheimer's and ALL diseases for which GAM RNA SEQ ID NO: 15 is predicted to regulate the disease-associated genes.

TABLE 11

| ROW # | DISEASE NAME | TARGET-GENES ASSOCIATED WITH ALZHEIMER DISEASE |
|---|---|---|
| 1 | ALL | PLAU, CNTF, AVP, CRYAB, SNCB, APBA2, DHCR24, CTNND2, PSEN1, APLP1, GSK3B, APPBP2, DSCR1, MME, CRAT, AGER, NCSTN, ABCD1, BCHE, A2M, MTNR1A, APOC1, THOP1, APBA1, SERPINA3, ACHE, UBB, PIN1, TNFSF5, ADAM17, BACE2, PLCD1, APLP2, CTSK, BACE, SOD2, ADAM10, DLST, CTSG,NPY, OGDH, GYPA, PRND, CHAT, PSEN2, ACE, RAGE, GAL, APBB1, TRPM2, GSN, SNCA, BLMH, IL1A, TNFRSF6, HADH2, FHL2, ARHA, MAPK10, SLC6A4, OLR1, TGFB1, FLNB, TNF, ADAMTS5, SNCAIP, SNCG, MAPT, TFCP2, TNFRSF5, IAPP, CLU, B2M, VLDLR, GLUL, CAV2, IDE, NCKAP1, APBB2, FOS, ESR2, ACT, NGB, FPRL1, HTR2C, APCS, IGF1, CASP3, IL1B, HTR2A, GFAP, CRH, APP, SLC17A7, LRP1, PRNP, MPO, NOTCH1, S100B, MT3, CAV1, HD, BAX and CTSB. |
| 2 | Alzheimer | AVP, NCSTN, ARHA, APPBP2, HTR2A, PSEN1, DHCR24, PLAU, MTNR1A, SERPINA3, DSCR1, APBA1, APOC1, BCHE, MME, BACE2, UBB, CTNND2, APLP1, APP, SLC17A7, NCKAP1, GFAP, IGF1, SLC6A4, HD, S100B, CASP3, MPO, CNTF, GSK3B, CRH, LRP1, MT3, APBA2, CAV1, CRYAB, MAPK10, TGFB1, CHAT, TNFRSF5, CTSB, MAPT, OLR1, FLNB, |

TABLE 11-continued

| ROW # | DISEASE NAME | TARGET-GENES ASSOCIATED WITH ALZHEIMER DISEASE |
|---|---|---|
| | | CAV2, GLUL, IAPP, NGB, ACT, FOS, APBB2, TNF, SNCAIP, APLP2, PSEN2, OGDH, GYPA, ADAM17, ADAM10, ADAMTS5, BACE, TNFRSF6, ACE, HTR2C, RAGE, HADH2, FHL2, PRND, IL1A, SNCA, DLST, CTSK, TRPM2, BLMH. |

The present invention discloses a novel group of oligonucleotides, belonging to the miRNA-like oligonucleotides group, here termed GAM oligonucleotides, for which a specific complementary binding has been determined bioinformatically.

Figure 9:
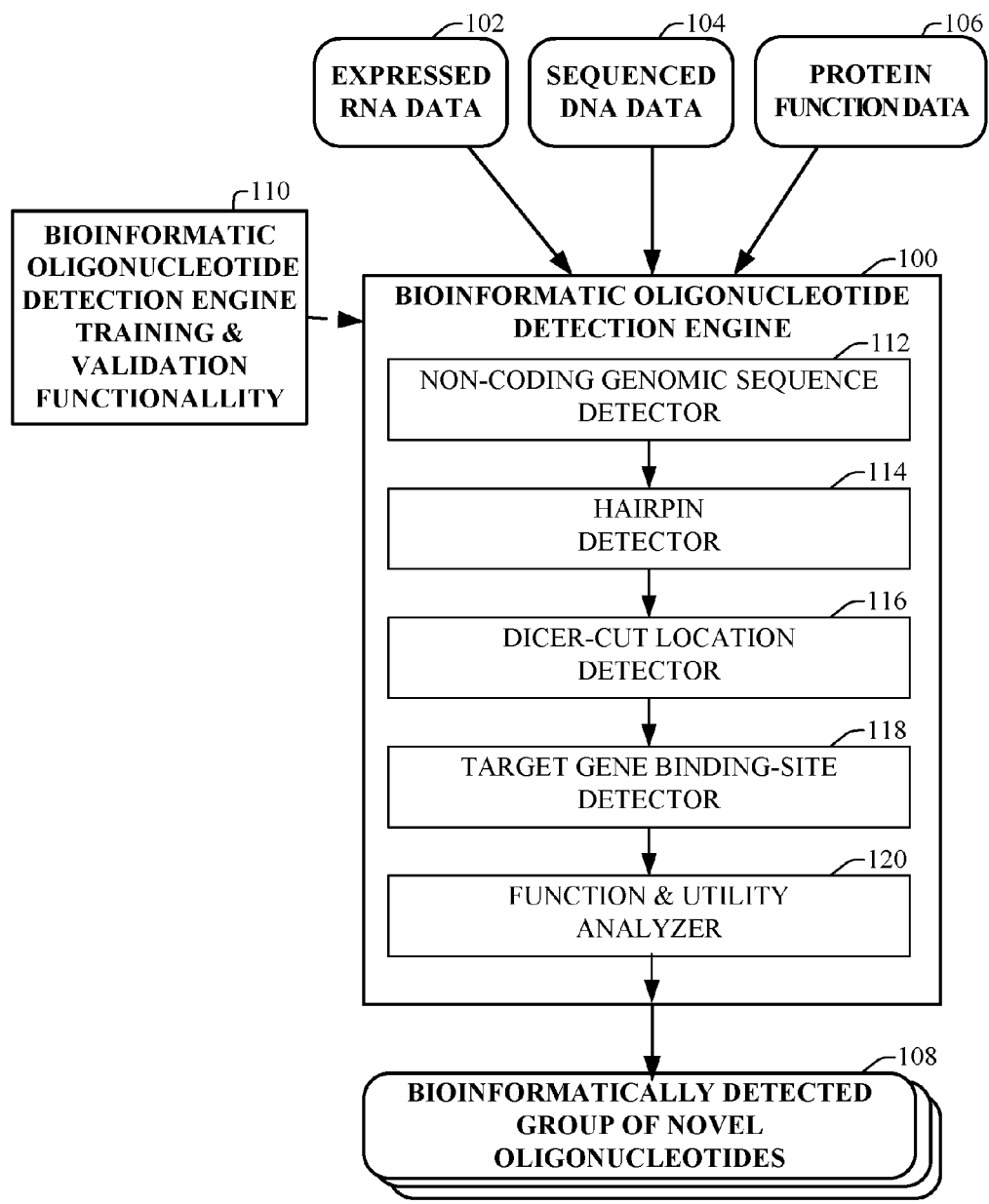
FIG. 9 is a simplified block diagram illustrating a bioinformatic oligonucleotide detection system capable of detecting oligonucleotides of the novel group of oligonucleotides of the present invention, which system is constructed and operative in accordance with a preferred embodiment of the present invention.

Reference is now made to FIG. 9 which is a simplified block diagram illustrating a bioinformatic oligonucleotide detection system and method constructed and operative in accordance with a preferred embodiment of the present invention.

An important feature of the present invention is a BIOINFORMATIC OLIGONUCLEOTIDE DETECTION ENGINE 100, which is capable of bioinformatically detecting oligonucleotides of the present invention.

The functionality of the BIOINFORMATIC OLIGONUCLEOTIDE DETECTION ENGINE 100 includes receiving EXPRESSED RNA DATA 102, SEQUENCED DNA DATA 104, and PROTEIN FUNCTION DATA 106; performing a complex process of analysis of this data as elaborated hereinbelow, and based on this analysis provides information, designated by reference numeral 108, identifying and describing features of novel oligonucleotides.

EXPRESSED RNA DATA 102 comprises published expressed sequence tags (EST) data, published mRNA data, as well as other published RNA data. SEQUENCED DNA DATA 104 comprises alphanumeric data representing genomic sequences and preferably including annotations such as information indicating the location of known protein coding regions relative to the genomic sequences.

PROTEIN FUNCTION DATA 106 comprises information from scientific publications e.g. physiological functions of known proteins and their connection, involvement and possible utility in treatment and diagnosis of various diseases.

EXPRESSED RNA DATA 102 and SEQUENCED DNA DATA 104 may preferably be obtained from data published by the National Center for Biotechnology Information (NCBI) at the National Institute of Health (NIH) (Oenuth J. P. (2000). Methods Mol. Biol. 132:301-312 (2000), herein incorporated by reference).

, as well as from various other published data sources. PROTEIN FUNCTION DATA 106 may preferably be obtained from any one of numerous relevant published data sources, such as the Online Mendelian Inherited Disease In Man (OMIM™, Hamosh et al., Nucleic Acids Res. 30: 52-55 (2002)) database developed by John Hopkins University, and also published by NCBI (2000).

Prior to or during actual detection of BIOINFORMATICALLY DETECTED GROUP OF NOVEL OLIGONUCLEOTIDES 108 by the BIOINFORMATIC OLIGONUCLEOTIDE DETECTION ENGINE 100, BIOINFORMATIC OLIGONUCLEOTIDE DETECTION ENGINE TRAINING & VALIDATION FUNCTIONALITY 110 is operative. This functionality uses one or more known miRNA oligonucleotides as a training set to train the BIOINFORMATIC OLIGONUCLEOTIDE DETECTION ENGINE 100 to bioinformatically recognize miRNA-like oligonucleotides, and their respective potential target binding sites. BIOINFORMATIC OLIGONUCLEOTIDE DETECTION ENGINE TRAINING & VALIDATION FUNCTIONALITY 110 is further described hereinbelow with reference to FIG. 10.

The BIOINFORMATIC OLIGONUCLEOTIDE DETECTION ENGINE 100 preferably comprises several modules which are preferably activated sequentially, and are described as follows:

A NON-CODING GENOMIC SEQUENCE DETECTOR 112 operative to bioinformatically detect non-protein coding genomic sequences. The NON-CODING GENOMIC SEQUENCE DETECTOR 112 is further described herein below with reference to FIGS. 11A and 11B.

A HAIRPIN DETECTOR 114 operative to bioinformatically detect genomic 'hairpin-shaped' sequences, similar to GAM FOLDED PRECURSOR RNA (FIG. 8). The HAIRPIN DETECTOR 114 is further described herein below with reference to FIGS. 12A and 12B.

A DICER-CUT LOCATION DETECTOR 116 operative to bioinformatically detect the location on a GAM FOLDED PRECURSOR RNA which is enzymatically cut by DICER COMPLEX (FIG. 8), yielding diced GAM RNA. The DICER-CUT LOCATION DETECTOR 116 is further described herein below with reference to FIGS. 13A-13C.

A TARGET GENE BINDING-SITE DETECTOR 118 operative to bioinformatically detect target genes having binding sites, the nucleotide sequence of which is partially complementary to that of a given genomic sequence, such as a nucleotide sequence cut by DICER COMPLEX. The TARGET GENE BINDING-SITE DETECTOR 118 is further described hereinbelow with reference to FIGS. 14A and 14B.

A FUNCTION & UTILITY ANALYZER 120 operative to analyze function and utility of target genes, in order to identify target genes which have a significant clinical function and utility. The FUNCTION & UTILITY ANALYZER 120 is further described hereinbelow with reference to FIG. 15.

According to a preferred embodiment of the present invention the engine 100 may employ a cluster of 40 PCs (XEON®, 2.8 GHz, with 80 GB storage each), connected by Ethernet to 8 servers (2-CPU, XEON™ 1.2-2.2 GHz, with ~200 GB storage each), combined with an 8-processor server (8-CPU, Xeon 550 Mhz w/8 GB RAM) connected via 2 HBA fiber-channels to an EMC CLARION™ 100-disks, 3.6 terabyte storage device. A preferred embodiment of the present invention may also preferably comprise software which utilizes a commercial database software program, such as MICROSOFT™ SQL Server 2000. It is appreciated that the above mentioned hardware configuration is not meant to be limiting, and is given as an illustration only. The present invention may be implemented in a wide variety of hardware and software configurations.

The present invention discloses 1708 novel oligonucleotides of the GAM group of oligonucleotides, which have been detected bioinformatically, as set forth in Tables 1-4, and 246 novel polynucleotides of the GR group of polynucleotides, which have been detected bioinformatically. Laboratory confirmation of 43 bioinformatically predicted oligonucleotides of the GAM group of oligonucleotides, and several bioinformatically predicted polynucleotides of the GR group of polynucleotides, is described hereinbelow with reference to FIGS. 21-24D.

Figure 10:
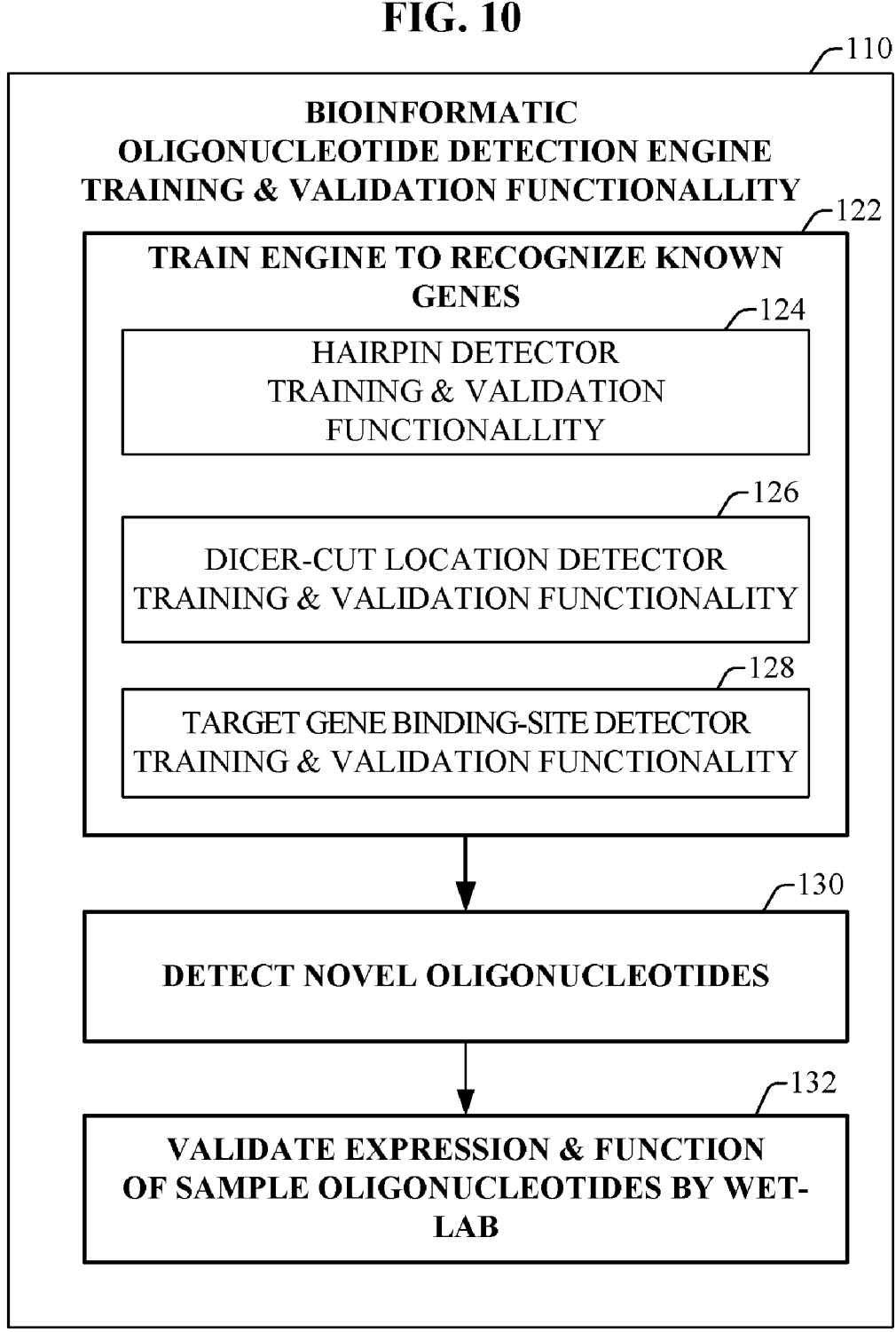
FIG. 10 is a simplified flowchart illustrating operation of a mechanism for training of a computer system to recognize the novel oligonucleotides of the present invention, which mechanism is constructed and operative in accordance with a preferred embodiment of the present invention.

Reference is now made to FIG. 10 which is a simplified flowchart illustrating operation of a preferred embodiment of the BIOINFORMATIC OLIGONUCLEOTIDE DETECTION ENGINE TRAINING & VALIDATION FUNCTIONALITY 110 described hereinabove with reference to FIG. 9.

BIOINFORMATIC OLIGONUCLEOTIDE DETECTION ENGINE TRAINING & VALIDATION FUNCTIONALITY 110 begins by training the BIOINFORMATIC OLIGONUCLEOTIDE DETECTION ENGINE 100 (FIG. 9) to recognize one or more known miRNA oligonucleotides, as designated by reference numeral 122. This training step comprises HAIRPIN DETECTOR TRAINING & VALIDATION FUNCTIONALITY 124, further described hereinbelow with reference to FIG. 12A, DICER-CUT LOCATION DETECTOR TRAINING & VALIDATION FUNCTIONALITY 126, further described hereinbelow with reference to FIGS. 13A and 13B, and TARGET GENE BINDING-SITE DETECTOR TRAINING & VALIDATION FUNCTIONALITY 128, further described hereinbelow with reference to FIG. 14A.

Next, the BIOINFORMATIC OLIGONUCLEOTIDE DETECTION ENGINE TRAINING & VALIDATION FUNCTIONALITY 110 is operative bioinformatically detect novel oligonucleotides, using BIOINFORMATIC OLIGONUCLEOTIDE DETECTION ENGINE 100 (FIG. 9), as designated by reference numeral 130. Wet lab experiments are preferably conducted in order to validate expression and preferably function of some samples of the novel oligonucleotides detected by the BIOINFORMATIC OLIGONUCLEOTIDE DETECTION ENGINE 100, as designated by reference numeral 132. FIGS. 22A-24D illustrate examples of wet-lab validation of the above mentioned sample novel oligonucleotides bioinformatically detected in accordance with a preferred embodiment of the present invention.

Figure 11A:
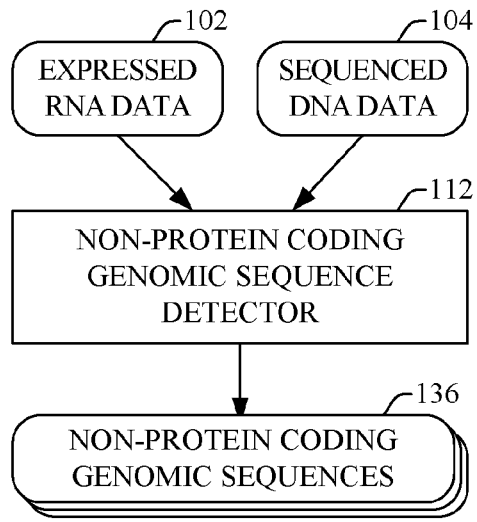
FIG. 11A is a simplified block diagram of a non-coding genomic sequence detector constructed and operative in accordance with a preferred embodiment of the present invention.
Figure 11B:
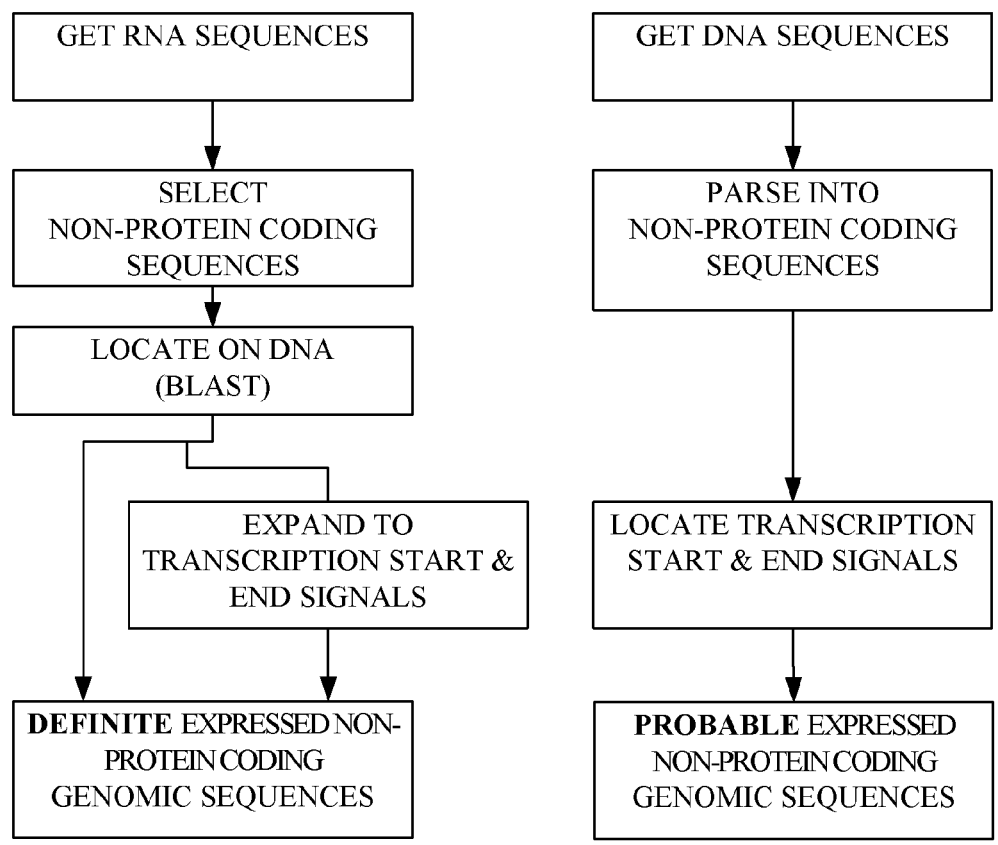
FIG. 11B is a simplified flowchart illustrating operation of a non-coding genomic sequence detector constructed and operative in accordance with a preferred embodiment of the present invention.

Reference is now made to FIG. 11A which is a simplified block diagram of a preferred implementation of the NON-CODING GENOMIC SEQUENCE DETECTOR 112 described hereinabove with reference to FIG. 9. The NON-PROTEIN CODING GENOMIC SEQUENCE DETECTOR 112 preferably receives at least two types of published genomic data: EXPRESSED RNA DATA 102 and SEQUENCED DNA DATA 104. The EXPRESSED RNA DATA 102 may include, inter alia, EST data, EST clusters data, EST genome alignment data and mRNA data. Sources for EXPRESSED RNA DATA 102 include NCBI dbEST, NCBI UniGene clusters and mapping data, and TIGR (Kirkness F. and Kerlavage, A. R., Methods Mol. Biol. 69:261-268 (1997)) gene indices. SEQUENCED DNA DATA 104 may include sequence data (FASTA format files), and feature annotations (GenBank file format) mainly from NCBI databases. Based on the above mentioned input data, the NON-PROTEIN CODING GENOMIC SEQUENCE DETECTOR 112 produces a plurality of NON-PROTEIN CODING GENOMIC SEQUENCES 136. Preferred operation of the NON-PROTEIN CODING GENOMIC SEQUENCE DETECTOR 112 is described hereinbelow with reference to FIG. 11B Reference is now made to FIG. 11B which is a simplified flowchart illustrating a preferred operation of the NONCODING GENOMIC SEQUENCE DETECTOR 112 of FIG. 9. Detection of NON-PROTEIN CODING GENOMIC SEQUENCES 136, generally preferably progresses along one of the following two paths:

A first path for detecting NON-PROTEIN CODING GENOMIC SEQUENCES 136 (FIG. 11A) begins with receipt of a plurality of known RNA sequences, such as EST data. Each RNA sequence is first compared with known protein-coding DNA sequences, in order to select only those RNA sequences which are non-protein coding, i.e. intergenic or intronic sequences. This can preferably be performed by using one of many alignment algorithms known in the art, such as BLAST (Altschul et al., J. Mol. Biol. 215:403-410 (1990)). This sequence comparison preferably also provides localization of the RNA sequence on the DNA sequences.

Alternatively, selection of non-protein coding RNA sequences and their localization on the DNA sequences can be performed by using publicly available EST cluster data and genomic mapping databases, such as the UNIGENE database published by NCBI or the TIGR database. Such databases, map expressed RNA sequences to DNA sequences encoding them, find the correct orientation of EST sequences, and indicate mapping of ESTs to protein coding DNA regions, as is well known in the art. Public databases, such as TIGR, may also be used to map an EST to a cluster of ESTs, known in the art as Tentative Human Consensus and assumed to be expressed as one segment. Publicly available genome annotation databases, such as NCBIs GenBank, may also be used to deduce expressed intronic sequences.

Optionally, an attempt may be made to "expand" the non-protein RNA sequences thus found, by searching for transcription start and end signals, respectively upstream and downstream of the location of the RNA on the DNA, as is well known in the art.

A second path for detecting NON-PROTEIN CODING GENOMIC SEQUENCES 136 (FIG. 11A) begins with receipt of DNA sequences. The DNA sequences are parsed into non protein coding sequences, using published DNA annotation data, by extracting those DNA sequences which are between known protein coding sequences. Next, transcription start and end signals are sought. If such signals are found, and depending on their robustness, probable expressed non-protein coding genomic sequences are obtained. Such approach is especially useful for identifying novel GAM oligonucleotides which are found in proximity to other known miRNA oligonucleotides, or other wet-lab validated GAM oligonucleotides. Since, as described hereinbelow with reference to FIG. 16, GAM oligonucleotides are frequently found in clusters, sequences located near known miRNA oligonucleotides are more likely to contain novel GAM oligonucleotides. Optionally, sequence orthology, i.e. sequence conservation in an evolutionary related species, may be used to select genomic sequences having a relatively high probability of containing expressed novel GAM oligonucleotides.

Figure 12A:
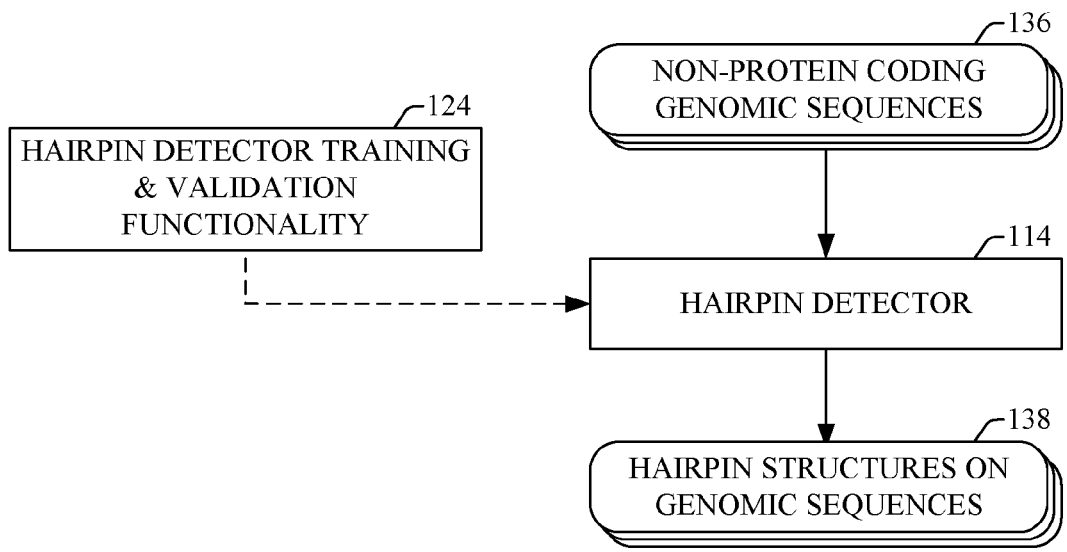
FIG. 12A is a simplified block diagram of a hairpin detector constructed and operative in accordance with a preferred embodiment of the present invention.

Reference is now made to FIG. 12A which is a simplified block diagram of a preferred implementation of the HAIRPIN DETECTOR 114 described hereinabove with reference to FIG. 9.

The goal of the HAIRPIN DETECTOR 114 is to detect hairpin-shaped genomic sequences, similar to those of known miRNA oligonucleotides. A hairpin-shaped genomic sequence is a genomic sequence, having a first half which is at least partially complementary to a second half thereof, which causes the halves to folds onto themselves, thereby forming a hairpin structure, as mentioned hereinabove with reference to FIG. 8.

The HAIRPIN DETECTOR 114 (FIG. 9) receives a plurality of NON-PROTEIN CODING GENOMIC SEQUENCES 136 (FIG. 11A). Following operation of HAIRPIN DETECTOR TRAINING & VALIDATION FUNCTIONALITY 124 (FIG. 10), the HAIRPIN DETECTOR 114 is operative to detect and output hairpin-shaped sequences, which are found in the NON-PROTEIN CODING GENOMIC SEQUENCES 136. The hairpin-shaped sequences detected by the HAIRPIN DETECTOR 114 are designated HAIRPINS STRUCTURES ON GENOMIC SEQUENCES 138. A preferred mode of operation of the HAIRPIN DETECTOR 114 is described hereinbelow with reference to FIG. 12B.

HAIRPIN DETECTOR TRAINING & VALIDATION FUNCTIONALITY 124 includes an iterative process of applying the HAIRPIN DETECTOR 114 to known hairpin shaped miRNA precursor sequences, calibrating the HAIRPIN DETECTOR 114 such that it identifies a training set of known hairpin-shaped miRNA precursor sequences, as well as other similarly hairpin-shaped sequences. In a preferred embodiment of the present invention, the HAIRPIN DETECTOR TRAINING & VALIDATION FUNCTIONALITY 124 trains the HAIRPIN DETECTOR 114 and validates each of the steps of operation thereof described hereinbelow with reference to FIG. 12B.

The HAIRPIN DETECTOR TRAINING & VALIDATION FUNCTIONALITY 124 preferably uses two sets of data: the aforesaid training set of known hairpin-shaped miRNA precursor sequences, such as hairpin-shaped miRNA precursor sequences of 440 miRNA oligonucleotides of *H. sapiens, M. musculus, C. elegans, C. Brigssae* and *D. Melanogaster*, annotated in the RFAM database (Griffiths-Jones, 2003), and a large background set of about 350,000 hairpin-shaped sequences found in expressed non-protein coding genomic sequences. The background set is expected to comprise some valid, previously undetected hairpin-shaped miRNA-like precursor sequences, and many hairpin-shaped sequences which are not hairpin-shaped miRNA-like precursors.

In order to validate the performance of the HAIRPIN DETECTOR 114 (FIG. 9), preferably a variation of the k-fold cross validation method (Tom M. Mitchell, Machine Learning, McGraw Hill (1997)), is employed. This preferred validation method is well adapted to deal with the training set, which includes large numbers of similar or identical miRNAs. The training set is therefore preferably initially divided into groups of miRNAs such that any two miRNAs that belong to different groups have an Edit Distance score of at least D=3, i.e. they differ by at least 3 editing steps (Dan Gusfield, Algorithms on strings, trees, and sequences: computer science and computational biology, Cambridge University Press, 1997). Next, the groups are preferably classified into k sets of groups. Standard k-fold cross validation is preferably performed on these sets, preferably using k=5, such that the training set and the test set include at least one sequence from each of the groups. It is appreciated that without the prior grouping, standard cross validation methods incorrectly indicate much higher performance results for the predictors due to the redundancy of training examples within the genome of a species and across genomes of different species.

In a preferred embodiment of the present invention, using the abovementioned validation methodology, the efficacy of the HAIRPIN DETECTOR 114 (FIG. 9) is confirmed. For example, when a similarity threshold is chosen such that 90% of the known hairpin-shaped miRNA precursors are successfully predicted, only 11% of the approximately 342,880 background set of hairpin-shaped sequences are predicted to be hairpin-shaped miRNA-like precursors.

Figure 12B:
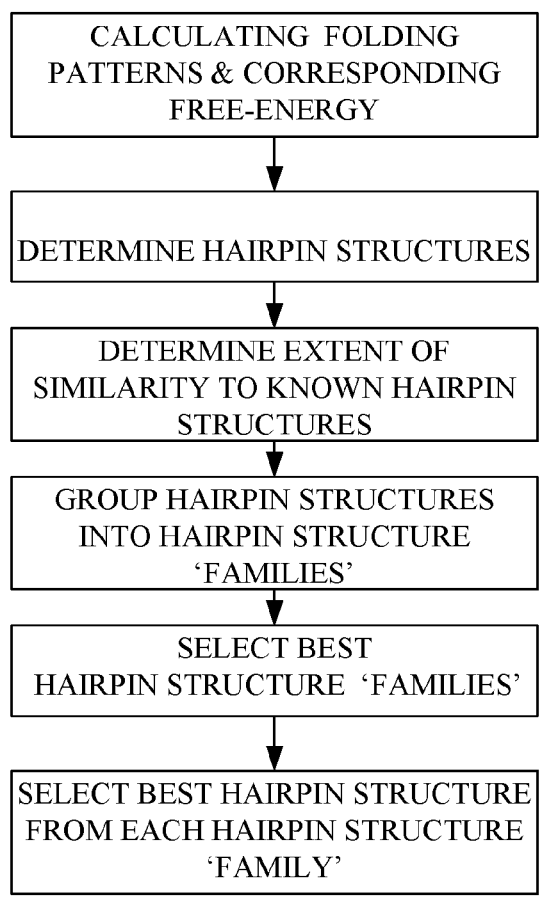
FIG. 12B is a simplified flowchart illustrating operation of a hairpin detector constructed and operative in accordance with a preferred embodiment of the present invention.

Reference is now made to FIG. 12B which is a simplified flowchart illustrating preferred operation of the HAIRPIN DETECTOR 114 of FIG. 9. The HAIRPIN DETECTOR 114 preferably initially uses a secondary structure folding algorithm based on free-energy minimization, such as the MFOLD algorithm, described in Mathews et al. J. Mol. Biol. 288:911-940 (1999) and Zuker, M. Nucleic Acids Res. 31: 3406-3415. (2003), the disclosure of which is hereby incorporated by reference. This algorithm is operative to calculate probable secondary structure folding patterns of the NON-PROTEIN CODING GENOMIC SEQUENCES 136 (FIG. 11A) as well as the free-energy of each of these probable secondary folding patterns. The secondary structure folding algorithm, such as the MFOLD algorithm (Mathews, 1997; Zuker 2003), typically provides a listing of the base-pairing of the folded shape, i.e. a listing of each pair of connected nucleotides in the sequence.

Next, the HAIRPIN DETECTOR 114 analyzes the results of the secondary structure folding patterns, in order to determine the presence and location of hairpin folding structures. The goal of this second step is to assess the base-pairing listing provided by the secondary structure folding algorithm, in order to determine whether the base-pairing listing describes one or more hairpin type bonding pattern. Preferably, sequence segment corresponding to a hairpin structure is then separately analyzed by the secondary structure folding algorithm in order to determine its exact folding pattern and free-energy.

The HAIRPIN DETECTOR 114 then assesses the hairpin structures found by the previous step, comparing them to hairpin structures of known miRNA precursors, using various characteristic hairpin structure features such as length of the hairpin structure, length of the loop of mismatched nucleotides at its center, its free-energy and its thermodynamic stability, the amount and type of mismatched nucleotides and the existence of sequence repeat-elements. Only hairpins that bear statistically significant resemblance to the training set of hairpin structures of known miRNA precursors, according to the abovementioned parameters, are accepted.

In a preferred embodiment of the present invention, similarity to the training set of hairpin structures of known miRNA precursors is determined using a "similarity score" which is calculated using a weighted sum of terms, where each term is a function of one of the abovementioned hairpin structure features. The parameters of each function are learned from the set of hairpin structures of known miRNA precursors, as described hereinabove with reference to HAIRPIN DETECTOR TRAINING & VALIDATION FUNCTIONALITY 124 (FIG. 10). The weight of each term in the similarity score is optimized so as to achieve maximized separation between the distribution peaks of similarity scores validated miRNA-precursor hairpin structures, and the distribution of similarity scores of hairpin structures detected in the background set mentioned hereinabove with reference to FIG. 12B.

In an alternative preferred embodiment of the present invention, the step described in the preceding paragraph may be split into two stages. A first stage implements a simplified scoring method, typically based on thresholding a subset of the hairpin structure features described hereinabove, and may employ a minimum threshold for hairpin structure length and a maximum threshold for free energy. A second stage is preferably more stringent, and preferably employs a full calculation of the weighted sum of terms described hereinabove. The second stage preferably is performed only on the subset of hairpin structures that survived the first stage.

The HAIRPIN DETECTOR 114 also attempts to select hairpin structures whose thermodynamic stability is similar to that of hairpin structures of known miRNA precursors. This may be achieved in various ways. A preferred embodiment of the present invention utilizes the following methodology, preferably comprising three logical steps:

First, the HAIRPIN DETECTOR 114 attempts to group hairpin structures into "families" of closely related hairpin structures. As is known in the art, a secondary structure folding algorithm typically provides multiple alternative folding patterns, for a given genomic sequence and indicates the free energy of each alternative folding pattern. It is a particular feature of the present invention that the HAIRPIN DETECTOR 114 preferably assesses the various hairpin structures appearing in the various alternative folding patterns and groups hairpin structures which appear at identical or similar sequence locations in various alternative folding patterns into common sequence location based "families" of hairpins. For example, all hairpin structures whose center is within 7 nucleotides of each other may be grouped into a family". Hairpin structures may also be grouped into a family" if their nucleotide sequences are identical or overlap to a predetermined degree.

It is also a particular feature of the present invention that the hairpin structure "families" are assessed in order to select only those families which represent hairpin structures that are as thermodynamically stable as those of hairpin structures of known miRNA precursors. Preferably only families which are represented in at least a selected majority of the alternative secondary structure folding patterns, typically 65%, 80% or 100% are considered to be sufficiently stable.

It is an additional particular feature of the present invention that the most suitable hairpin structure is selected from each selected family. For example, a hairpin structure which has the greatest similarity to the hairpin structures appearing in alternative folding patterns of the family may be preferred. Alternatively or additionally, the hairpin structures having relatively low free energy may be preferred.

Alternatively or additionally considerations of homology to hairpin structures of other organisms and the existence of clusters of thermodynamically stable hairpin structures located adjacent to each other along a sequence may be important in selection of hairpin structures. The tightness of the clusters in terms of their location and the occurrence of both homology and clusters may be of significance.

Figure 13A:
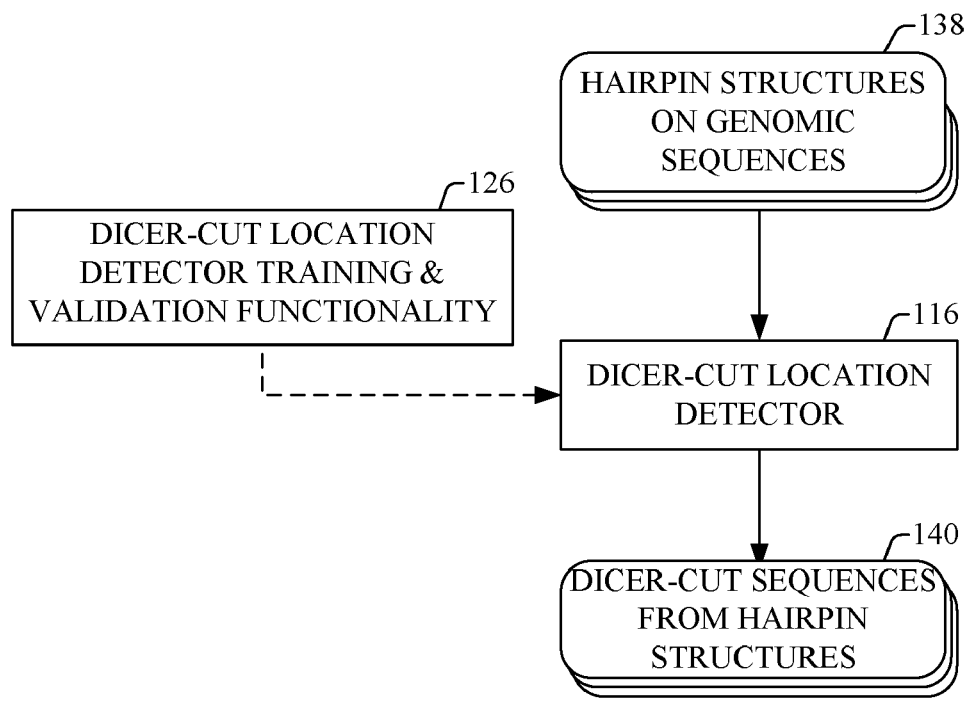
FIG. 13A is a simplified block diagram of a dicer-cut location detector constructed and operative in accordance with a preferred embodiment of the present invention.
Figure 13B:
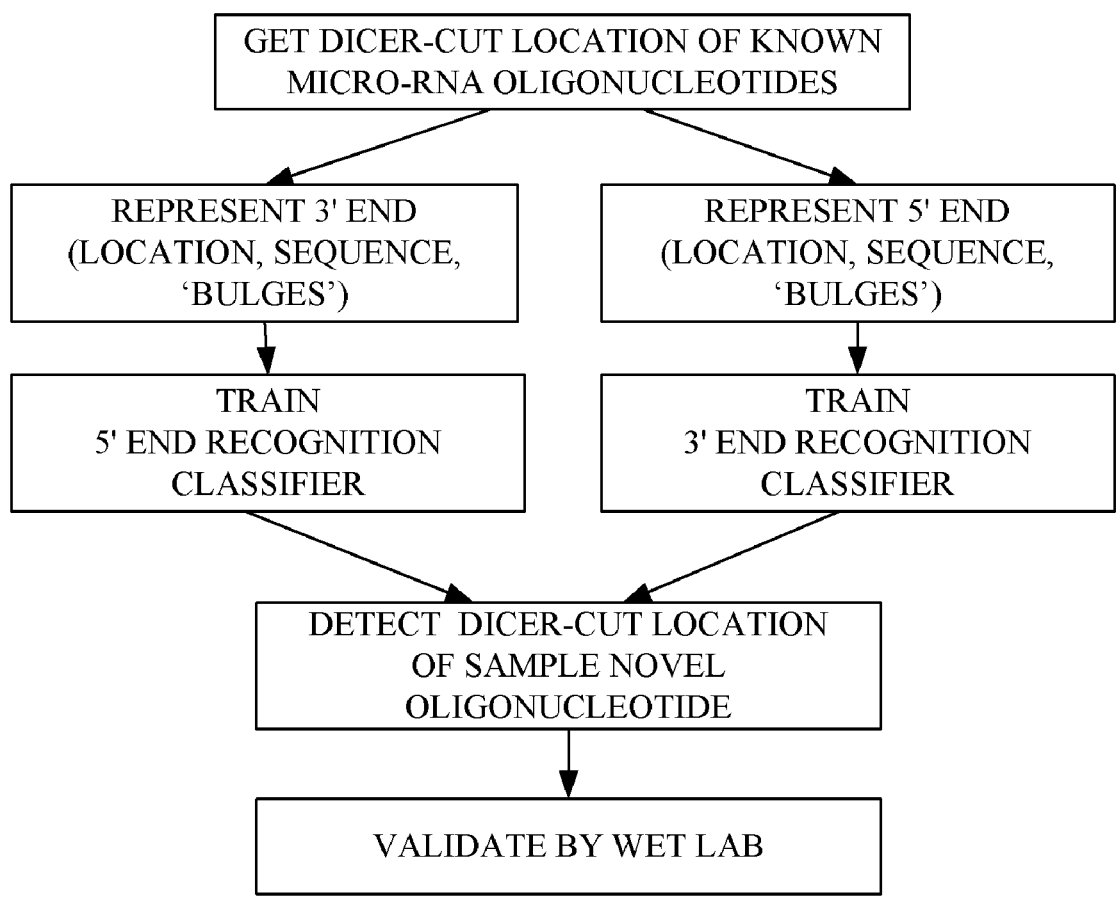
FIG. 13B is a simplified flowchart illustrating training of a dicer-cut location detector constructed and operative in accordance with a preferred embodiment of the present invention.
Figure 13C:
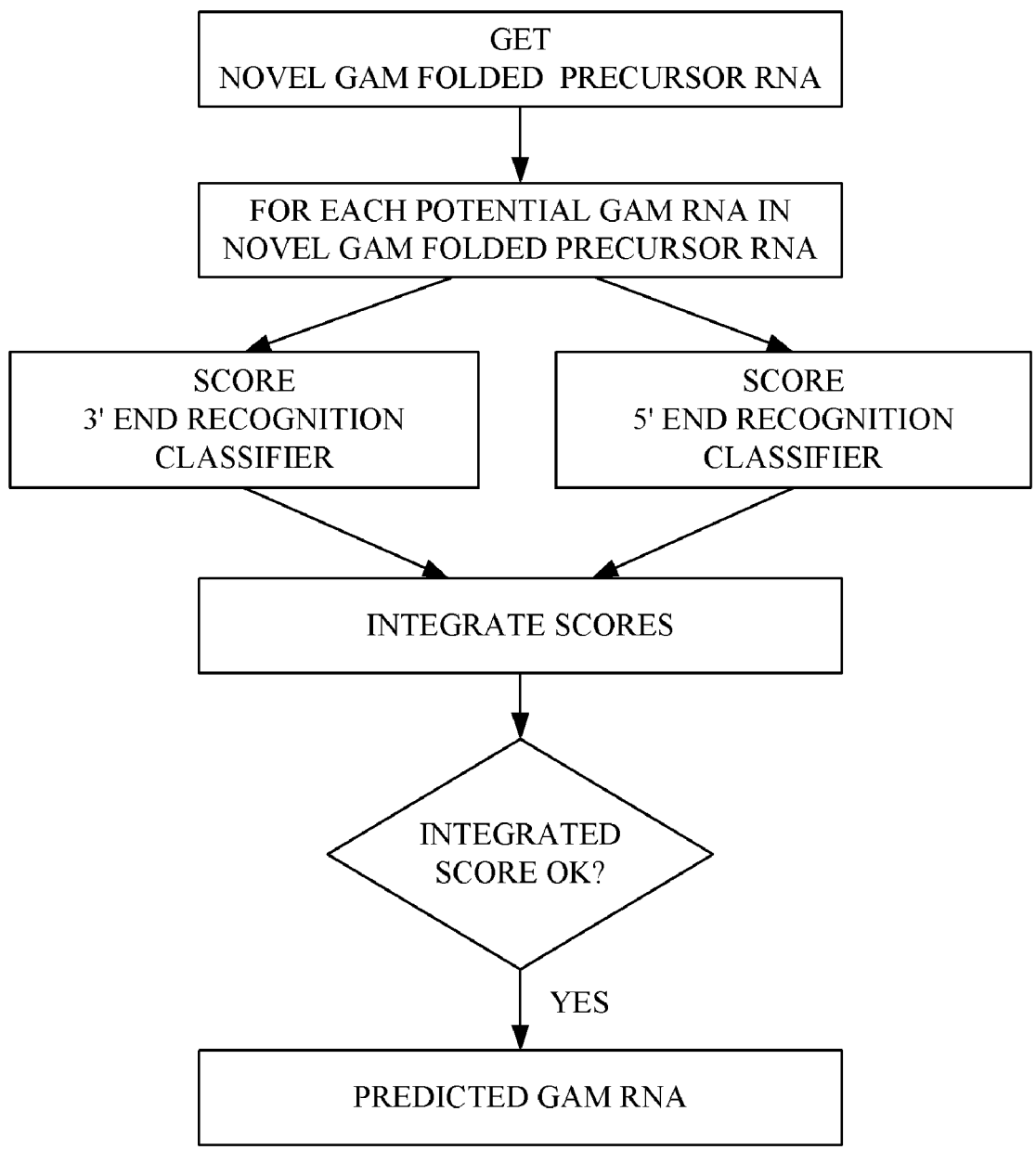
FIG. 13C is a simplified flowchart illustrating operation of a dicer-cut location detector constructed and operative in accordance with a preferred embodiment of the present invention.

Reference is now made to FIGS. 13A-13C which together describe the structure and operation of the DICER-CUT LOCATION DETECTOR 116, described hereinabove with FIG. 9.

FIG. 13A is a simplified block diagram of a preferred implementation 116. The goal of the DICER-CUT LOCATION DETECTOR 116 is to detect the location in which the DICER COMPLEX, described hereinabove with reference to FIG. 8, dices GAM FOLDED PRECURSOR RNA, yielding GAM RNA.

The DICER-CUT LOCATION DETECTOR 116 therefore receives a plurality of HAIRPIN STRUCTURES ON GENOMIC SEQUENCES 138 (FIG. 12A), and, following operation of DICER-CUT LOCATION DETECTOR TRAINING & VALIDATION FUNCTIONALITY 126 (FIG. 10), is operative to detect a plurality of DICER-CUT SEQUENCES FROM HAIRPIN STRUCTURES 140.

Reference is now made to FIG. 13B which is a simplified flowchart illustrating a preferred implementation of DICER-CUT LOCATION DETECTOR TRAINING & VALIDATION FUNCTIONALITY 126.

A general goal of the DICER-CUT LOCATION DETECTOR TRAINING & VALIDATION FUNCTIONALITY 126 is to analyze the dicer-cut locations of known diced miRNA on respective hairpin shaped miRNA precursors in order to determine a common pattern in these locations, which can be used to predict dicer cut locations on GAM folded precursor RNAs.

The dicer-cut locations of known miRNA precursors are obtained and studied. Locations of the 5' and/or 3' ends of the known diced miRNAs are preferably represented by their respective distances from the 5' end of the corresponding hairpin shaped miRNA precursor. Additionally or alternatively, the 5' and/or 3' ends of the known diced miRNAs are preferably represented by the relationship between their locations and the locations of one or more nucleotides along the hairpin shaped miRNA precursor. Additionally or alternatively, the 5' and/or 3' ends of the known diced miRNAs are preferably represented by the relationship between their locations and the locations of one or more bound nucleotide pairs along the hairpin shaped miRNA precursor. Additionally or alternatively, the 5' and/or 3' ends of the known diced miRNAs are preferably represented by the relationship between their locations and the locations of one or more mismatched nucleotide pairs along the hairpin shaped miRNA precursor. Additionally or alternatively, the 5' and/or 3' ends of the known diced miRNAs are preferably represented by the relationship between their locations and the locations of one or more unmatched nucleotides along the hairpin shaped miRNA precursor. Additionally or alternatively, locations of the 5' and/or 3' ends of the known diced miRNAs are preferably represented by their respective distances from the loop located at the center of the corresponding hairpin shaped miRNA precursor.

One or more of the foregoing location metrics may be employed in the training and validation functionality. Additionally, metrics related to the nucleotide content of the diced miRNA and/or of the hairpin shaped miRNA precursor may be employed.

In a preferred embodiment of the present invention, DICER-CUT LOCATION DETECTOR TRAINING & VALIDATION FUNCTIONALITY 126 preferably employs standard machine learning techniques known in the art of machine learning for analysis of existing patterns in a given "training set" of examples. These techniques are capable, to a certain degree, of detecting similar patterns in other, previously unseen examples. Such machine learning techniques include, but are not limited to neural networks, Bayesian networks, Support Vector Machines (SVM), Genetic Algorithms, Markovian modeling, Maximum Likelihood modeling, Nearest Neighbor algorithms, Decision trees and other techniques, as is well known in the art.

In accordance with one embodiment of the present invention, machine learning predictors, such as a Support Vector Machine (SVM) predictor, are applied to the aforementioned training set and are operative, for example to test every possible nucleotide on a hairpin as a candidate for being the 5' end or the 3' end of a diced GAM RNA. More preferred machine learning predictors include predictors based on Nearest Neighbor, Bayesian modeling, and K-nearest-neighbor algorithms. A training set of the known miRNA precursor sequences is preferably used for training multiple separate classifiers or predictors, each of which produces a model for the 5' and/or 3' end locations of a diced miRNA with respect to its hairpin precursor. The models take into account one or more of the various miRNA location metrics described above.

Performance of the resulting predictors, evaluated on the abovementioned validation set of 440 published miRNAs using k-fold cross validation (Mitchell, 1997) with k=3, is found to be as follows: in 70% of known miRNAs 5'-end location is correctly determined by an SVM predictor within up to 2 nucleotides; a Nearest Neighbor (EDIT DISTANCE) predictor achieves 56% accuracy (247/440); a Two-Phased predictor that uses Bayesian modeling (TWO PHASED) achieves 80% accuracy (352/440), when only the first phase is used. When the second phase (strand choice) is implemented by a nave Bayesian model the accuracy is 55% (244/440), and when the K-nearest-neighbor modeling is used for the second phase, 374/440 decision are made and the accuracy is 65% (242/374). A K-near-nearest-neighbor predictor (FIRST-K) achieves 61% accuracy (268/440). The accuracies of all predictors are considerably higher on top scoring subsets of published miRNA.

Finally, in order to validate the efficacy and accuracy of the DICER-CUT LOCATION DETECTOR 116, a sample of novel oligonucleotides detected thereby is preferably selected, and validated by wet lab. Laboratory results validating the efficacy of the DICER-CUT LOCATION DETECTOR 116 are described hereinbelow with reference to FIGS. 21-24D.

Reference is now made to FIG. 13C which is a simplified flowchart illustrating operation of DICER-CUT LOCATION DETECTOR 116 (FIG. 9), constructed and operative in accordance with a preferred embodiment of the present invention. The DICER CUT LOCATION DETECTOR 116 preferably comprises a machine learning computer program module, which is trained to recognize dicer-cut locations on known hairpin-shaped miRNA precursors, and based on this training, is operable to detect dicer-cut locations of novel GAM RNAs (FIG. 8) on GAM FOLDED PRECURSOR RNAs (FIG. 8). In a preferred embodiment of the present invention, the dicer-cut location module preferably utilizes machine learning algorithms, such as known Support Vector Machine (SVM) and more preferably: known Bayesian modeling, Nearest Neighbors, and K-nearest-neighbor algorithms.

When initially assessing a novel GAM FOLDED PRECURSOR RNA, all 19-24 nucleotide long segments thereof are initially considered as "potential GAM RNAs", since the dicer-cut location is initially unknown.

For each such potential GAM RNA, the location of its 5' end or the locations of its 5' and 3' ends are scored by at least one recognition classifier or predictor.

In a preferred embodiment of the present invention, the DICER-CUT LOCATION DETECTOR 116 (FIG. 9) may use a Support Vector Machine predictor trained on and operating on features such as the following:

Locations of the 5' and/or 3' ends of the known diced miRNAs, which are preferably represented by their respective distances from the 5' end of the corresponding hairpin shaped miRNA precursor. Additionally or alternatively, the 5' and/or 3' ends of the known diced miRNAs are preferably represented by the relationship between their locations and the locations of one or more nucleotides along the hairpin shaped miRNA precursor. Additionally or alternatively, the 5' and/or 3' ends of the known diced miRNAs are preferably represented by the relationship between their locations and the locations of one or more bound nucleotide pairs along the hairpin shaped miRNA precursor. Additionally or alternatively, the 5' and/or 3' ends of the known diced miRNAs are preferably represented by the relationship between their locations and the locations of one or more mismatched nucleotide pairs along the hairpin shaped miRNA precursor. Additionally or alternatively, the 5' and/or 3' ends of the known diced miRNAs are preferably represented by the relationship between their locations and the locations of one or more unmatched nucleotides along the hairpin shaped miRNA precursor. Additionally or alternatively, locations of the 5' and/or 3' ends of the known diced miRNAs are preferably represented by their respective distances from the loop located at the center of the corresponding hairpin shaped miRNA precursor; and secondarily Metrics related to the nucleotide content of the diced miRNA and/or of the hairpin shaped miRNA precursor.

In another preferred embodiment of the present invention, the DICER-CUT LOCATION DETECTOR 116 (FIG. 9) preferably employs an "EDIT DISTANCE" predictor, which seeks sequences that are similar to those of known miRNAs, utilizing a Nearest Neighbor algorithm, where a similarity metric between two sequences is a variant of the Edit Distance algorithm (Dan Gusfield, Algorithms on strings, trees, and sequences: computer science and computational biology, Cambridge University Press, 1997). The EDIT DISTANCE predictor is based on an observation that miRNA oligonucleotides tend to form clusters, the members of which show marked sequence similarity.

In yet another preferred embodiment of the present invention, the DICER-CUT LOCATION DETECTOR 116 (FIG. 9) preferably uses a "TWO PHASE" predictor, which predicts the dicer-cut location in two distinct phases: (a) selecting a double-stranded segment of the GAM FOLDED PRECURSOR RNA (FIG. 8) comprising the GAM RNA by nave Bayesian modeling and (b) detecting which strand of the double-stranded segment contains GAM RNA (FIG. 8) by employing either nave or by K-nearest-neighbor modeling. K-nearest-neighbor modeling is a variant of the 'FIRST-K' predictor described hereinbelow, with parameters optimized for this specific task. The 'TWO PHASE' predictor may be operated in two modes: either utilizing only the first phase and thereby producing two alternative dicer-cut location predictions, or utilizing both phases and thereby producing only one final dicer-cut location.

In still another preferred embodiment of the present invention, the DICER-CUT LOCATION DETECTOR 116 preferably uses a "FIRST-K" predictor, which utilizes a K-nearest-neighbor algorithm. The similarity metric between any two sequences is $1-E/L$, where L is a parameter, preferably 8-10 and E is the edit distance between the two sequences, taking into account only the first L nucleotides of each sequence. If the K-nearest-neighbor scores of two or more locations on the GAM FOLDED PRECURSOR RNA (FIG. 8) are not significantly different, these locations are further ranked by a Bayesian model, similar to the one described hereinabove.

The TWO PHASE and FIRST-K predictors preferably are trained on and operate on features such as the following:

Locations of the 5' and/or 3' ends of the known diced miRNAs, which are preferably represented by their respective distances from the 5' end of the corresponding hairpin shaped miRNA precursor. Additionally or alternatively, the 5' and/or 3' ends of the known diced miRNAs are preferably represented by the relationship between their locations and the locations of one or more nucleotides along the hairpin shaped miRNA precursor. Additionally or alternatively, the 5' and/or 3' ends of the known diced miRNAs are preferably represented by the relationship between their locations and the locations of one or more bound nucleotide pairs along the hairpin shaped miRNA precursor. Additionally or alternatively, the 5' and/or 3' ends of the known diced miRNAs are preferably represented by the relationship between their locations and the locations of one or more mismatched nucleotide pairs along the hairpin shaped miRNA precursor. Additionally or alternatively, the 5' and/or 3' ends of the known diced miRNAs are preferably represented by the relationship between their locations and the locations of one or more unmatched nucleotides along the hairpin shaped miRNA precursor. Additionally or alternatively, locations of the 5' and/or 3' ends of the known diced miRNAs are preferably represented by their respective distances from the loop located at the center of the corresponding hairpin shaped miRNA precursor; and secondarily Metrics related to the nucleotide content of the diced miRNA and/or of the hairpin shaped miRNA precursor.

In accordance with an embodiment of the present invention scores of two or more of the abovementioned classifiers or predictors are integrated, yielding an integrated score for each "potential GAM RNA". As an example, FIG. 13C illustrates integration of scores from two classifiers, a 3' end recognition classifier and a 5' end recognition classifier, the scores of which are integrated to yield an integrated score. Most preferably, the INTEGRATED SCORE of FIG. 13C preferably implements a "best-of-breed" approach employing a pair of classifiers and accepting only "potential GAM RNAs" that score highly on one of the above mentioned "EDIT DISTANCE", or "TWO-PHASE" predictors. In this context, "high scores" means scores which have been demonstrated to have low false positive value when scoring known miRNA oligonucleotides. Alternatively, the INTEGRATED SCORE may be derived from operation of more or less than two classifiers.

The INTEGRATED SCORE is evaluated as follows: (a) the "potential GAM RNA" having the highest score is preferably taken to be the most probable GAM RNA, and (b) if the integrated score of this most probable GAM RNA is higher than a pre-defined threshold, then the most probable GAM RNA is accepted as a PREDICTED GAM RNA. Preferably, this evaluation technique is not limited to the highest scoring potential GAM RNA.

Figure 14A:
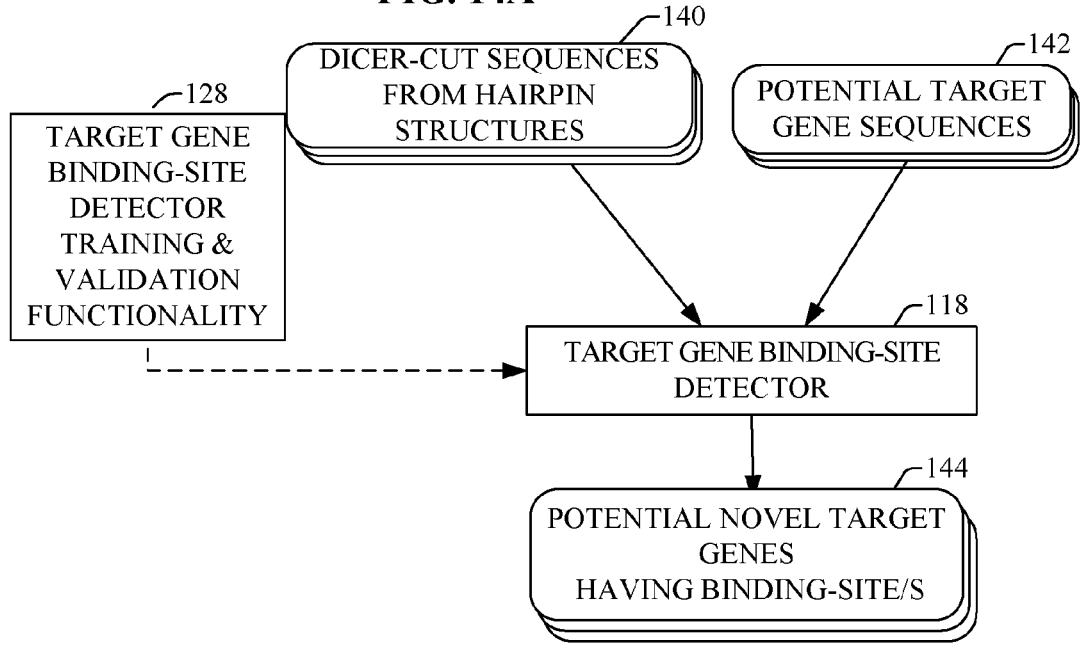
FIG. 14A is a simplified block diagram of a target gene binding-site detector constructed and operative in accordance with a preferred embodiment of the present invention.

Reference is now made to FIG. 14A which is a simplified block diagram of a preferred implementation of the TARGET GENE BINDING-SITE DETECTOR 118 described hereinabove with reference to FIG. 9. The goal of the TARGET GENE BINDING-SITE DETECTOR 118 is to detect one or more binding sites such as BINDING SITE I, BINDING SITE II and BINDING SITE III (FIG. 8) located in untranslated regions of the mRNA of a known gene, the nucleotide sequence of which binding sites is partially or fully complementary to a GAM RNA, thereby determining that the above mentioned known gene is a target gene thereof.

The TARGET GENE BINDING-SITE DETECTOR 118 (FIG. 9) receives a plurality of DICER-CUT SEQUENCES FROM HAIRPIN STRUCTURES 140 (FIG. 13A), and a plurality of POTENTIAL TARGET GENE SEQUENCES 142 which are derived from SEQUENCED DNA DATA 104 (FIG. 9).

TARGET GENE BINDING-SITE DETECTOR TRAINING & VALIDATION FUNCTIONALITY 128 (FIG. 10) is operative to train the TARGET GENE BINDING-SITE DETECTOR on known miRNAs and their respective target genes. A sequence comparison of sequences of known miRNA oligonucleotides to sequences of known binding sites of known target thereof is performed by utilizing BLAST or other algorithms such as EDIT DISTANCE.

The results are preferably employed to define a threshold based on scoring distinctions between known miRNA binding sites and sequences which are known not to be miRNA binding sites. This threshold is used during operation of TARGET GENE BINDING-SITE DETECTOR 118 to distinguish between miRNA-like binding sites of potential GAM RNA and other sequences.

Next, the binding sites are expanded, and determinations are made whether if nucleotide sequences immediately adjacent to the binding sites found by the sequence comparison algorithm (e.g. BLAST or EDIT DISTANCE), may improve the match. Free-energy and spatial structure are computed for the resulting binding sites. Binding sites which are clustered are strongly preferred and binding sites found in evolutionarily conserved sequences may also be preferred. Free energy, spatial structure and the above preferences are reflected in scoring.

The resulting scores, characteristic of known binding sites (e.g. binding sites of known miRNA oligonucleotides Lin-4 and Let-7 to target genes Lin-14, Lin-41, Lin 28 etc.), may be employed for detection of binding-sites of novel GAM RNAs.

Following operation of TARGET GENE BINDING-SITE DETECTOR TRAINING & VALIDATION FUNCTIONALITY 128 (FIG. 10), the TARGET GENE BINDING-SITE DETECTOR 118 is operative to detect a plurality of POTENTIAL NOVEL TARGET GENES HAVING BINDING-SITE/S 144 the nucleotide sequence of which is partially or fully complementary to that of each of the plurality of DICER-CUT SEQUENCES FROM HAIRPIN STRUCTURES 140. Preferred operation of the TARGET GENE BINDING-SITE DETECTOR 118 is further described hereinbelow with reference to FIG. 14B.

Figure 14B:
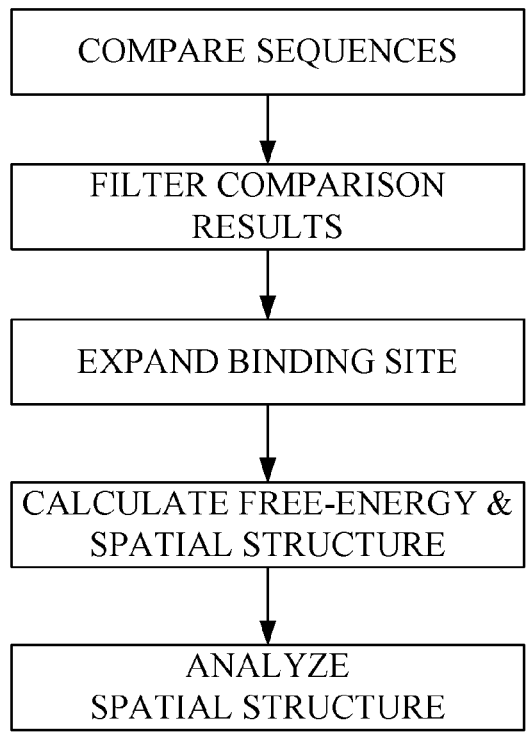
FIG. 14B is a simplified flowchart illustrating operation of a target gene binding-site detector constructed and operative in accordance with a preferred embodiment of the present invention.

Reference is now made to FIG. 14B which is a simplified flowchart illustrating a preferred operation of the TARGET GENE BINDING-SITE DETECTOR 118 of FIG. 9. In a preferred embodiment of the present invention, the TARGET GENE BINDING-SITE DETECTOR 118 employs a sequence comparison algorithm such as BLAST in order to compare the nucleotide sequence of each of the plurality of DICERCUT SEQUENCES FROM HAIRPIN STRUCTURES 140 (FIG. 13A), to the POTENTIAL TARGET GENE SEQUENCES 142 (FIG. 14A), such as untranslated regions of known mRNAs, in order to find crude potential matches. Alternatively, the sequence comparison may be performed using a sequence match search tool that is essentially a variant of the EDIT DISTANCE algorithm described hereinabove with reference to FIG. 13C, and the Nearest Neighbor algorithm.

A sequence comparison of DICER-CUT SEQUENCES FROM HAIRPIN STRUCTURES 140 (FIG. 14A) are compared to POTENTIAL TARGET GENE SEQUENCES 142 (FIG. 14A) by utilizing BLAST or other algorithms such as EDIT DISTANCE.

The results are preferably filtered according to a threshold determined in accordance with the scoring resulting from the sequence comparison carried out by the TARGET GENE BINDING-SITE DETECTOR TRAINING & VALIDATION FUNCTIONALITY 128.

Next the binding sites are expanded, and determinations are made whether if nucleotide sequences immediately adjacent to the binding sites found by the sequence comparison algorithm (e.g. BLAST or EDIT DISTANCE), may improve the match.

Free-energy and spatial structure are computed for the resulting binding sites. Binding sites which are clustered are strongly preferred and binding sites found in evolutionarily conserved sequences may also be preferred. Free energy, spatial structure and the above preferences are reflected in scoring.

The resulting scores are compared with scores characteristic of known binding sites (e.g. binding sites of known miRNA oligonucleotides Lin-4 and Let-7 to target genes Lin-14, Lin-41, Lin 28 etc.).

For each candidate binding site a score, here termed Binding Site Prediction Accuracy, is calculated which estimates its similarity to known binding sites. This score is based on GAM binding site characteristics including, but not limited to:

The free energy of binding of the GAM RNA-GAM RNA binding site complex;

Additionally or alternatively, the 5' and/or 3' ends of the GAM RNA, preferably represented by the relationship between their locations and the locations of one or more nucleotides along the GAM RNA; Additionally or alternatively, the 5' and/or 3' ends of the GAM RNA, preferably represented by the relationship between their locations and the locations of one or more bound nucleotide pairs along the GAM RNA binding site complex; Additionally or alternatively, the 5' and/or 3' ends of the GAM RNA, preferably represented by the relationship between their locations and the locations of one or more mismatched nucleotide pairs along the GAM RNA binding-site complex; Additionally or alternatively, the 5' and/or 3' ends of the GAM RNA, preferably represented by the relationship between their locations and the locations of one or more unmatched nucleotides along the GAM RNA binding-site complex.

In accordance with another preferred embodiment of the present invention, binding sites are searched by a reversed process. Sequences of K (preferably 22) nucleotides of a untranslated regions of a target gene are assessed as potential binding sites. A sequence comparison algorithm, such as BLAST or EDIT DISTANCE, is then used to search elsewhere in the genome for partially or fully complementary sequences which are found in known miRNA oligonucleotides or computationally predicted GAM oligonucleotides. Only complementary sequences, which meet predetermined spatial structure and free energy criteria as described hereinabove are accepted. Clustered binding sites are strongly preferred and potential binding sites and potential GAM oligonucleotides which occur in evolutionarily conserved genomic sequences are also preferred. Scoring of candidate binding sites takes into account free energy and spatial structure of the binding site complexes, as well as the aforesaid preferences.

Target binding sites identified by the TARGET GENE BINDING-SITE DETECTOR 118 (FIG. 9), are preferably divided into four groups:

a) binding sites which are exactly complementary to the predicted GAM RNA. (1 nt. mismatch is allowed)
b) binding sites which are not exactly complementary to the predicted GAM RNA and having 0.8=<Binding Site Prediction Accuracy<1;
c) binding sites which are not exactly complementary to the predicted GAM RNA and having 0.7=<Binding Site Prediction Accuracy<0.8; and
d) binding sites which are not exactly complementary to the predicted GAM RNA and having 0.6=<Binding Site Prediction Accuracy<0.7.

The average number of mismatched nucleotides in the alignment of predicted GAM RNA and a corresponding target gene binding-site is smallest in category a and largest in category d.

In accordance with a preferred embodiment of the present invention there is provided a binding site specific ranking, indicative of the degree of similarity of characteristics of the binding of a GAM to a target gene binding site, to binding characteristic of known miRNAs. This ranking preferably utilizes the evaluation criteria described hereinabove.

In accordance with another preferred embodiment of the present invention, there is provided a UTR specific ranking of GAM to target gene binding., indicative of the degree of similarity of characteristics of the binding of a GAM to a cluster of target gene binding sites on a UTR, to binding characteristics of known miRNAs to UTRs of corresponding miRNA target genes. This ranking preferably is a weighted sum of the binding site specific rankings of various clustered binding sites.

Figure 15:
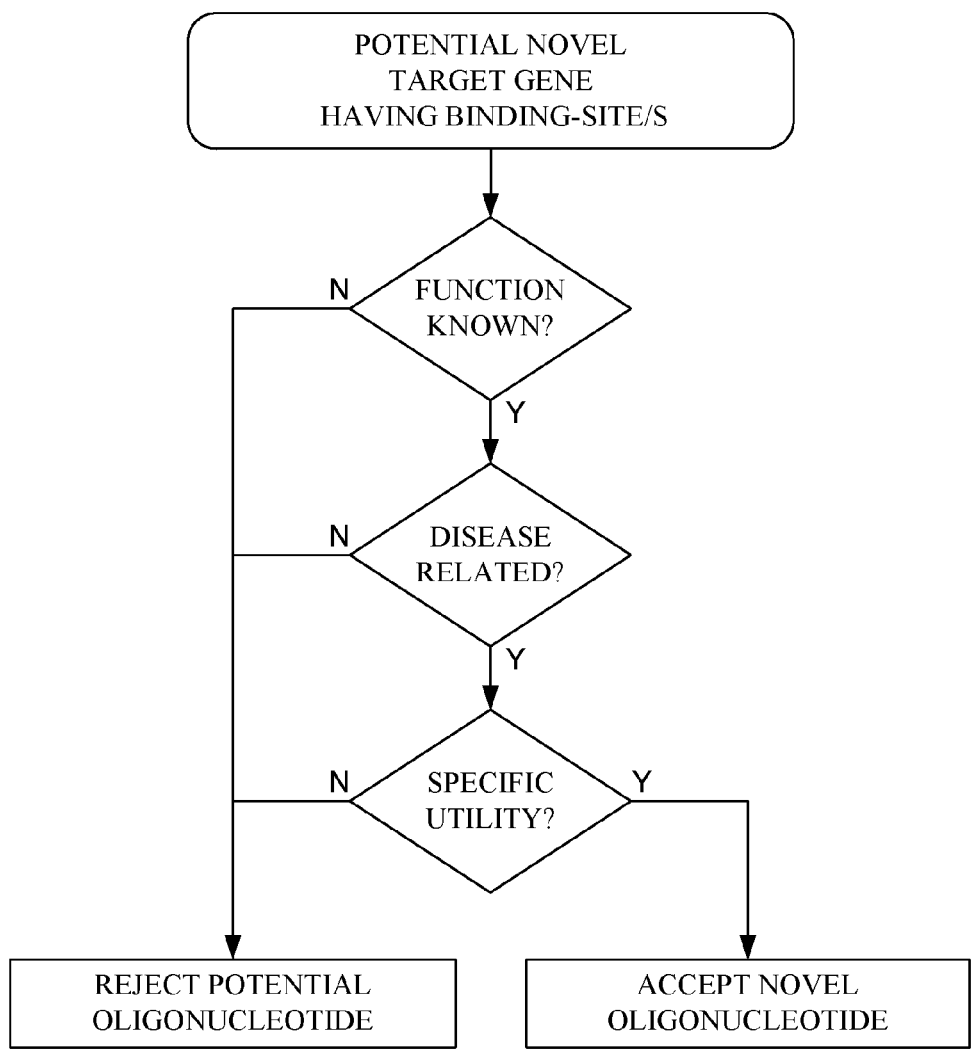
FIG. 15 is a simplified flowchart illustrating operation of a function & utility analyzer constructed and operative in accordance with a preferred embodiment of the present invention.

Reference is now made to FIG. 15 which is a simplified flowchart illustrating a preferred operation of the FUNCTION & UTILITY ANALYZER 120 described hereinabove with reference to FIG. 9. The goal of the FUNCTION & UTILITY ANALYZER 120 is to determine if a potential target gene is in fact a valid clinically useful target gene. Since a potential novel GAM oligonucleotide binding a binding site in the UTR of a target gene is understood to inhibit expression of that target gene, and if that target gene is shown to have a valid clinical utility, then in such a case it follows that the potential novel oligonucleotide itself also has a valid useful function which is the opposite of that of the target gene.

The FUNCTION & UTILITY ANALYZER 120 preferably receives as input a plurality of POTENTIAL NOVEL TARGET GENES HAVING BINDING-SITE/S 144 (FIG. 14A), generated by the TARGET GENE BINDING-SITE DETECTOR 118 (FIG. 9). Each potential oligonucleotide is evaluated as follows: First, the system checks to see if the function of the potential target gene is scientifically well established. Preferably, this can be achieved bioinformatically by searching various published data sources presenting information on known function of proteins. Many such data sources exist and are published as is well known in the art. Next, for those target genes the function of which is scientifically known and is well documented, the system then checks if scientific research data exists which links them to known diseases. For example, a preferred embodiment of the present invention utilizes the OMIM™ (Hamosh et al, 2002) database published by NCBI, which summarizes research publications relating to genes which have been shown to be associated with diseases. Finally, the specific possible utility of the target gene is evaluated. While this process too may be facilitated by bioinformatic means, it might require manual evaluation of published scientific research regarding the target gene, in order to determine the utility of the target gene to the diagnosis and or treatment of specific disease. Only potential novel oligonucleotides, the target genes of which have passed all three examinations, are accepted as novel oligonucleotide.

Figure 16:
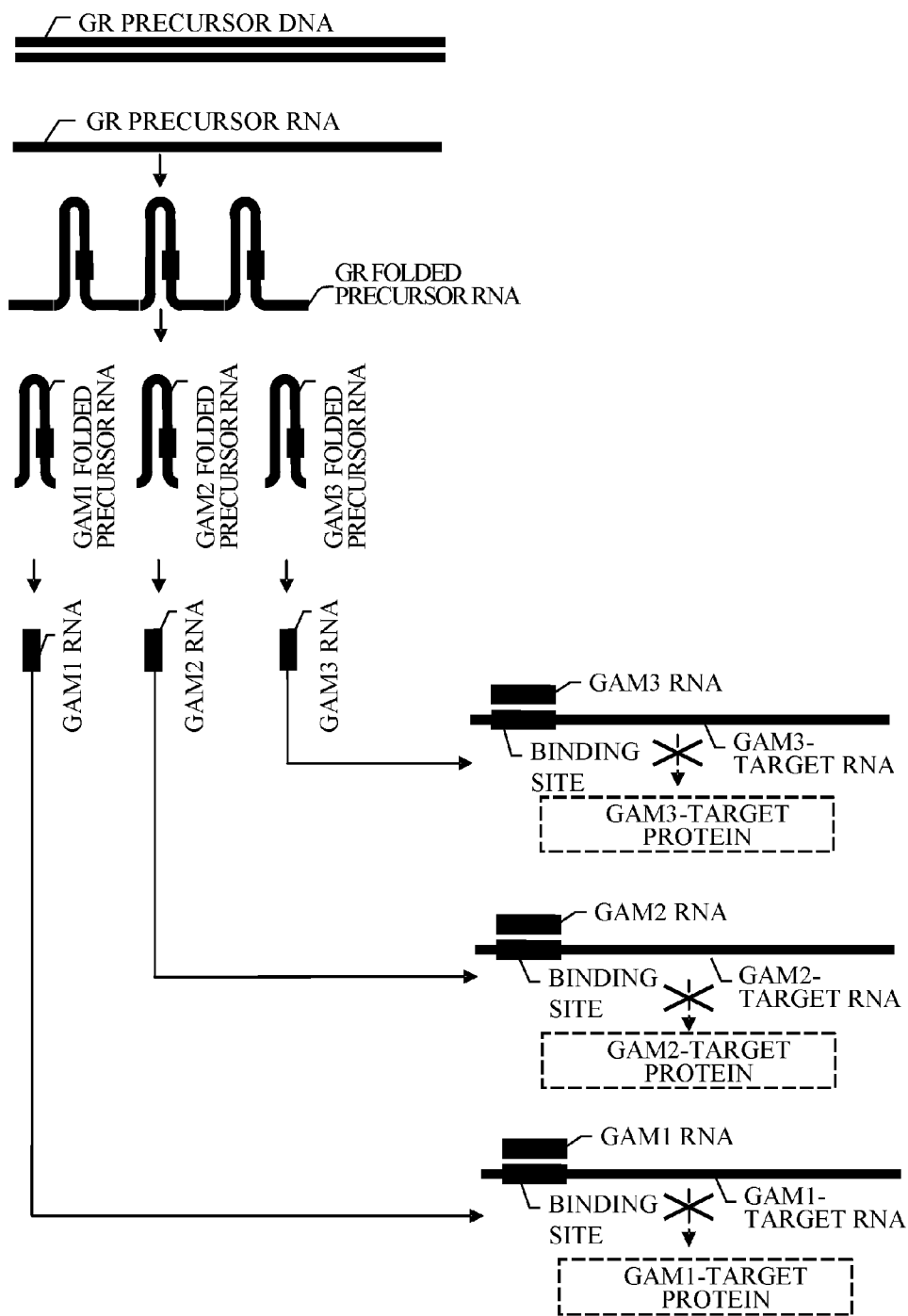
FIG. 16 is a simplified diagram describing a novel bioinformatically detected group of regulatory polynucleotides referred to here as Genomic Record (GR) polynucleotide, each of which encodes an 'operon-like' cluster of novel miRNA-like oligonucleotides, which in turn modulates expression of one or more target genes.

Reference is now made to FIG. 16, which is a simplified diagram describing each of a plurality of novel bioinformatically detected regulatory polynucleotide, referred to here as Genomic Record (GR) polynucleotide which encodes an 'operon-like' cluster of novel micro RNA-like oligonucleotides each of which in turn modulates expression of at least one target gene, the function and utility of which at least one target gene is known in the art. GR GPRECURSOR DNA is a novel bioinformatically detected regulatory, non protein coding, polynucleotide. The method by which GR polynucleotide as detected is described hereinabove with additional reference to FIGS. 9-18. GR GPRECURSOR DNA encodes GR PRECURSOR RNA, an RNA molecule, typically several hundreds to several thousands nucleotides long. GR PRECURSOR RNA folds spatially, forming GR FOLDED PRECURSOR RNA. It is appreciated that GR FOLDED PRECURSOR RNA comprises a plurality of what is known in the art as 'haipin' structures. These 'hairpin structures' are due to the fact that the nucleotide sequence of GR PRECURSOR RNA comprises a plurality of segments, the first half of each such segment having a nucleotide sequence which is at least a partial or accurate complementary sequence of the second half thereof, as is well known in the art. GR FOLDED PRECURSOR RNA is naturally processed by cellular enzymatic activity into separate GAM precursor RNAs, herein schematically represented by GAM1 FOLDED PRECURSOR RNA through GAM3 FOLDED PRECURSOR RNA, each of which GAM precursor RNAs being a hairpin shaped RNA segment, corresponding to GAM FOLDED PRECURSOR RNA of FIG. 8. The above mentioned GAM precursor RNAs are diced by DICER COMPLEX of FIG. 8, yielding respective short RNA segments of about 22 nucleotides in length, schematically represented by GAM1 RNA through GAM3 RNA, each of which GAM RNAs corresponding to GAM RNA of FIG. 8. GAM1 RNA, GAM2 RNA and GAM3 RNA, each bind complementarily to binding sites located in untranslated regions of respective target genes, designated GAM1-TARGET RNA, GAM2-TARGET RNA and GAM3-TARGET RNA, respectively, which target binding site corresponds to a target binding site such as BINDING SITE I, BINDING SITE II or BINDING SITE III of FIG. 8. This binding inhibits translation of the respective target proteins designated GAM1-TARGET PROTEIN, GAM2-TARGET PROTEIN and GAM3-TARGET PROTEIN respectively. It is appreciated that specific functions, and accordingly utilities, of each GR polynucleotides of the present invention, correlates with, and may be deduced from, the identity of the target genes, which are inhibited by GAM RNAs comprised in the 'operon-like' cluster of said GR polynucleotide schematically represented by GAM1 TARGET PROTEIN through GAM3 TARGET PROTEIN.

A listing of GAM oligonucleotide comprised in each of a plurality of GR polynucleotide of FIG. 16 is provided in Table 10, hereby incorporated herein. Nucleotide sequences of each said GAM oligonucleotide and their respective genomic source and chromosomal location are further described hereinbelow with reference to Table 3 hereby incorporated herein. GAM TARGET GENEs of each of said GAM oligonucleotides are elaborated hereinbelow with reference to Table 7, hereby incorporated herein. The functions of each of said GAM TARGET GENEs and their association with various diseases, and accordingly the utilities of said each of GAM oligonucleotides and hence the functions and utilities of each of said GR polynucleotides are elaborated hereinbelow with reference to Table 8, hereby incorporated herein. Studies establishing known functions of each of said GAM TARGET GENEs, and correlation of each of said GAM TARGET GENEs to known diseases are listed in Table 9, and are hereby incorporated herein.

The present invention discloses 246 novel genes of the GR group of polynucleotides, which have been detected bioinformatically. Laboratory confirmation of 2 polynucleotides of the GR group of polynucleotides is described hereinbelow with reference to FIGS. 23A-24D.

In summary, the current invention discloses a very large number of novel GR polynucleotides each of which encodes a plurality of GAM oligonucleotides, which in turn may modulate expression of a plurality of target proteins. It is appreciated therefore that the function of GR polynucleotides is in fact similar to that of the Genomic Records concept of the present invention addressing the differentiation enigma, described hereinabove with reference to FIG. 7.

Figure 17:
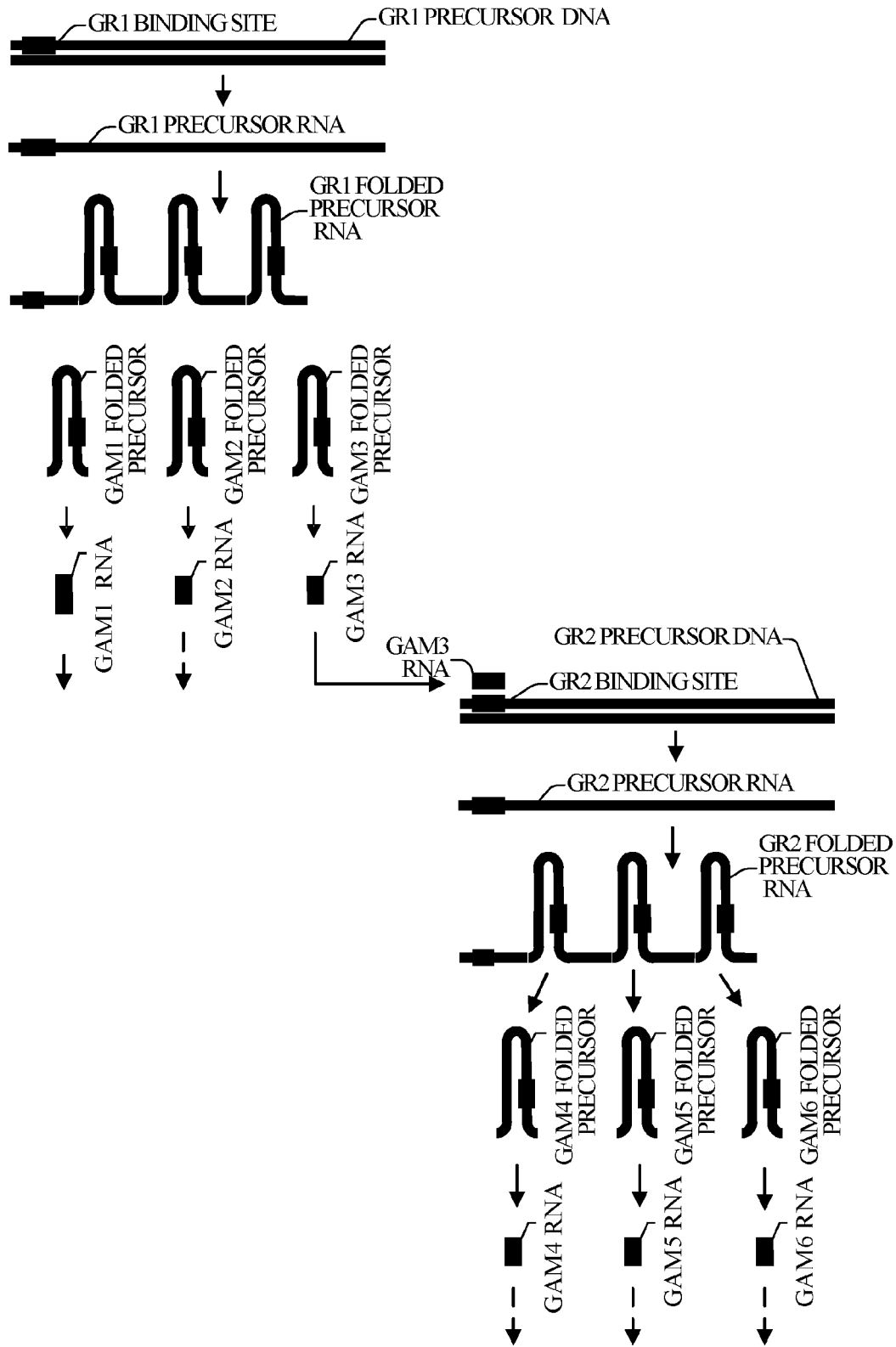
FIG. 17 is a simplified diagram illustrating a mode by which oligonucleotides of a novel group of operon-like polynucleotide of the present invention, modulate expression of other such polynucleotides, in a cascading manner.

Reference is now made to FIG. 17 which is a simplified diagram illustrating a mode by which oligonucleotides of a novel group of operon-like polynucleotide described hereinabove with reference to FIG. 16 of the present invention, modulate expression of other such polynucleotide, in a cascading manner. GR1 PRECURSOR DNA and GR2 PRECURSOR DNA are two polynucleotides of the novel group of operon-like polynucleotides designated GR PRECURSOR DNA (FIG. 16). As is typical of polynucleotides of the GR group of polynucleotides GR1 PRECURSOR DNA and GR2 PRECURSOR DNA, each encode a long RNA precursor, which in turn folds into a folded RNA precursor comprising multiple hairpin shapes, and is cut into respective separate hairpin shaped RNA segments, each of which RNA segments being diced to yield a n oligonucleotide of a group of oligonucleotide designated GAM RNA. In this manner GR1 yields GAM1 RNA, GAM2 RNA and GAM3 RNA, and GR2 yields GAM4 RNA, GAM5 RNA and GAM6 RNA. As FIG. 17 shows, GAM3 RNA, which derives from GR1, binds a binding site located adjacent to GR2 GPRECURSOR DNA thus modulating expression of GR2, thereby invoking expression of GAM4 RNA, GAM5 RNA and GAM6 RNA which derive from GR2. It is appreciated that the mode of modulation of expression presented by FIG. 17 enables an unlimited 'cascading effect' in which a GR polynucleotide comprises multiple GAM oligonucleotides each of which may modulate expression of other GR polynucleotides each such GR polynucleotides comprising additional GAM oligonucleotide etc., whereby eventually certain GAM oligonucleotides modulate expression of target proteins. This mechanism is in accord with the conceptual model of the present invention addressing the differentiation enigma, described hereinabove with specific reference to FIGS. 6-7.

Figure 18:
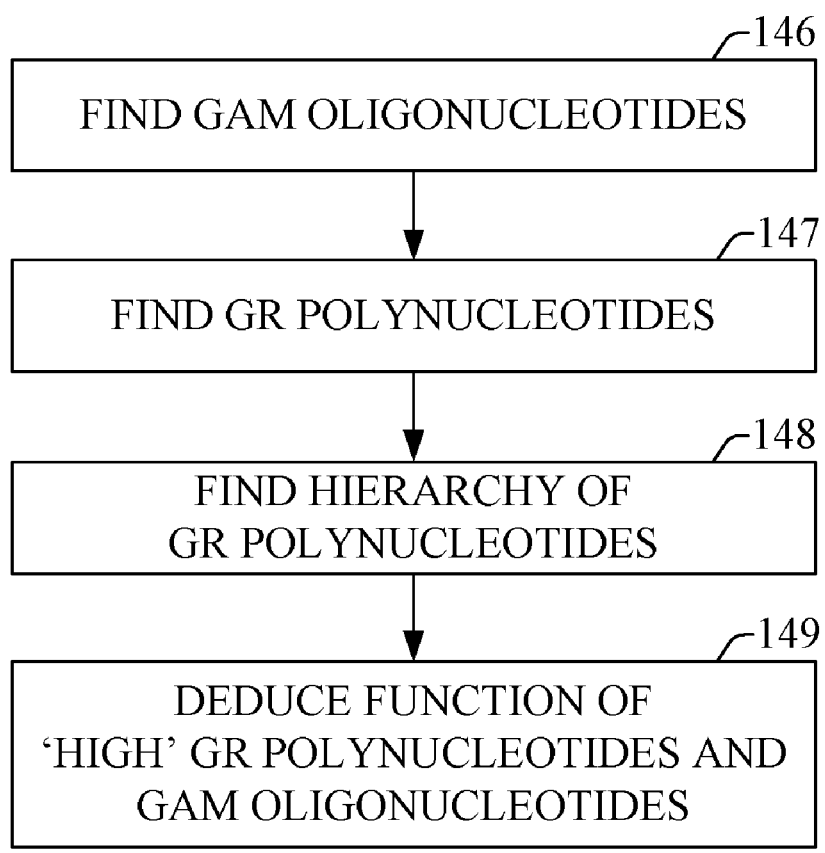
FIG. 18 is a block diagram illustrating an overview of a methodology for finding novel oligonucleotides and novel operon-like polynucleotides of the present invention, and their respective functions.

Reference is now made to FIG. 18 which is a block diagram illustrating an overview of a methodology for finding novel oligonucleotides and operon-like polynucleotides of the present invention, and their respective functions. According to a preferred embodiment of the present invention, the methodology to finding novel oligonucleotides of the present invention and their function comprises of the following major steps: First, FIND GAM OLIGONUCLEOTIDES 146 is used to detect, oligonucleotide of the novel group of oligonucleotide of the present invention, referred to here as GAM oligonucleotide. GAM oligonucleotides are located and their function elicited by detecting target proteins they bind and the function of those target proteins, as described hereinabove with reference to FIGS. 9-15. Next, FIND GR POLYNUCLEOTIDES 147 is used to detect polynucleotide of a novel group of operon-like polynucleotide of the present invention, referred to here as GR polynucleotide. GR polynucleotides are located, by locating clusters of proximally located GAM oligonucleotide, based on the previous step. Consequently, FIND HIERARCHY OF GR POLYNUCLEOTIDES 148 elicits the hierarchy of GR and GAM: binding sites for non-protein-binding GAM oligonucleotide comprised in each GR polynucleotide found are sought adjacent to other GR polynucleotides. When found, such a binding site indicates that the connection between the GAM and the GR the expression of which it modulates, and thus the hierarchy of the GR polynucleotides and the GAM oligonucleotides they comprise. Lastly, DEDUCE FUNCTION OF HIGH GR POLYNUCLEOTIDES AND GAM OLIGONUCLEOTIDES 149 is used to deduce the function of GR polynucleotides and GAM oligonucleotides which are 'high' in the hierarchy, i.e. GAM oligonucleotides which modulate expression of other GR polynucleotides rather than directly modulating expression of target proteins. A preferred approach is as follows: The function of protein-modulating GAM oligonucleotides is deducible from the proteins which they modulate, provided that the function of these target proteins is known. The function of 'higher' GAM oligonucleotides may be deduced by comparing the function of protein-modulating GAM oligonucleotides with the hierarchical relationships by which the 'higher' GAM oligonucleotides are connected to the protein-modulating GAM oligonucleotides. For example, given a group of several protein-modulating GAM oligonucleotides which collectively cause a protein expression pattern typical of a certain cell-type, then a 'higher' GAM oligonucleotide is sought which modulates expression of GR polynucleotides which perhaps modulate expression of other GR polynucleotides which eventually modulate expression of the given group of protein-modulating GAM oligonucleotide. The 'higher' GAM oligonucleotide found in this manner is taken to be responsible for differentiation of that cell-type, as per the conceptual model of the invention described hereinabove with reference to FIG. 6.

Figure 19:
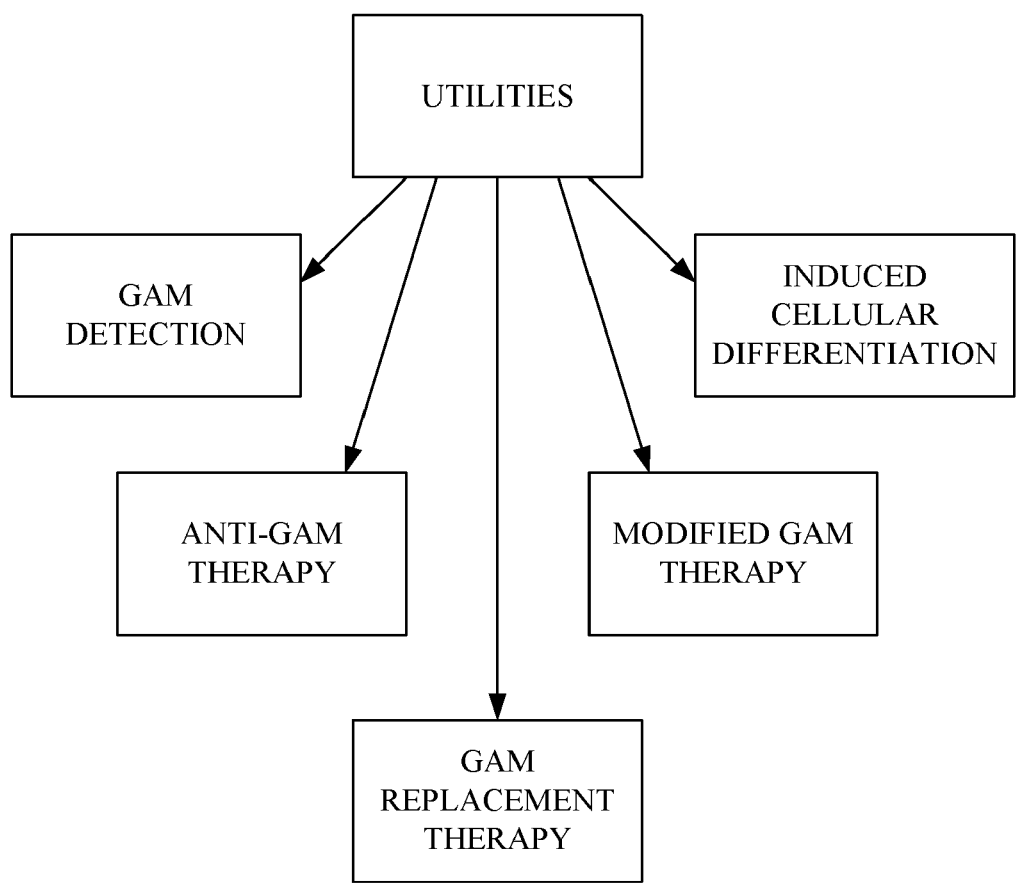
FIG. 19 is a block diagram illustrating different utilities of novel oligonucleotides and novel operon-like polynucleotides, both of the present invention.

Reference is now made to FIG. 19 which is a block diagram illustrating different utilities of oligonucleotide of the novel group of oligonucleotides of the present invention referred to here as GAM oligonucleotides and GR polynucleotides. The present invention discloses a first plurality of novel oligonucleotides referred to here as GAM oligonucleotides and a second plurality of operon-like polynucleotides referred to here as GR polynucleotides each of the GR polynucleotide encoding a plurality of GAM oligonucleotides The present invention further discloses a very large number of known target genes, which are bound by, and the expression of which is modulated by each of the novel oligonucleotides of the present invention. Published scientific data referenced by the present invention provides specific, substantial, and credible evidence that the above mentioned target genes modulated by novel oligonucleotides of the present invention, are associated with Alzheimers disease. Specific novel oligonucleotides of the present invention, target genes associated with Alzheimers diseases are described hereinbelow with reference to Tables 1 through 11. It is therefore appreciated that a function of GAM oligonucleotides and GR polynucleotides of the present invention is modulation of expression of target genes related to Alzheimers disease, and that therefore utilities of novel oligonucleotides of the present invention include diagnosis and treatment of Alzheimers disease. FIG. 19 describes various types of diagnostic and therapeutic utilities of novel oligonucleotides of the present invention. A utility of novel oligonucleotides of the present invention is detection of GAM oligonucleotides and of GR polynucleotides. It is appreciated that since GAM oligonucleotides and polynucleotides modulate expression of disease related target genes, that detection of expression of GAM oligonucleotides in clinical scenarios associated with said diseases is a specific, substantial and credible utility. Diagnosis of novel oligonucleotides of the present invention may preferably be implemented by RNA expression detection techniques, including but not limited to biochips, as is well known in the art. Diagnosis of expression of oligonucleotides of the present invention may be useful for research purposes, in order to further understand the connection between the novel oligonucleotides of the present invention and the Alzheimers disease, for disease diagnosis and prevention purposes, and for monitoring disease progress. Another utility of novel oligonucleotides of the present invention is anti-GAM therapy, a mode of therapy which allows up regulation of the disease related target gene of a novel GAM oligonucleotide of the present invention, by lowering levels of the novel GAM oligonucleotide which naturally inhibits expression of that target gene. This mode of therapy is particularly useful with respect to target genes which have been shown to be under-expressed in association with Alzheimers disease. Anti-GAM therapy is further discussed hereinbelow with reference to FIGS. 20A and 20B. A further utility of novel oligonucleotides of the present invention is GAM replacement therapy, a mode of therapy which achieves down regulation of Alzheimers related target gene of a novel GAM oligonucleotide of the present invention, by raising levels of the GAM which naturally inhibits expression of that target gene. This mode of therapy is particularly useful with respect to target genes which have been shown to be over-expressed in Alzheimers disease. GAM replacement therapy involves introduction of supplementary GAM products into a cell, or stimulation of a cell to produce excess GAM products. GAM replacement therapy may preferably be achieved by transfecting cells with an artificial DNA molecule encoding a GAM which causes the cells to produce the GAM product, as is well known in the art. Yet a further utility of novel oligonucleotides of the present invention is modified GAM therapy. Disease conditions are likely to exist, in which a mutation in a binding site of a GAM RNA prevents natural GAM RNA to effectively bind inhibit a disease related target gene, causing up regulation of that target gene, and thereby contributing to the disease pathology. In such conditions, a modified GAM oligonucleotides is designed which effectively binds the mutated GAM binding site, i.e. is an effective anti-sense of the mutated GAM binding site, and is introduced in disease effected cells. Modified GAM therapy is preferably achieved by transfecting cells with an artificial DNA molecule encoding the modified GAM which causes the cells to produce the modified GAM product, as is well known in the art. An additional utility of novel GAM of the present invention is induced cellular differentiation therapy. As aspect of the present invention is finding oligonucleotides which determine cellular differentiation, as described hereinabove with reference to FIG. 18. Induced cellular differentiation therapy comprises transfection of cell with such GAM oligonucleotides thereby determining their differentiation as desired. It is appreciated that this approach may be widely applicable, inter alia as a means for auto transplantation harvesting cells of one cell-type from a patient, modifying their differentiation as desired, and then transplanting them back into the patient. It is further appreciated that this approach may also be utilized to modify cell differentiation in vivo, by transfecting cells in a genetically diseased tissue with a cell-differentiation determining GAM thus stimulating these cells to differentiate appropriately.

Figure 20A:
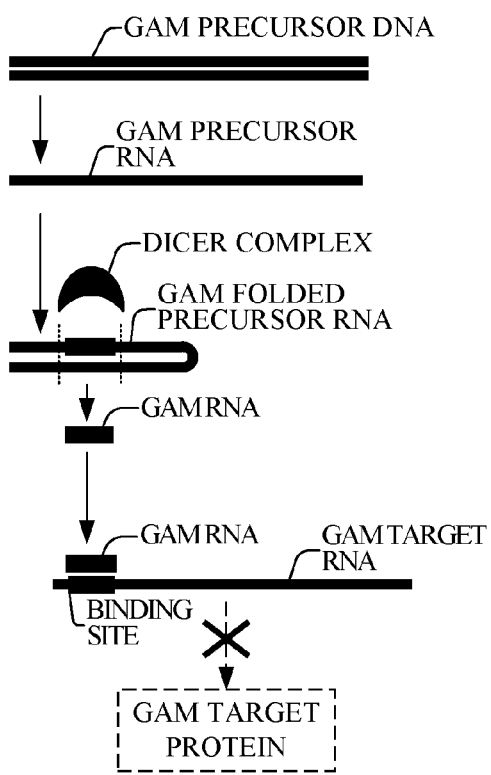
FIGS. 20A and 20B are simplified diagrams, which when taken together illustrate a mode of oligonucleotide-therapy applicable to novel oligonucleotides of the present invention.
Figure 20B:
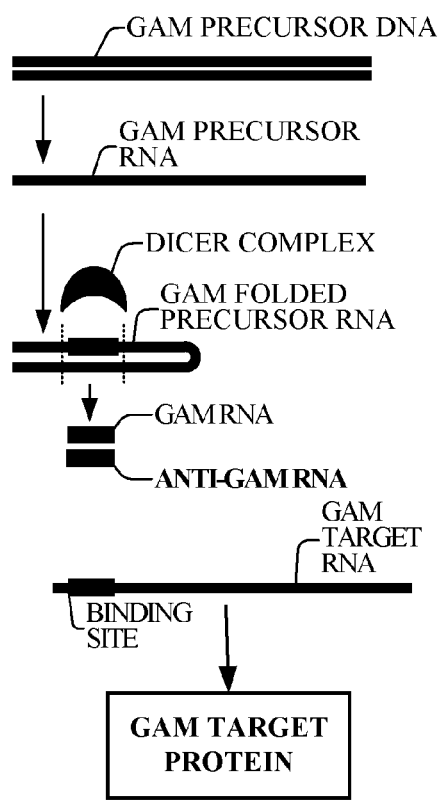

Reference is now made to FIGS. 20A and 20B, simplified diagrams which when taken together illustrate anti-GAM therapy mentioned hereinabove with reference to FIG. 19. A utility of novel GAMs of the present invention is anti-GAM therapy, a mode of therapy which allows up regulation of Alzheimers disease related target gene of a novel GAM of the present invention, by lowering levels of the novel GAM which naturally inhibits expression of that target gene. FIG. 20A shows a normal GAM inhibiting translation of a target gene of GAM RNA by binding to a BINDING SITE found in an untranslated region of GAM TARGET RNA, as described hereinabove with reference to FIG. 8.

FIG. 20B shows an example of anti-GAM therapy. ANTI-GAM RNA is short artificial RNA molecule the sequence of which is an anti-sense of GAM RNA. Anti-GAM treatment comprises transfecting diseased cells with ANTI-GAM RNA, or with a DNA encoding thereof. The ANTI-GAM RNA binds the natural GAM RNA, thereby preventing binding of natural GAM RNA to its BINDING SITE. This prevents natural translation inhibition of GAM TARGET RNA by GAM RNA, thereby up regulating expression of GAM TARGET PROTEIN.

It is appreciated that anti-GAM therapy is particularly useful with respect to target genes which have been shown to be under-expressed in Alzheimers disease. Furthermore, anti-GAM therapy is particularly useful, since it may be used in situations in which technologies known in the art as RNAi and siRNA can not be utilized. As in known in the art, RNAi and siRNA are technologies which offer means for artificially inhibiting expression of a target protein, by artificially designed short RNA segments which bind complementarily to mRNA of said target protein. However, RNAi and siRNA can not be used to directly up regulate translation of target proteins.

Figure 21A:
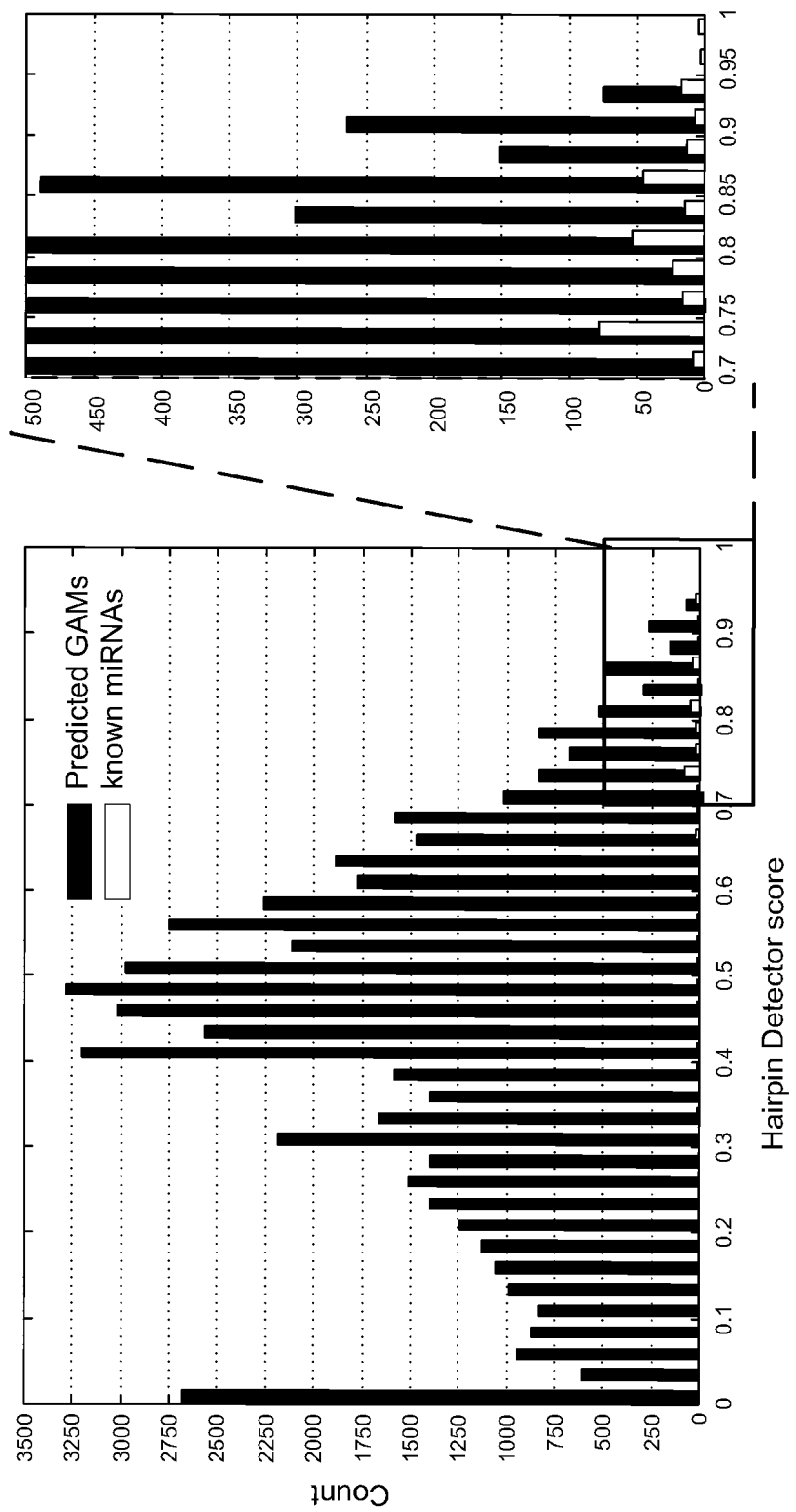
FIG. 21A is a histogram representing the distribution of known miRNA oligonucleotides, and that of miRNA-like hairpin-shaped oligonucleotides, predicted by the bioinformatics detection engine of the present invention, extracted from expressed genome sequences with respect to their hairpin detector score.

Reference is now made to FIG. 21A, which is a histogram representing the distribution of known miRNA oligonucleotides and that of hairpin structures extracted from expressed genome sequences with respect to their HAIRPIN DETECTOR score. The known miRNA oligonucleotide s set is taken from RFAM database, Release 2.1 and include 440 miRNA oligonucleotides from *H. sapienas, M. musculus, C. elegans, C. brigassae* and *D. melanogaster*. Folding of expressed genome sequences taken from public databases of ESTs (Unigene-NCBI and TIGR) identified 342,882 hairpin structures. ~154,000 out of the 342,882 hairpin structures did not pass the filter of being identified as hairpins in several secondary structure folding versions of the given genomic sequence, as described hereinabove with reference to FIG. 12B, and hence did not receive a Hairpin detector score. Furthermore, ~133,000 hairpin structures did not pass the filter of minimum score of the DICER-CUT LOCATION DETECTOR 116 (FIG. 9) (those ~287,000 hairpin structures are not represented in the histogram). Hairpin structures are considered as miRNA-like precursor oligonucleotides here referred to as GAM oligonucleotide, if their Hairpin detector score is above 0.3. Thus, the GAM oligonucleotides set is comprised of 40,000 hairpin structures, of those ~5100 received a high Hairpin detector score (>=0.7). These are much higher numbers than those of the known miRNA oligonucleotides and of the upper bound of ~255 human miRNA oligonucleotide s, estimated by Bartel et al (Science, 299, 1540, March 2003). Of the reference set that pass the above filter (408/440), 284 (69%) received a high Hairpin detector score (>=0.7).

Reference is now made to FIG. 21B, which is a table summarizing laboratory validation results that validate efficacy of the BIOINFORMATIC OLIGONUCLEOTIDE DETECTION ENGINE 100 (FIG. 9). In order to assess efficacy of the BIOINFORMATIC OLIGONUCLEOTIDE DETECTION ENGINE 100, novel oligonucleotides predicted thereby are preferably divided into 4 detection accuracy groups (first column), designated A through D, ranking GAMS from the most probable GAMs to the least probable GAMs, using the scores of HAIRPIN DETECTOR 114 (FIG. 9) and DICER-CUT LOCATION DETECTOR 116 (FIG. 9) as follows:

Group A: The score of the HAIRPIN-DETECTOR is above 0.7, the overall score of the two-phased predictor is above 0.55, and the score of the second phase of the two-phased predictor is above 0.75, or the score of the EDIT-DISTANCE predictor is equal or above 17. In this group, one Dicer cut location is predicted for each hairpin. Group B: The score of the HAIRPIN-DETECTOR is above 0.5, the overall score of the two-phased predictor is above 0.55, and the hairpin is not in group A. Group C: The score of the HAIRPIN-DETECTOR is between 0.4 and 0.5, and the overall score of the two-phased predictor is above 0.55. Group D: The score of the HAIRPIN-DETECTOR is between 0.3 and 0.4, and the overall score of the two-phased predictor is above 0.55. In groups B, C and D, if the score of the second phase of the two-phased predictor is above 0.75, one Dicer cut location is predicted for each hairpin, otherwise both sides of the double stranded window are given as output, and are examined in the lab or used for binding site search. The groups are mutually exclusive, i.e. in groups A, C and D all hairpins score less than 17 in the EDIT-DISTANCE predictor.

It is appreciated that the division into groups is not exhaustive: 410 of the 440 published hairpins (second column), and 1419 of the 1708 novel GAMs, belong to one of the groups. An indication of the real performance of the two-phased predictor in the presence of background hairpins is given by the column 'precision on hairpin mixture' (third column). The precision on hairpin mixture is computed by mixing the published miRNA hairpins with background hairpins in a ratio of 1:4 and taking as a working assumption that they are hairpins not carrying a 'diced' miRNA-like oligonucleotide This is a strict assumption, since some of these background hairpins may indeed contain 'diced' miRNAs-like oligonucleotide, while in this column they are all counted as failures Sample novel bioinformatically predicted human GAMs of each of these groups are sent to the laboratory for validation (fourth column), and the number (fifth column) and percent (sixth column) of successful validation of predicted human GAM is noted for each of the groups, as well as overall (bottom line). The number of novel VAM genes explicitly specified by present invention belonging to each of the four groups is noted (seventh column).

It is appreciated that the present invention comprises 1419 novel GAM oligonucleotides, which fall into one of these four detection accuracy groups, and that the BIOINFORMATIC OLIGONUCLEOTIDE DETECTION ENGINE 100 (FIG. 9) is substantiated by a group of 52 novel human GAM oligonucleotides validated by laboratory means, out of 168 human GAM oligonucleotides which were tested in the lab, resulting in validation of an overall 31% accuracy. The top group demonstrated 37% accuracy. Pictures of test-results of specific human GAM oligonucleotides in the abovementioned four groups, as well as the methodology used for validating the expression of predicted oligonucleotides are elaborated hereinbelow with reference to FIG. 22.

It is further appreciated that failure to detect a predicted GAM oligonucleotide in the lab does not necessarily indicate a mistaken bioinformatic prediction. Rather, it may be due to technical sensitivity limitation of the lab test, or because the GAM oligonucleotides not expressed in the tissue examined, or at the development phase tested.

It is still further appreciated that in general these findings are in agreement with the expected bioinformatic accuracy, as describe hereinabove with reference to FIG. 13B: assuming 80% accuracy of the HAIRPIN DETECTOR 114 and 80% accuracy of the DICER-CUT LOCATION DETECTOR 116 and 80% accuracy of the lab validation, this would result in 50% overall accuracy of the GAM oligonucleotide validated in the lab.

Figure 22A:

Reference is now made to FIG. 22A which is a picture of laboratory results validating the expression of 43 novel genes detected by the BIOINFORMATIC OLIGONUCLEOTIDE DETECTION ENGINE 100 (FIG. 9).

Reference is now made to FIG. 22A and FIG. 22B which are pictures and a summary table of laboratory results validating the expression of 43 novel human GAM oligonucleotides detected by the BIOINFORMATIC OLIGONUCLEOTIDE DETECTION ENGINE 100. In each row in FIG. 22A, pictures of several oligonucleotides validated by hybridization of Polymerase Chain Reaction (PCR)-product southern-blots, are provided, each corresponding to a specific GAM oligonucleotides, as elaborated hereinbelow. To test our validation method, we used a reference set of 8 known human miRNA oligonucleotides, as blind test to our laboratory. These PCR-product hybridization pictures are designated 1 through 8 for the reference set known miRNA oligonucleotides; and 9 through 51 for predicted GAM oligonucleotides.

In each PCR hybridization picture, 2 lanes are seen: the test lane, designated "+" and the control lane, designated "−". For convenience of viewing the results, all PCR-product hybridization pictures of FIG. 22A have been shrunk ×4 vertically. It is appreciated that for each of the tested GAM oligonucleotides a clear hybridization band appears in the test ("+") lane, but not in the control ("−") lane.

Specifically, FIG. 22A shows pictures of PCR-product hybridization validation by southern-blot, the methodology of which is described hereinbelow, to the following novel human GAM oligonucleotides (RosettaGenomics Ltd. Nomenclature, 'A' and 'B' referred to the Dicer Cut Location as described hereinabove with reference to the description of large tables:

(1) hsa-MIR-21; (2) hsa-MIR-27b; (3) hsa-MIR-186; (4) hsa-MIR-93; (5) hsa-MIR-26a; (6) hsa-MIR-191; (7) hsa-MIR-31; (8) hsa-MIR-92; (9) GAM3418-A (later published by other researchers as hsa-MIR23); (10) GAM4426-A; (11) GAM281-A; (12) GAM7553-A; (13) GAM5385-A; (14) GAM2608-A; (15) GAM1032-A; (16) GAM3431-A; (17) GAM7933-A; (18) GAM3298-A; (19) GAM7080-A; (20) GAM895-A; (21) GAM3770.1; (22) GAM337162-A; (23) GAM8678-A; (24) GAM2033-A; (25) GAM7776-A; (26) GAM8145-A; (27) GAM25-A; (28) GAM7352.1; (29) GAM337624-A; (30) GAM1479-A; (31) GAM2270-A; (32) GAM7591-A; (33) GAM8285-A; (34) GAM6773-A; (35) GAM336818-A; (36) GAM336487-A; (37) GAM337620-A; (38) GAM336809-A; (39) GAM5346-A; (40) GAM8554-A; (41) GAM2071-A; (42) GAM7957-A; (43) GAM391-A; (44) GAM6633-A; (45) GAM19; (46) GAM8358-A; (47) GAM3229-A; an) GAM 7052-A; (49) GAM3027-A; (50) GAM21 and (51) GAM oligonucleotide similar to mmu-MIR-30e.

The next validated GAM oligonucleotides are highly similar or highly identical to known mouse-miRNA oligonucleotides: GAM3027-A, similar to mmu-MIR-29c; GAM21, similar to mmu-MIR-130b; and GAM oligonucleotide which is highly similar to mmu-MIR-30e (picture number 51). In addition to the PCR—product hybridization detection, the following GAMs were cloned and sequenced: GAM3418-A, GAM5385-A, GAM1032-A, GAM3298-A, GAM7080-A, GAM1338-A, GAM7776-A, GAM25-A, GAM337624-A, GAM1479-A, GAM6773-A, GAM336818-A, GAM336487-A, GAM337620-A, GAM336809-A, GAM3027-A, GAM21, and GAM oligonucleotide similar to mmu-MIR-30e (picture number 51). Furthermore, the following GAM oligonucleotides were sequenced directly from the ligation reaction by the method described hereinbelow under LIGATION-PCR DIAGNOSTIC METHOD: GAM4426-A, GAM7553-A, GAM2270-A, and GAM7591-A.

In order to validate the expression of predicted novel GAM and assuming that these novel GAM oligonucleotides are probably expressed at low concentrations, a PCR product cloning approach was set up through the following strategy: two types of cDNA libraries designated "One tailed" and "Ligation" were prepared from frozen HeLa S100 extract (4c Biotech, Belgium) size fractionated RNA. Essentially, Total S100 RNA was prepared through an SDS-Proteinase K incubation followed by an acid Phenol-Chloroform purification and Isopropanol precipitation. Alternatively, total HeLa RNA was also used as starting material for these libraries.

Fractionation was done by loading up to 500 g per YM100 Amicon Microcon column (Millipore) followed by a 500 g centrifugation for 40 minutes at 4 C. Flow through "YM100"RNA consisting of about of the total RNA was used for library preparation or fractionated further by loading onto a YM30 Amicon Microcon column (Millipore) followed by a 13,500 g centrifugation for 25 minutes at 4 C. Flowthrough "YM30" was used for library preparation as is and consists of less than 0.5% of total RNA. For the both the "ligation" and the "One-tailed" libraries, RNA was dephosphorylated and ligated to an RNA (lowercase)-DNA (UPPERCASE) hybrid 5"-phosphorylated, 3"idT blocked 3"-adapter (5"-P-uuuAACCGCATCCTTCTC-idT-3" (SEQ ID NO: 7419) Dharmacon #P-002045-01-05) (as elaborated in Elbashir et al., Genes Dev. 15:188-200 (2001)) resulting in ligation only of RNase III type cleavage products. 3"-Ligated RNA was excised and purified from a half 6%, half 13% polyacrylamide gel to remove excess adapter with a Nanosep 0.2M centrifugal device (PalI) according to instructions, and precipitated with glycogen and 3 volumes of Ethanol. Pellet was resuspended in a minimal volume of water.

For the "ligation" library a DNA (UPPERCASE)-RNA (lowercase) hybrid 5"-adapter (5"-TACTAATACGACT-CACTaaa-3" (SEQ ID NO: 7420) Dharmacon # P-002046-01-05) was ligated to the 3"-adapted RNA, reverse transcribed with "EcoRI-RT": (5"-GACTAGCTGGAATTCAAGGATGCGGTTAAA-3") (SEQ ID NO: 7421), PCR amplified with two external primers essentially as in Elbashir et al 200 1 except that primers were "EcoRI-RT" and "PstI Fwd" (5"-CAGCCAACGCTG-CAGATACGACTCACTAAA-3") (SEQ ID NO: 7422). This PCR product was used as a template for a second round of PCR with one hemispecific and one external primer or with two hemispecific primers.

For the "One tailed" library the 3"-Adapted RNA was annealed to 20 pmol primer "EcoRI RT" by heating to 70 C and cooling 0.1 C/sec to 30 C and then reverse transcribed with Superscript II RT (According to instructions, Invitrogen) in a 20 l volume for 10 alternating 5 minute cycles of 37 C and 45 C. Subsequently, RNA was digested with 1 1 2M NaOH, 2 mM EDTA at 65 C for 10 minutes. cDNA was loaded on a polyacrylamide gel, excised and gel-purified from excess primer as above (invisible, judged by primer run alongside) and resuspended in 13 l of water. Purified cDNA was then oligo-dC tailed with 400 U of recombinant terminal transferase (Roche molecular biochemicals), 1 l 100M dCTP, 1 l 15 mM CoCl2, and 4 l reaction buffer, to a final volume of 20 l for 15 minutes at 37 C. Reaction was stopped with 2 l 0.2M EDTA and 15 l 3M NaOAc pH 5.2. Volume was adjusted to 150 l with water, Phenol:Bromochloropropane 10:1 extracted and subsequently precipitated with glycogen and 3 volumes of Ethanol. C-tailed cDNA was used as a template for PCR with the external primers "T3-PstBsg(G/I) 18" (5"-AAT-TAACCCTCACTAAAGGCTGCAGGTGCAG-GIGGGIIGGGIIGG GIIGN-3" (SEQ ID NO: 7423) where I stands for Inosine and N for any of the 4 possible deoxynucleotides), and with "EcoRI Nested" (5"-GGAATTCAAGGAT-GCGGTTA-3")" (SEQ ID NO: 7424). This PCR product was used as a template for a second round of PCR with one hemispecific and one external primer or with two hemispecific primers.

Hemispecific primers were constructed for each predicted GAM RNA oligonucleotide by an in-house program designed to choose about half of the 5" or 3" sequence of the GAM RNA corresponding to a TM of about 30-34 C constrained by an optimized 3"clamp, appended to the cloning adapter sequence (for "One-tailed" libraries 5"-GGN-NGGGNNG (SEQ ID NO: 7425) on the 5" end of the GAM RNA, or TTTAACCGCATC-3" (SEQ ID NO: 7426) on the 3"end of the GAM RNA. For "Ligation" libraries the same 3" adapter and 5"-CGACTCACTAAA (SEQ ID NO: 7427) on the 5" end). Consequently, a fully complementary primer of a TM higher than 60 C was created covering only one half of the GAM RNA sequence permitting the unbiased elucidation by sequencing of the other half.

Confirmation of GAM Oligonucleotide Sequence Authenticity of PCR Products:

SOUTHERN BLOT: PCR-product sequences were confirmed by southern blot (Southern E. M., Biotechnology, 1992, 24:122-39 (1975)) and hybridization with DNA oligonucleotide probes synthesized against predicted GAM RNAs oligonucleotides. Gels were transferred onto a Biodyne PLUS 0.45 m, (PalI) positively charged nylon membrane and UV cross-linked. Hybridization was performed overnight with DIG-labeled probes at 420 C in DIG EasyHyb buffer (Roche). Membranes were washed twice with 2×SSC and 0.1% SDS for 10 min. at 420 C and then washed twice with 0.5×SSC and 0.1% SDS for 5 min at 420 C. The membrane was then developed by using a DIG luminescent detection kit (Roche) using anti-DIG and CSPD reaction, according to the manufacturer's protocol. All probes were prepared according to the manufacturers (Roche Molecular Biochemicals) protocols: Digoxigenin (DIG) labeled antisense transcripts was prepared from purified PCR products using a DIG RNA labeling kit with T3 RNA polymerase. DIG labeled PCR was prepared by using a DIG PCR labeling kit. 3"-DIG-tailed oligo ssDNA antisense probes, containing DIG-dUTP and dATP at an average tail length of 50 nucleotides were prepared from 100 pmole oligonucleotides with the DIG Oligonucleotide Labeling Kit.

CLONE-SEQUENCING: PCR products were inserted into pGEM-T (Promega) or pTZ57 (MBI Fermentas), transformed into competent JM109 *E. coli* (Promega) and sown on LB-Amp plates with IPTG/Xgal. White and light-blue colonies were transferred to duplicate gridded plates, one of which was blotted onto a membrane (Biodyne Plus, PalI) for hybridization with DIG tailed oligo probes (according to instructions, Roche) corresponding to the expected GAM. Plasmid DNA from positive colonies was sequenced.

LIGATION-PCR DIAGNOSTIC METHOD: To further validate predicted GAM PCR product sequence derived from hemiprimers, a PCR based diagnostic technique was devised to amplify only those products containing also at least two additional nucleotides of the non hemi-primer defined part of the predicted GAM RNA oligonucleotide. In essence, a diagnostic primer was designed so that its 3" end, which is the specificity determining side, was identical to the desired GAMRNA oligonucleotide, 2-10 nucleotides (typically 4-7, chosen for maximum specificity) further into its 3" end than the nucleotide stretch primed by the hemi-primer. The hemi-primer PCR product was first ligated into a T-cloning vector (pTZ57/T or pGEM-T) as described herinabove. The ligation reaction mixture was used as template for the diagnostic PCR under strict annealing conditions with the new diagnostic primer in conjunction with a general plasmid-homologous primer, resulting in a distinct ~200 base-pair product. This PCR product can be directly sequenced, permitting the elucidation of the remaining nucleotides up to the 3" of the mature GAM RNA oligonucleotide adjacent to the 3" adapter. Alternatively, following analysis of the diagnostic PCR reaction on an agarose gel, positive ligation reactions (containing a band of the expected size) were transformed into *E. coli*. Using this same diagnostic technique and as an alternative to screening by Southern-blot colonyhybridization, transformed bacterial colonies were screened by colony-PCR (Gussow, D. and Clackson, T, Nucleic Acids Res. 17: 4000 (1989)) prior to plasmid purification and sequencing.

Reference is now made to FIG. 22B which is a table summarizing laboratory results which validate the expression of 8 known human miRNA oligonucleotides and 43 novel GAM oligonucleotides detected by the BIOINFORMATIC OLIGONUCLEOTIDE DETECTION ENGINE 100. The table gives additional information on the above GAM oligonucleotides and contains the following fields: NUMBER: refer to the hybridization picture number of FIG. 22A; NAME: indicate the known MIR name for the reference set or GAM's name as given by RosettaGenomices nomenclature method; SEQUENCE: 5' to 3' sequence of the mature, 'diced' oligonucleotide; SEQUENCED: '+' indicates a validation of the GAM RNA sequence by sequencing procedure as described hereinabove with reference to FIG. 22A.

Figures 23A, 23B, 23C:
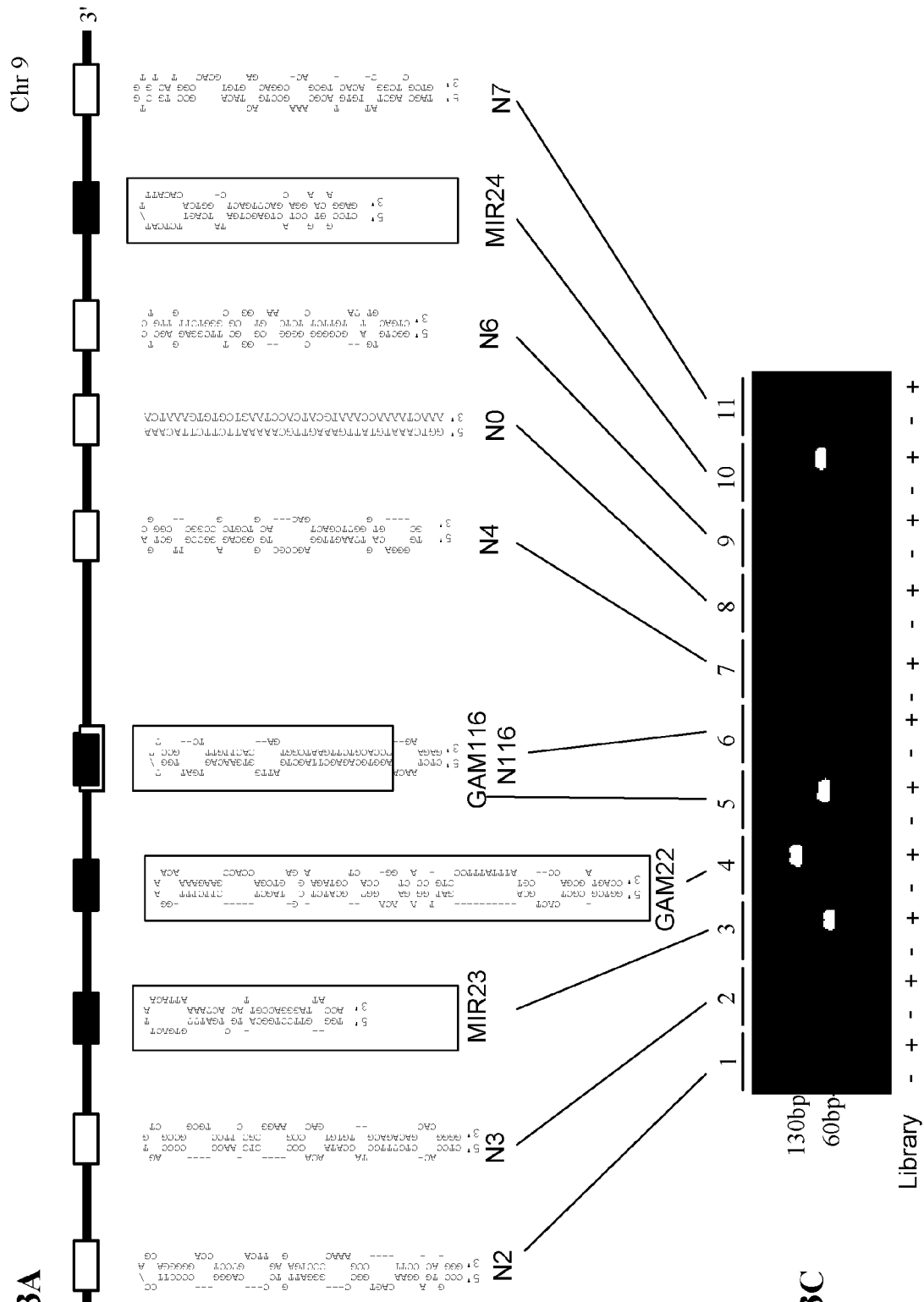
FIG. 23A is a schematic representation of an "operon-like" cluster of novel hairpin sequences detected bioinformatically by a bioinformatic oligonucleotide detection engine constructed and operative in accordance with a preferred embodiment of the present invention, and non-GAM hairpin useful as negative controls thereto.
FIG. 23B is a schematic representation of secondary folding of hairpins of the operon-like cluster of FIG. 23A. The hairpins shown are as follows: N2 (SEQ ID NO: 7403), N3 (SEQ ID NO: 7404), MIR23 (SEQ ID NO: 7405), GAM22 (SEQ ID NO: 7406), GAM116 (SEQ ID NO: 7407), N116 (SEQ ID NO: 7408), N4 (SEQ ID NO: 7409), N0 (SEQ ID NO: 7410), N6 (SEQ ID NO: 7411), MIR24 (SEQ ID NO: 7412), and N7 (SEQ ID NO: 7413)
FIG. 23C is a picture of laboratory results demonstrating expression of novel oligonucleotides of FIGS. 23A and 23B, and lack of expression of the negative controls, thereby validating efficacy of bioinformatic detection of GAM oligonucleotides and GR polynucleotides of the present invention, by a bioinformatic oligonucleotide detection engine constructed and operative in accordance with a preferred embodiment of the present invention.

Reference is now made to FIG. 23A, which is a schematic representation of a novel human GR polynucleotide herein designated GR12731 (RosettaGenomics Ltd. nomenclature), located on chromosome 9, comprising 2 known human MIR genes—MIR24 and MIR23, and 2 novel GAM oligonucleotides, herein designated GAM22 and GAM116, all marked by solid black boxes. FIG. 23A also schematically illustrates 6 non-GAM hairpin sequences, and one non-hairpin sequence, all marked by white boxes, and serving as negative controls. By "non-GAM hairpin sequences" is meant sequences of a similar length to known MIR PRECURSOR sequences, which form hairpin secondary folding pattern similar to MIR PRECURSOR hairpins, and yet which are assessed by the BIOINFORMATIC OLIGONUCLEOTIDE DETECTION ENGINE 100 not to be valid GAM PRECURSOR hairpins. It is appreciated that FIG. 23A is a simplified schematic representation, reflecting only the order in which the segments of interest appear relative to one another, and not a proportional distance between the segments.

Reference is now made to FIG. 23B, which is a schematic representation of secondary folding of each of the MIRs and GAMs of GR GR12731 MIR24, MIR23, GAM22 and GAM116, and of the negative control non-GAM hairpins, herein designated N2, N3, N116, N4, N6 and N7. N0 is a non-hairpin control, of a similar length to that of known MIR PRECURSOR hairpins. It is appreciated that the negative controls are situated adjacent to and in between real MIR genes and GAM predicted oligonucleotide and demonstrates similar secondary folding patterns to that of known MIRs and GAMs.

Reference is now made to FIG. 23C, which is a picture of laboratory results of a PCR test upon a YM100 "ligation"-library, utilizing specific primer sets directly inside the boundaries of the hairpins. Due to the nature of the library the only PCR amplifiable products can result from RNaseIII type enzyme cleaved RNA, as expected for legitimate hairpin precursors presumed to be produced by DROSHA (Lee et al, Nature 425 415-419, 2003). FIG. 23C demonstrates expression of hairpin precursors of known MIR genes—MIRhsa-23 and MIRhsa-24, and of novel bioinformatically detected GAM22 and GAM116 hairpins predicted bioinformatically by a system constructed and operative in accordance with a preferred embodiment of the present invention. FIG. 23C also shows that none of the 7 controls (6 hairpins designated N2, N3, N23, N4, N6 and N7 and 1 non-hairpin sequence designated N0) were expressed. N116 is a negative control sequence partially overlapping GAM116.

In the picture, test lanes including template are designated "+" and the control lane is designated "−". It is appreciated that for each of the tested hairpins, a clear PCR band appears in the test ("+") lane, but not in the control ("−") lane.

FIGS. 23A through 23C, when taken together validate the efficacy of the bioinformatic oligonucleotide detection engine in: (a) detecting known MIR genes; (b) detecting novel GAM PRECURSOR hairpins which are found adjacent to these MIR genes, and which despite exhaustive prior biological efforts and bioinformatic detection efforts, went undetected; (c) discerning between GAM (or MIR) PRECURSOR hairpins, and non-GAM hairpins.

It is appreciated that the ability to discern GAM-hairpins from non-GAM-hairpins is very significant in detecting GAM oligonucleotide since hairpins in general are highly abundant in the genome. Other MIR prediction programs have not been able to address this challenge successfully.

Reference is now made to FIG. 24A which is an annotated sequence of an EST comprising a novel GAM oligonucleotides detected by the oligonucleotide detection system of the present invention. FIG. 24A shows the nucleotide sequence of a known human non-protein coding EST (Expressed Sequence Tag), identified as EST72223. The EST72223 clone obtained from TIGR database (Kirkness and Kerlavage, 1997) was sequenced to yield the above 705 bp transcript with a polyadenyl tail. It is appreciated that the sequence of this EST comprises sequences of one known miRNA oligonucleotide, identified as hsa-MIR98, and of one novel GAM oligonucleotide referred to here as GAM25, detected by the BIOINFORMATIC OLIGONUCLEOTIDE DETECTION ENGINE 100 (FIG. 9) of the present invention.

The sequences of the precursors of the known MIR98 and of the predicted GAM25 are precursor in bold, the sequences of the established miRNA 98 and of the predicted miRNA-like oligonucleotide GAM25 are underlined.

Figure 24D:
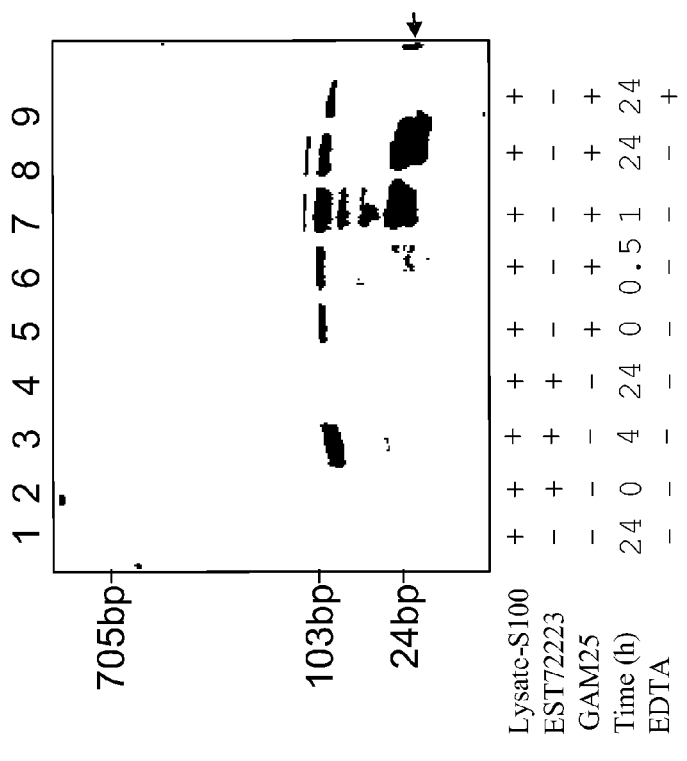
Figure 24C:
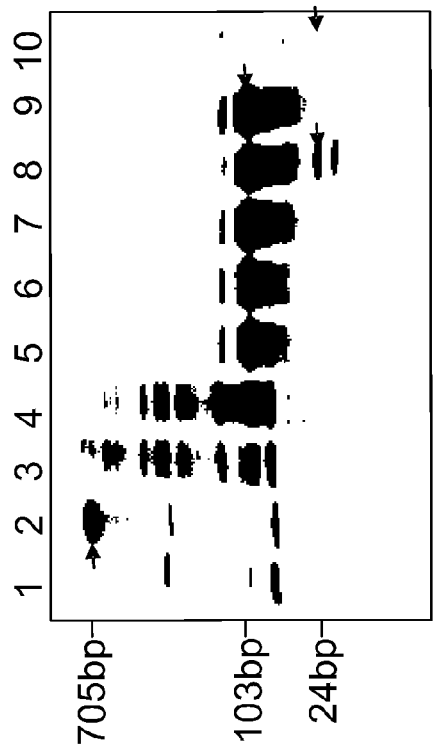

Reference is now made to FIGS. 24B, 24C and 24D that are pictures of laboratory results, which when taken together demonstrate laboratory confirmation of expression of the bioinformatically detected novel oligonucleotide of FIG. 24A. In two parallel experiments, an enzymatically synthesized capped, EST72223 RNA transcript, was incubated with Hela S100 lysate for 0 minutes, 4 hours and 24 hours. RNA was subsequently harvested, run on a denaturing polyacrylamide gel, and reacted with a 102 nt and a 145 nt antisense MIR98 and GAM25 precursor transcript probes respectively. The Northern blot results of these experiments demonstrated processing of EST72223 RNA by Hela lysate (lanes 2-4, in 24B and 24C), into ~80 bp and ~22 bp segments, which reacted with the MIR98 precursor probe (24B), and into ~100 bp and ~24 bp segments, which reacted with the GAM25 precursor probe (24C). These results demonstrate the processing of EST72223 by Hela lysate into MIR98 precursor and GAM25 precursor. It is also appreciated from FIG. 24C (lane 1) that Hela lysate itself reacted with the GAM25 precursor probe, in a number of bands, including a ~100 bp band, indicating that GAM25-precursor is endogenously expressed in Hela cells. The presence of additional bands, higher than 100 bp in lanes 5-9 probably corresponds to the presence of nucleotide sequences in Hela lysate, which contain the GAM25 sequence.

In addition, in order to demonstrate the kinetics and specificity of the processing of MIR98 and GAM25 precursors into their respective mature, 'diced' segments, transcripts of MIR98 and of the bioinformatically predicted GAM25 precursors were similarly incubated with Hela S100 lysate, for 0 minutes, 30 minutes, 1 hour and 24 hours, and for 24 hours with the addition of EDTA, added to inhibit Dicer activity, following which RNA was harvested, run on a polyacrylamide gel and reacted with MIR98 and GAM25 precursor probes. Capped transcripts were prepared for in-vitro RNA cleavage assays with T7 RNA polymerase including a m7G (5')ppp(5')G-capping reaction the Message Machine kit (Ambion). Purified PCR products were used as template for the reaction. These were amplified for each assay with specific primers containing a T7 promoter at the 5" end and a T3 RNA polymerase promoter at the 3" end. Capped RNA transcripts were incubated at 30 C in supplemented, dialysis concentrated, Hela S100 cytoplasmic extract (4 C Biotech, Seneffe, Belgium). The Hela S100 was supplemented by dialysis to a final concentration of 20 mM Hepes, 100 mM KCl, 2.5 mM MgCl2, 0.5 mM DTT, 20% glycerol and protease inhibitor cocktail tablets (Complete mini Roche Molecular Biochemicals). After addition of all components, final concentrations were 100 mM capped target RNA, 2 mM ATP, 0.2 mM GTP, 500 U/ml RNasin, 25 g/ml creatine kinase, 25 mM creatine phosphate, 2.5 mM DTT and 50% S100 extract. Proteinase K, used to enhance Dicer activity (Zhang et al., EMBO J. 21, 5875-5885 (2002)) was dissolved in 50 mM Tris-HCl pH 8, 5 mM CaCl2, and 50% glycerol, was added to a final concentration of 0.6 mg/ml. Cleavage reactions were stopped by the addition of 8 volumes of proteinase K buffer (200 Mm Tris-Hcl, pH 7.5, 25 mM EDTA, 300 mM NaCl, and 2% SDS) and incubated at 65 C for 15 min at different time points (0, 0.5, 1, 4, 24 h) and subjected to phenol/chloroform extraction. Pellets were dissolved in water and kept frozen. Samples were analyzed on a segmented half 6%, half 13% polyacrylamide 1XTBE-7M Urea gel.

The Northern blot results of these experiments demonstrated an accumulation of a ~22 bp segment which reacted with the MIR98 precursor probe, and of a ~24 bp segment which reacted with the GAM25 precursor probe, over time (lanes 5-8). Absence of these segments when incubated with EDTA (lane 9), which is known to inhibit Dicer enzyme (Zhang et al., 2002), supports the notion that the processing of MIR98 and GAM25 precursors into their 'diced' segments is mediated by Dicer enzyme, found in Hela lysate. The molecular sizes of EST72223, MIR-98 and GAM25 and their corresponding precursors are indicated by arrows.

FIG. 24D present Northern blot results of same above experiments with GAM25 probe (24 nt). The results clearly demonstrated the accumulation of mature GAM25 oligonucleotide after 24 h.

To validate the identity of the band shown by the lower arrow in FIGS. 24C and 24D, a RNA band parallel to a marker of 24 base was excised from the gel and cloned as in Elbashir et al (2001) and sequenced. 90 clones corresponded to the sequence of mature GAM25 oligonucleotide, three corresponded to GAM25* (the opposite arm of the hairpin with a 1-3 nucleotide 3" overhang) and two to the hairpin-loop.

GAM25 was also validated endogenously by sequencing from both sides from a HeLa YM100 total-RNA "ligation" libraries, utilizing hemispecific primers as described in FIG. 22.

Taken together, these results validate the presence and processing of a novel MIR-like oligonucleotide, GAM25, which was predicted bioinformatically. The processing of this novel GAM oligonucleotide product, by Hela lysate from EST72223, through its precursor, to its final form was similar to that observed for known miRNA oligonucleotide, MIR98.

Transcript products were 705 nt (EST72223), 102 nt (MIR98 precursor), 125 nt (GAM25 precursor) long. EST72223 was PCR amplified with T7-EST 72223 forward primer: 5"-TAATACGACTCACTATAGGCCCTTATTA-GAGGATTCTGCT-3" (SEQ ID NO: 7428) and T3-EST72223 reverse primer: "-AATTAACCCTCAC-TAAAGGTTTTTTTTTCCTGAGACAGAGT-3" (SEQ ID NO: 7429). MIR98 was PCR amplified using EST72223 as a template with T7MIR98 forward primer: 5-"TAATACGACT-CACTATAGGGTGAGGTAGTAAGTTGTATTGTT-3" (SEQ ID NO: 7430) and T3MIR98 reverse primer: 5"-AAT-TAACCCTCACTAAAGGGAAAGTAG-TAAGTTGTATAGTT-3" (SEQ ID NO: 7431). GAM25 was PCR amplified using EST72223 as a template with GAM25 forward primer: 5"-GAGGCAGGAGAATTGCTTGA-3" (SEQ ID NO: 7432) and T3-EST72223 reverse primer: 5"-AATTAACCCTCACTAAAGGCCTGAGACA-GAGTCTTGCTC-3" (SEQ ID NO: 7433).

It is appreciated that the data presented in FIGS. 24A, 24B, 24C and 24D when taken together validate the function of the bioinformatic oligonucleotide detection engine 100 of FIG. 9. FIG. 24A shows a novel GAM oligonucleotide bioinformatically detected by the BIOINFORMATIC OLIGONUCLE-OTIDE DETECTION ENGINE 100, and FIGS. 24C and 24D show laboratory confirmation of the expression of this novel oligonucleotide. This is in accord with the engine training and validation methodology described hereinabove with reference to FIG. 10.

DETAILED DESCRIPTION OF LARGE TABLES

Table 1 comprises data relating the SEQ ID NO of GAM RNA oligonucleotides of the present invention to their corresponding GAM NAME, and contains the following fields: GAM SEQ-ID: GAM SEQ ID NO, as in the Sequence Listing; GAM NAME: Rosetta Genomics Ltd. nomenclature (see below); GAM RNA SEQUENCE: Sequence (5' to 3') of the mature, 'diced' GAM RNA; GAM POS: Dicer cut location (see below); and Table 2 comprises detailed textual description according to the description of FIG. 8 of each of a plurality of novel GAM oligonucleotide of the present invention, and contains the following fields: GAM NAME: Rosetta Genomics Ltd. nomenclature (see below); PRECUR SEQ-ID: GAM precursor Seq-ID, as in the Sequence Listing; PRECURSOR SEQUENCE: Sequence (5' to 3') of the GAM precursor; GAM DESCRIPTION: Detailed description of GAM oligonucleotide with reference to FIG. 8; and Table 3 comprises data relating to the source and location of novel GAM oligonucleotides of the present invention, and contains the following fields: GAM NAME: Rosetta Genomics Ltd. nomenclature (see below); PRECUR SEQ-ID: GAM precursor SEQ ID NO, as in the Sequence Listing; ORGANISM: Abbreviated (hsa=Homo sapiens); CHR: Chromosome encoding the GAM oligonucleotide; STRAND: Orientation on the chromosome, '+' for the plus strand, '−' for the minus strand; CHR-START OFFSET Start offset of GAM precursor sequence on the chromosome; CHR-END OFFSET: End offset of GAM precursor sequence on the chromosome; SOURCE_REF-ID: Accession number of source sequence; and Table 4 comprises data relating to GAM precursors of novel GAM oligonucleotides of the present invention, and contains the following fields: GAM NAME: Rosetta Genomics Ltd. nomenclature (see below); PRECUR SEQ-ID: GAM precursor Seq-ID, as in the Sequence Listing; PRECURSOR-SEQUENCE: Sequence (5' to 3') of the GAM precursor; GAM FOLDED PRECURSOR RNA: Schematic representation of the GAM folded precursor, beginning 5' end (beginning of upper row) to 3' end (beginning of lower row), where the hairpin loop is positioned at the right part of the draw; and Table 5 comprises data relating to GAM oligonucleotides of the present invention, and contains the following fields: GAM NAME: Rosetta Genomics Ltd. nomenclature (see below); GAM RNA SEQUENCE: Sequence (5' to 3') of the mature, 'diced' GAM RNA; PRECUR SEQ-ID: GAM precursor Seq-ID, as in the Sequence Listing; SOURCE_REF_ID: accession number of the source sequence; GAM POS: Dicer cut location (see below); and Table 6 comprises data relating SEQ ID NO of the GAM target gene binding site sequence to TARGET gene name and target binding site sequence, and contains the following fields: TARGET BINDING SITE SEQ-ID: Target binding site SEQ ID NO, as in the Sequence Listing; TARGET: GAM target gene name; TARGET BINDING SITE SEQUENCE: Nucleotide sequence (5' to 3') of the target binding site; and Table 7 comprises data relating to target genes and binding sites of GAM oligonucleotides of the present invention, and contains the following fields: GAM NAME: Rosetta Genomics Ltd. nomenclature (see below); GAM RNA SEQUENCE: Sequence (5' to 3') of the mature, 'diced' GAM RNA; TARGET: GAM target gene name; TARGET REF-ID: Target accession number (GenBank); UTR: Untranslated region of binding site/s (3' or 5'); TARGET BS-SEQ: Nucleotide sequence (5' to 3') of the target binding site; BINDING-SITE-DRAW: Schematic representation of the binding site, upper row represent 5' to 3' sequence of the GAM RNA, lower row represent 3' to 5' sequence of the target binding site; GAM POS: Dicer cut location (see below); and Table 8 comprises data relating to functions and utilities of novel GAM oligonucleotides of the present invention, and contains the following fields: GAM NAME: Rosetta Genomics Ltd. nomenclature (see below); TARGET: GAM target gene name; GAM RNA SEQUENCE: Sequence (5' to 3') of the mature, 'diced' GAM RNA; GAM FUNCTION: Description of the GAM functions and utilities; GAM POS: Dicer cut location (see below); TAR DIS: Target Disease Relation Group (see below); and Table 9 comprises data of GAM target gene function references—Bibliography and contains the following fields: GAM NAME: Rosetta Genomics Ltd. nomenclature (see below); GAM RNA SEQUENCE: Sequence (5' to 3') of the mature, 'diced' GAM RNA; TARGET: GAM target gene name; REFERENCES: list of references related to the GAM target gene; GAM POS: Dicer cut location (see below); and Table 10 comprises data relating to novel GR (Genomic Record) polynucleotides of the present invention, and contains the following fields: GR NAME: Rosetta Genomics Ltd. nomenclature (see below); GR DESCRIPTION: Detailed description of a GR polynucleotide cluster, with reference to FIG. 16; and Table 11 comprises data relating to Alzheimers disease that GAM oligonucleotides are predicted to regulate the disease-associated genes. Each row is referred to a specific disease, and list the GAM target genes related to the disease. The first row is a summary of ALL target genes associated in Alzheimer disease containing in the present invention. The second row is a subset of the first row and contains all GAM target genes found to bind to at least one validated GAM oligonucleotide. The table contains the following fields: ROW#: index of the row number; DISEASE NAME: name of the disease; TARGET GENES ASSOCIATED WITH ALZHEIMER: list of GAM target genes that are associated with the specified disease; and The following conventions and abbreviations are used in the tables: The nucleotide 'U' is represented as 'T' in the tables, and GAM NAME or GR NAME are names for nucleotide sequences of the present invention given by RosettaGenomics Ltd. nomenclature method. All GAMs/GRs are designated by GAMx/GRx where x is a unique ID.

SOURCE REF-ID: The accession number of expressed sequences on which novel oligonucleotides were detected.

The sequences are taken from the following published databases: (1) TIGR—"Tentative Human Consensus" (THC) (2) EST database—UNIGENE, NCBI.

GAM POS is a position of the GAM RNA on the GAM PRECURSOR RNA sequence. This position is the Dicer cut location, 'A' indicates a probable Dicer cut location, 'B' indicates an alternative Dicer cut location.

TAR DIS (Target Disease Relation Group) 'A' indicates if the target gene is known to have a specific causative relation to Alzheimers disease, based on the OMIM database (Hamosh et al, 2002). It is appreciated that this is a partial classification emphasizing genes which are associated with "single gene" diseases etc. All GAM oligonucleotides of the present invention ARE associated with Alzheimers disease, although not all are necessary in 'A' status.

All genomic sequences of the present invention as well as their chromosomal location and strand orientation are derived from sequences records of NCBI, Build33 database (April, 2003).

It is appreciated by persons skilled in the art that the present invention is not limited by what has been particularly shown and described hereinabove. Rather the scope of the present invention includes both combinations and subcombinations of the various features described hereinabove as well as variations and modifications which would occur to persons skilled in the art upon reading the specifications and which are not in the prior art.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07906326B2). An electronic copy of the "Sequence Listing" will also be available from the USPTO upon request and payment of the fee set forth in 37 CFR 1.19(b)(3).

The invention claimed is:

1. An isolated nucleic acid selected from the group consisting of:
   (a) SEQ ID NO: 6527;
   (b) a DNA encoding (a), wherein the DNA is identical in length to (a); and,
   (c) the complement of (a) or (b), wherein the complement is identical in length to (a).

2. An isolated nucleic acid selected from the group consisting of:
   (a) SEQ ID NO: 15;
   (b) nucleotides 80-97 of SEQ ID NO: 6527;
   (c) nucleotides 80-98 of SEQ ID NO: 6527;
   (d) nucleotides 80-99 of SEQ ID NO: 6527;
   (e) nucleotides 80-100 of SEQ ID NO: 6527;
   (f) nucleotides 80-102 of SEQ ID NO: 6527;
   (g) nucleotides 80-103 of SEQ ID NO: 6527;
   (h) a DNA encoding any one of (a)-(g), wherein the DNA is identical in length to (a)-(g), respectively; and
   (i) the complement of any one of (a)-(h), wherein the complement is identical in length to (a)-(h), respectively.

3. A vector comprising a human insert, wherein the human insert consists of the nucleic acid of claim 1, and wherein the vector does not comprise a human insert other than the nucleic acid of claim 1.

4. A vector comprising a human insert, wherein the human insert consists of the nucleic acid of claim 2, and wherein the vector does not comprise a human insert other than the nucleic acid of claim 2.

5. An oligonucleotide probe of 131 nucleotides in length, wherein the probe comprises the nucleic acid of claim 1.

6. An oligonucleotide probe of 18-24 or 50-120 nucleotides in length, wherein the probe comprises the nucleic acid of claim 2.

* * * * *